(12) United States Patent
Ziegler et al.

(10) Patent No.: US 11,001,601 B2
(45) Date of Patent: May 11, 2021

(54) COMPOUNDS, COMPOSITIONS AND METHODS FOR COLORING EDIBLE MATERIALS

(71) Applicant: The Penn State Research Foundation, University Park, PA (US)

(72) Inventors: Gregory Ray Ziegler, State College, PA (US); Joshua David Lambert, State College, PA (US); Rachel Marie Shegog, State College, PA (US); Emmanouil Chatzakis, State College, PA (US); Deepti Dabas, Portage, MI (US)

(73) Assignee: The Penn State Research Foundation, University Park, PA (US)

( * ) Notice: Subject to any disclaimer, the term of this patent is extended or adjusted under 35 U.S.C. 154(b) by 775 days.

(21) Appl. No.: 15/343,810

(22) Filed: Nov. 4, 2016

(65) Prior Publication Data

US 2017/0121363 A1     May 4, 2017

Related U.S. Application Data

(60) Provisional application No. 62/250,684, filed on Nov. 4, 2015.

(51) Int. Cl.
| | |
|---|---|
| *C07H 15/26* | (2006.01) |
| *A23L 5/47* | (2016.01) |
| *A23L 5/42* | (2016.01) |
| *C09B 61/00* | (2006.01) |

(52) U.S. Cl.
CPC ............... *C07H 15/26* (2013.01); *A23L 5/42* (2016.08); *A23L 5/47* (2016.08); *C09B 61/00* (2013.01); *A23V 2002/00* (2013.01)

(58) Field of Classification Search
CPC .. A23L 5/42; A23L 5/47; C09B 61/00; C07H 15/26; A23V 2002/00
See application file for complete search history.

(56) References Cited

U.S. PATENT DOCUMENTS

| | | | | |
|---|---|---|---|---|
| 2,550,254 A | * | 4/1951 | Jensen | ............... A61K 36/54 424/123 |
| 4,172,949 A | | 10/1979 | Dunn | |
| 8,658,237 B2 | | 2/2014 | Fukui et al. | |

(Continued)

FOREIGN PATENT DOCUMENTS

| | | |
|---|---|---|
| EP | 1663931 | 6/2006 |
| WO | 2005021479 A1 | 3/2005 |

(Continued)

OTHER PUBLICATIONS

Weatherby et al. Industrial & Engineering Chemistry 23(12): 1421-1423 (1931). (Year: 1931).*

(Continued)

*Primary Examiner* — Subbalakshmi Prakash
(74) *Attorney, Agent, or Firm* — Buchanan Ingersoll & Rooney PC

(57) ABSTRACT

The present invention provides compounds isolated from avocado seeds for use as a natural colorant in edible materials. The compounds of the invention are useful for coloring edible materials red, orange or yellow. The invention also provides compositions and methods for coloring edible materials to a desired color such as red, orange or yellow.

8 Claims, 75 Drawing Sheets

(56) References Cited

U.S. PATENT DOCUMENTS

| | | |
|---|---|---|
| 8,784,853 B2 | 7/2014 | Wagner et al. |
| 2007/0178216 A1 | 8/2007 | Kandaswami |

FOREIGN PATENT DOCUMENTS

| | | |
|---|---|---|
| WO | 2010134595 A1 | 11/2010 |
| WO | 2011048011 A2 | 4/2011 |
| WO | 2017079564 | 5/2017 |

OTHER PUBLICATIONS ir.knust.edu.gh/bitstream/123456789/235/1/Oenewaa%20Korankye.pdf accessed Jun. 2019; Korankye, O Graduate thesis, posted Jun. 15, 2010; (Year: 2010).*

Tanaka et al., Proceedings of the 2001 International Conference on 0-cha (tea) Culture and Science, 2001, Session II, pp. 276-279.

Das et al., "Dyeing of Wool and Silk with Tea", International Journal of Tea Science, 2005, 4:17-25.

Cheung et al., "Aromatic Saddles Containing Two Heptagons", 2015, J Am Chem Soc, 137:3910-3914.

Dabas, 2012, Ph.D. Thesis, "A Colored Avocado Seed Extract With Antioxidant, Anti-Carcinogenic and Anti-Inflammatory Effects" The Pennsylvania State University; pp. 1-142.

Horner et al., "Zur elektrophilen Substitution des Benzocyclobutens", 1960, Eur J Inorg Chem 93:1774-1781.

Leite et al., "Chemical composition, toxicity and larvicidal and antifungal activities of *Persea americana* (avocado) seed extracts", 2009, Rev Soc Bras Med Trop 42:110-113.

Kahn, Varda. "Characterization of Starch Isolated from Avocado Seeds", 1987, J Food Sci 52:1646-1648.

Evans et al., "Pigment production from immobilized*Monascus* sp utilizing polymeric resin adsorption", 1984, Appl Environ Microbiol 47:1323-1326.

Lea, Andrew. "Flavor, Color, and Stability in Fruit Products: The Effect of Polyphenols", 1992, Chapter in Plant Polyphenols, pp. 827-847.

Menet et al., "Analysis of Theaflavins and Thearubigins from Black Tea Extract by MALDI-TOF Mass Spectrometry", 2004, J Agric Food Chem 52(9):2455-2461.

Ginda et al., "Salviolone, a cytotoxic bisnorditerpene with a benzotropolone chromophore from a chinese drug dan-shen (*Salvia miltiorrhiza*)", 1988, Tetrahedron 29:4603-4606.

Kerschensteiner et al., "Crocipodin, a benzotropolone pigment from the mushroom *Leccinum crocipodium* (Boletales)", 2011, Tetrahedron 67:1536-1539.

Remias et al., "Characterization of an UV- and VIS-absorbing, purpurogallin-derived secondary pigment new to algae and highly abundant in *Mesotaenium berggrenii* (Zygnematophyceae, Chlorophyta), an extremophyte living on glaciers", 2012, FEMS Microbiol Ecol 79:638-648.

Dabas et al., "A Colored Avocado Seed Extract as a PotentialNatural Colorant", 2011. J. Food Sci 76:C1335-1341.

Deniz Arican et al. "Syntheses of 3,4-Benzotropolones by Ring-Closing Metatheses", 2013, Organic Letters 15:2582-2585.

R. Munday et al. "Synthesis of Compounds Related to Cyclohepta[def-]fluorene", 1969, Journal of the Chemical Society C: Organic, 10:1427-1434.

Shin-Ichi Naya et al. "Synthesis, Properties, and Oxidizing Ability of Areno-Annulated 1,3-Dimethyl-10-phenylcyclohepta[4,5]pyrrolo[2,3-d]pyrimidine-2,4(1,3 H)-dionylium Ions", 2006, Journal of Organic Chemistry 71:176-184.

PubChem CID 11050, Mar. 26, 2005, pp. 1-20.

PubChem CID 12322926, Feb. 7, 2007, pp. 1-5.

\* cited by examiner

COMPOUNDS, COMPOSITIONS AND METHODS FOR COLORING EDIBLE MATERIALS

CROSS-REFERENCE TO RELATED APPLICATIONS

The present application claims priority to U.S. Provisional Application No. 62/250,684, filed Nov. 4, 2015, which is hereby incorporated by reference in its entirety herein.

REFERENCE TO GOVERNMENT GRANT

This invention was made with government support under Grant No. PEN04565, awarded by The United States Department of Agriculture Hatch Act and under Grant No. AT004678, awarded by the National Institutes of Health. The Government has certain rights in the invention.

BACKGROUND OF THE INVENTION

The global natural and synthetic food color market is estimated to reach US $ 2.3 billion by 2019, with North America dominating the market, followed closely by Europe. This figure reflects the ubiquitous application of added food colorants throughout the world. Though the use of added food colorants has continued to grow, consumers have become increasingly concerned by the perceived negative health risks which may be associated with artificial food colors. This change in consumer desire can be seen by the change in the global food colors market, as natural food colors have begun to dominate the market, increasing from 54.9% in 2014 to a predicted 60% by 2020, with particular interest in those compounds responsible for yellow, orange, red, and pink colors. Despite the fact that consumers are beginning to show preference for natural food colors over those not found in nature, it cannot be overstated that being of natural origin, i.e. being produced by a living organism, does not signify that the consumption of such compounds is safe.

In humans, food color is irrefutably linked to their perception of food safety and flavor (Garber et al., 2000, J Mark Theory Pract 8:59-72) and has a direct connection with human's sensory perception of foods. This can be both a help and a hindrance when it comes to marketing new food products. While vibrant novel colors catch the attention of consumers, it tends to only be helpful in the case nondescript flavors (Garber et al., 2000, J Mark Theory Pract 8:59-72).

Artificial colorants are those pigments which have been fully discovered and synthesized in the laboratory, and are not of natural origin. Artificial colorants are generally vibrant have continued to gain popularity due to their increased stability under a variety of heat, light, time, and other storage conditions. Although there is a standard to what colors are allowable in food, the data on the long term effects of these compounds is limited, as is knowledge as to what dose is actually consumed by individuals on a regular basis. Still, the use of artificial colorants in the United States has increased 5 fold from 5 mg/capita/day in 1950 to 68 mg/capita/day in 2012 (Stevens et al., 2014, T Clin Pediatr 53:133-40). Currently, the Food and Drug Administration's (FDA) website lists thirteen certified FD&C colors and lakes permanently listed for use in food.

A natural colorant can be defined as any pigment which is produced by any organism such as a plant, animal, fungi, or microorganism (Lunning et al., 2007, In *Food Colorants: Chemical and Functional Properties* p 557). In its use in a food, a natural colorant can either be extracted from its natural source, such as in the case of safranal from saffron, or after discovery can be synthesized in a laboratory for use, as is commonly done with β-carotene found in carrots. The general perception of consumers is that natural food colorants are innately safer than their artificial counterparts. It is true that many natural colorants offer a variety of health benefits mainly due to their antioxidant properties. However, the dose of any compound to be consumed must always be taken into consideration.

Polyphenol oxidases (PPO) are enzymes (EC 1.14.18.1) found almost universally in all varieties of organisms including bacteria, insects, crustaceans, mammals, fungi, and plants (Mayer, 2006, Photochemistry: 67:2318-31). They are divided into the two subclasses of tyrosinases and laccases. PPO contributes to the production of the brown pigment melanin in mammals and in plants it is responsible for the browning which occurs when the flesh of a fruit or vegetable is sliced or bruised in the presence of oxygen.

Due to the increasing interest in natural colorants, there is now much focus turning to their production, and specifically PPO colorants. One particular class of pigment compounds is benzotropolones. Benzotropolones are characterized by a seven-membered tropolone ring attached to a six-membered aromatic ring and have been found throughout nature in mushrooms, black teas, Chinese sage, and *Mesotaenium berggrenii*, an extremophyte living on glaciers (Manet et al., 2004, J Agric Food Chem 52:2455-61; Ginda et al., 1988, Tetrahedron 29:4603-6; Kerschensteiner et al., 2011, Tetrahedron 67:1536-9; Remias et al., 2012, FEMS Microbiol Ecol 79:638-48). Benzotropolones are generally yellow, orange, red, or brown in color, although one instance of a "dark solid with green metallic luster" was observed in the case of aurantricholine. Upon addition of base, aurantricholine changed irreversibly to green-black, while upon addition of acid it produced yellow compounds of undetermined structure (Kandaswami et al., 2007 U.S.20070178216). Benzotropolone-glycosides tend to have low solubility in organic solvents and may only be easily dissolved in water, making structure elucidation complex. Another common property of some is that they may be unstable, even at low temperatures or upon standing in organic solvents. Benzotropolones have been reported to have health beneficial properties due to their antioxidant and anti-obesity nature. For example, theaflavins, and their polymerized form, thearubigins, have been reported to aid in weight loss and metabolic syndrome due their ability to decrease appetite, reduce adipose tissue, increase metabolism and energy levels and protect and enhance lean body mass (Kandaswami et al., 2007, U.S.20070178216; Cornelius et al., 2007, U.S.20090098224). Theaflavins have also been shown to be useful in the treatment of alcoholic liver diseases (Li et al, 2014, U.S.20150094364). As the desire for natural alternatives to artificial colorants continues to grow, more research will be needed on the potential positive and negative health effects of these and other benzotropolones.

The avocado (*Persea americana* Mill. Lauraceae) is a large drupe and has the highest oil content of all fruits, with the possible exception of the olive fruit. The avocado seed represents up to 16% of the total weight of the fruit, has a complex phytochemical profile and a long history of ethnobotanical use. Historically, colored exudate from avocado seeds was used as indelible ink by the Conquistadors in the 1500s. When crushed in air, avocado seeds develop a stable orange pigment (Dabas et al., 2011. J. Food Sci 76:C1335-41; Dabas, 2012, Ph.D. Thesis, The Pennsylvania State University). This development of color was dependent on the action of the enzyme polyphenol oxidase, indicating that the resulting pigment is a polyphenolic compound. Further studies are needed to determine the identity of the compounds responsible for the orange color, and their colorant characteristics in various systems.

Thus, there is a need in the art for novel natural colorants. The present invention fulfills this need.

SUMMARY OF THE INVENTION

In one aspect, the invention provides a compound of general formula (A):

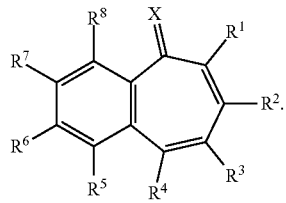

(A)

In one embodiment, in general formula (A), $R^1$ to $R^8$ are each independently selected from the group consisting of hydrogen, alkyl, substituted alkyl, alkenyl, substituted alkenyl, alkynyl, substituted alkynyl, cycloalkyl, substituted cycloalkyl, aryl, substituted aryl, heterocyclyl, substituted heterocyclyl, heteroaryl, substituted heteroaryl, $(C(R^9R^{10}))_n$, $(C(R^9R^{10}))_nOR^{11}$, $(C(R^9R^{10}))_n(NR^{12})R^{11}$, $N(R^9R^{10})$, and $OR^9$, wherein any two of $R^1$ to $R^8$ are optionally joined to form a ring, wherein the ring is optionally substituted;

each occurrence $R^9$ and $R^{10}$ is independently selected from the group consisting of hydrogen, alkyl, substituted alkyl, alkenyl, substituted alkenyl, alkynyl, substituted alkynyl, cycloalkyl, substituted cycloalkyl, aryl, substituted aryl, heterocyclyl, substituted heterocyclyl, heteroaryl, and substituted heteroaryl, wherein $R^9$ and $R^{10}$ are optionally joined to form a ring, wherein the ring is optionally substituted;

each occurrence $R^{11}$ is independently selected from the group consisting of hydrogen, alkyl, substituted alkyl, alkenyl, substituted alkenyl, alkynyl, substituted alkynyl, cycloalkyl, substituted cycloalkyl, aryl, substituted aryl, heterocyclyl, substituted heterocyclyl, heteroaryl, substituted heteroaryl, a monosaccharide, a disaccharide, and a polysaccharide;

each occurrence $R^{12}$ is independently selected from the group consisting of hydrogen alkyl, substituted alkyl, alkenyl, substituted alkenyl, alkynyl, substituted alkynyl, cycloalkyl, substituted cycloalkyl, aryl, substituted aryl, heterocyclyl, substituted heterocyclyl, heteroaryl, and substituted heteroaryl;

each occurrence of n is independently an integer from 0 to 10; and

X is selected from the group consisting of O, NH and S.

In one embodiment, $R^3$ and $R^5$ are joined to form a ring. In one embodiment, $R^1$ is $(C(R^9R^{10}))_nOR^{11}$. In one embodiment, $R^{11}$ is a monosaccharide.

In one embodiment, the compound of general formula (A) is represented by formula (B)

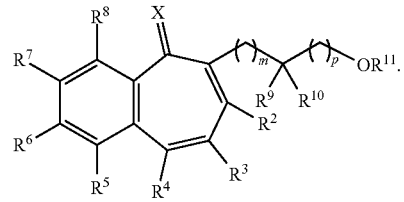

(B)

In one embodiment, in general formula (B), $R^2$ to $R^8$ are each independently selected from the group consisting of hydrogen, alkyl, substituted alkyl, alkenyl, substituted alkenyl, alkynyl, substituted alkynyl, cycloalkyl, substituted cycloalkyl, aryl, substituted aryl, heterocyclyl, substituted heterocyclyl, heteroaryl, substituted heteroaryl, $(C(R^9R^{10}))_n$, $(C(R^9R^{10}))_nOR^{11}$, $(C(R^9R^{10}))_n(NR^{12})R^{11}$, $N(R^9R^{10})$, and $OR^9$, wherein any of $R^1$ to $R^8$ are optionally joined to form a ring, wherein the ring is optionally substituted;

each occurrence $R^9$ and $R^{10}$ is independently selected from the group consisting of hydrogen, alkyl, substituted alkyl, alkenyl, substituted alkenyl, alkynyl, substituted alkynyl, cycloalkyl, substituted cycloalkyl, aryl, substituted aryl, heterocyclyl, substituted heterocyclyl, heteroaryl, and substituted heteroaryl, wherein $R^9$ and $R^{10}$ are optionally joined to form a ring wherein the ring is optionally substituted;

each occurrence $R^{11}$ is independently selected from the group consisting of hydrogen, alkyl, substituted alkyl, alkenyl, substituted alkenyl, alkynyl, substituted alkynyl, cycloalkyl, substituted cycloalkyl, aryl, substituted aryl, heterocyclyl, substituted heterocyclyl, heteroaryl, substituted heteroaryl, a monosaccharide, a disaccharide, and a polysaccharide;

each occurrence $R^{12}$ is independently selected from the group consisting of hydrogen alkyl, substituted alkyl, alkenyl, substituted alkenyl, alkynyl, substituted alkynyl, cycloalkyl, substituted cycloalkyl, aryl, substituted aryl, heterocyclyl, substituted heterocyclyl, heteroaryl, and substituted heteroaryl;

each occurrence of n is independently an integer from 0 to 10;

m is an integer from 1 to 11;

p is an integer from 0 to 5; and

X is selected from the group consisting of O, NH and S.

In one embodiment, the compound of general formula (A) is represented by general formula (C)

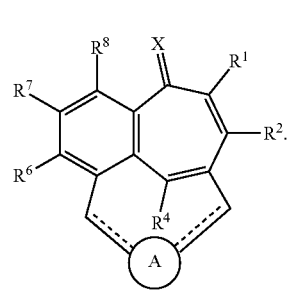

(C)

In one embodiment, in formula (C), $R^1$, $R^2$, $R^4$, and $R^6$-$R^8$ are each independently selected from the group consisting of hydrogen, alkyl, substituted alkyl, alkenyl, substituted alkenyl, alkynyl, substituted alkynyl, cycloalkyl, substituted cycloalkyl, aryl, substituted aryl, heterocyclyl, substituted heterocyclyl, heteroaryl, substituted heteroaryl, $(C(R^9R^{10}))_n$, $(C(R^9R^{10}))_nOR^{11}$, $(C(R^9R^{10}))_n(NR^{12})R^{11}$, $N(R^9R^{10})$, and $OR^9$, wherein any of $R^1$, $R^2$, $R^4$, and $R^6$-$R^8$ are optionally joined to form a ring, wherein the ring is optionally substituted;

each occurrence $R^9$ and $R^{10}$ is independently selected from the group consisting of hydrogen, an alkyl, substituted alkyl, alkenyl, substituted alkenyl, alkynyl, substituted alkynyl, cycloalkyl, substituted cycloalkyl, aryl, substituted aryl, heterocyclyl, substituted heterocyclyl, heteroaryl, and substituted heteroaryl, wherein $R^9$ and $R^{10}$ are optionally joined to form a ring;

each occurrence $R^{11}$ is independently selected from the group consisting of hydrogen, alkyl, substituted alkyl, alkenyl, substituted alkenyl, alkynyl, substituted alkynyl, cycloalkyl, substituted cycloalkyl, aryl, substituted aryl, heterocyclyl, substituted heterocyclyl, heteroaryl, substituted heteroaryl, a monosaccharide, a disaccharide, and a polysaccharide;

each occurrence $R^{12}$ is independently selected from the group consisting of hydrogen, alkyl, substituted alkyl, alkenyl, substituted alkenyl, alkynyl, substituted alkynyl, cycloalkyl, substituted cycloalkyl, aryl, substituted aryl, heterocyclyl, substituted heterocyclyl, heteroaryl, and substituted heteroaryl;

each occurrence of n is independently an integer from 0 to 10;

X is selected from the group consisting of O, NH and S; and

A is an optionally substituted 3 to 10 membered ring.

In one embodiment, the compound is

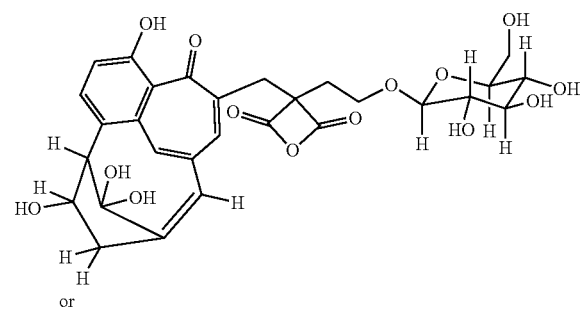

or

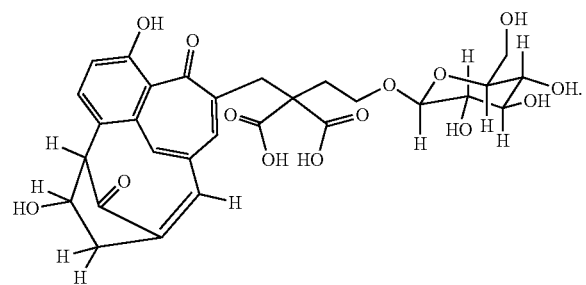

In one embodiment, the compound is a hue selected from the group consisting of yellow, orange and red.

In another aspect, the invention provides an edible material comprising a compound of the invention. In one embodiment, the edible material has a hue selected from the group consisting of orange, red and yellow.

In another aspect, the invention provides a method of coloring an edible material, the method comprising adding to the edible material a compound of the invention.

In another aspect, the invention provides a compound prepared by a process comprising the steps of: obtaining a seed of *Persea americana*; grounding the seed to a slurry; incubating the powder; extracting the compound by incubating the powder with an alcohol to form a first mixture; isolating a first liquid from the first mixture; removing the starch from the first liquid; precipitating an impurity in the liquid to form a second mixture; isolating a second liquid from the second mixture; precipitating an insoluble material from the second mixture to form a third mixture; isolating a third liquid from the third mixture; adsorbing the third liquid to a resin; and isolating the compound by eluting the compound from the resin with an alcohol.

In one embodiment, the alcohol is methanol, ethanol, acetone, citric acid, acetic acid, or any combination thereof. In one embodiment, the resin is a XAD-7 resin.

In yet another aspect, the invention provides a method of imparting a color to a substrate. In one embodiment the method comprises applying a compound of the invention to the substrate. In one embodiment, color is selected from the group consisting of red, yellow and orange. In one embodiment, the substrate is an edible material

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIGS. 3A and 3B, depicts results of experimental examples demonstrating the color of semi-pure CASE in white cake. FIG. 3A depicts the tops of the cupcakes. FIG. 3B depicts the middles of the cupcakes. Concentration of CASE is shown in mg/mL.

FIG. 5, comprising FIG. 3A depicts the color of dry cheese powders. FIG. 3B depicts the color of prepared cheese sauce.

FIG. 7, comprising FIG. 7A depicts the change of lighted samples at 26° C. FIG. 7B depicts the change of samples kept in the dark at 4° C.

FIG. 7C depicts the change of samples kept in the dark 23° C. FIG. 7D depicts the change of samples kept in the dark 40° C.

FIG. 9, comprising FIG. 9A depicts the change of lighted samples at 26° C. FIG. 9B depicts the change of samples kept in the dark at 4° C.

FIG. 9C depicts the change of samples kept in the dark 23° C. FIG. 9D depicts the change of samples kept in the dark 40° C.

FIG. 10, comprising FIG. 10A depicts the color of pretreatment samples. FIG. 10B depicts the color of pH adjusted samples. FIG. 10C depicts the color of samples where the pH returned to acidic conditions.

DETAILED DESCRIPTION OF THE INVENTION

Figure 1:
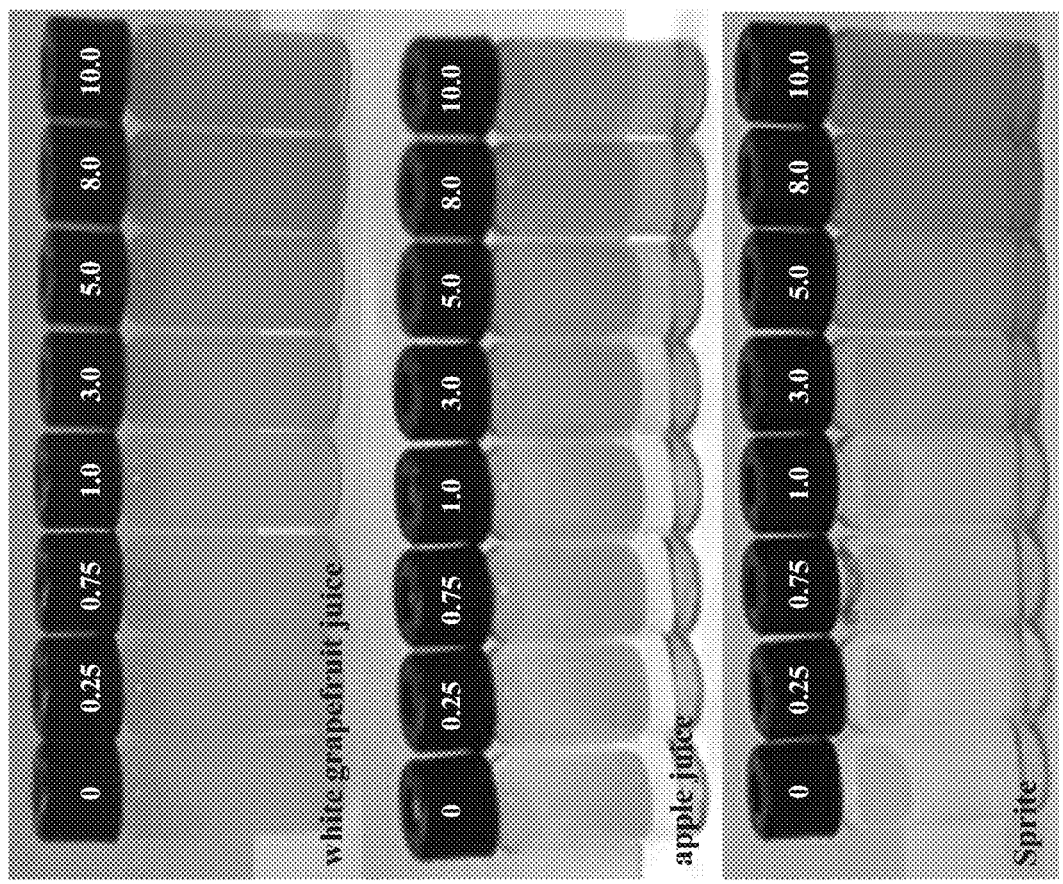
FIG. 1 depicts results of experimental examples demonstrating the color of semi-pure colored avocado seed extract (CASE) in white grapefruit juice, apple juice, and Sprite. Concentration of semi-pure CASE used is shown above each sample in the units of mg/mL.

This invention relates to the unexpected identification of novel compounds isolated from colored avocado seed extract and their utility as source of natural colorants. In some aspects the compounds may be used as an orange colorant. In another embodiment, the compounds may be used as a yellow colorant. In yet another embodiment, the compounds may be used as a red colorant. However, the invention should not be limited to only these colors. Rather, the invention includes any desired color that is associated with one or more of hues yellow, orange, and red. In one embodiment, the invention includes any color in the spectrum for yellow, orange, and red. In one embodiment, the invention includes any color that contains one or more of yellow, orange, and red.

DEFINITIONS

As used herein, each of the following terms has the meaning associated with it in this section.

Unless defined otherwise, all technical and scientific terms used herein generally have the same meaning as commonly understood by one of ordinary skill in the art to which this invention belongs. Generally, the nomenclature used herein and the laboratory procedures in biochemistry, analytical chemistry and organic chemistry are those well-known and commonly employed in the art. Standard techniques or modifications thereof are used for chemical syntheses and chemical analyses.

The articles "a" and "an" are used herein to refer to one or to more than one (i.e. to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.10% from the specified value, as such variations are appropriate to perform the disclosed methods.

As used herein, the term "benzotropolone" refers to a seven-membered tropolone ring attached to a six-membered aromatic ring.

As used herein, the term colored avocado seed extract (CASE), perseoranjin, F12, and Avocolor are used to describe a composition for coloring food which is isolated from an Avocado seed using a method of the invention. In one embodiment, CASE, perseoranjin, F12, and Avocolor comprise a compound of the invention.

In one embodiment, compounds of the invention contain saccharides. "Saccharides" as used herein, include, but are not limited to aldose or ketose pentosyl or hexosyl sugars selected from the group consisting of D- and L-enantiomers of ribose, glucose, galactose, mannose, arabinose, allose, altrose, gulose, idose, talose and their substituted derivatives. Most preferably, the subject sugar comprises an aldose pentosyl or hexosyl sugar selected from ribose, glucose, galactose, glucosamine, galactosamine, N-acetylglucosamine, N-acetylgalactosamine, N-acetyl ribosamine, xylose, mannose and arabinose.

"Di-saccharide", when used in regard to the subject sugar residue, is intended to mean a polymeric assemblage of 2 sugar residues. Representative examples of disaccharides include homo-polymeric (e.g., maltose and cellobiose) and hetero-polymeric (e.g., lactose and sucrose) assemblages of sugars as set forth supra.

"Tri-saccharide", when used in regard to the subject sugar residue, is intended to mean a polymeric assemblage of 3 sugar residues.

"Polysaccharide", when used in regard to the subject sugar residue, is intended to mean a polymeric assemblage of 3 or more sugar residues.

An "effective amount" of a delivery vehicle is that amount sufficient to effectively bind or deliver a compound.

The term "compound," as used herein, unless otherwise indicated, refers to any specific chemical compound disclosed herein. In one embodiment, the term also refers to stereoisomers and/or optical isomers (including racemic mixtures) or enantiomerically enriched mixtures of disclosed compounds.

As used herein, the term "alkyl," by itself or as part of another substituent means, unless otherwise stated, a straight or branched chain hydrocarbon having the number of carbon atoms designated (i.e. $C_{1-6}$ means one to six carbon atoms) and including straight, branched chain, or cyclic substituent groups. Examples include methyl, ethyl, propyl, isopropyl, butyl, isobutyl, tert-butyl, pentyl, neopentyl, hexyl, and cyclopropylmethyl. Most preferred is ($C_1$-$C_6$)alkyl, particularly ethyl, methyl, isopropyl, isobutyl, n-pentyl, n-hexyl and cyclopropylmethyl.

As used herein, the term "alkenyl," employed alone or in combination with other terms, means, unless otherwise stated, a stable mono-unsaturated, di-unsaturated, or poly-unsaturated straight chain or branched chain hydrocarbon group having the stated number of carbon atoms. Examples include vinyl, propenyl (or allyl), crotyl, isopentenyl, butadienyl, 1,3-pentadienyl, 1,4-pentadienyl, and the higher homologs and isomers. A functional group representing an alkene may be exemplified by —$CH_2$—CH=$CH_2$.

As used herein, the term "alkynyl," employed alone or in combination with other terms, means, unless otherwise stated, a stable straight chain or branched chain hydrocarbon group with a triple carbon-carbon bond, having the stated number of carbon atoms. Non-limiting examples include ethynyl and propynyl, and the higher homologs and isomers. The term "propargylic" refers to a group exemplified by —CH$_2$—C≡CH. The term "homopropargylic" refers to a group exemplified by —CH$_2$CH$_2$—C≡CH. The term "substituted propargylic" refers to a group exemplified by —CR$_2$—C≡CR, wherein each occurrence of R is independently H, alkyl, substituted alkyl, alkenyl or substituted alkenyl, with the proviso that at least one R group is not hydrogen. The term "substituted homopropargylic" refers to a group exemplified by —CR$_2$CR$_2$—C≡CR, wherein each occurrence of R is independently H, alkyl, substituted alkyl, alkenyl or substituted alkenyl, with the proviso that at least one R group is not hydrogen.

As used herein, the term "substituted alkyl," "substituted cycloalkyl," "substituted alkenyl" or "substituted alkynyl" means alkyl cycloalkyl, alkenyl or alkynyl, as defined above, substituted by one, two or three substituents selected from the group consisting of halogen, —OH, alkoxy, —NH$_2$, —N(CH$_3$)$_2$, —C(=O), —C(=O)OH, trifluoromethyl, —C≡N, —C(=O)O(C$_1$-C$_4$)alkyl, —C(=O)NH$_2$, —SO$_2$NH$_2$, —C(=NH)NH$_2$, and —NO$_2$, preferably containing one or two substituents selected from halogen, —OH, alkoxy, —NH$_2$, trifluoromethyl, —N(CH$_3$)$_2$, and —C(=O)OH, more preferably selected from halogen, alkoxy and —OH. Examples of substituted alkyls include, but are not limited to, 2,2-difluoropropyl, 2-carboxycyclopentyl and 3-chloropropyl.

As used herein, the term "heteroalkyl" by itself or in combination with another term means, unless otherwise stated, a stable straight or branched chain alkyl group consisting of the stated number of carbon atoms and one or two heteroatoms selected from the group consisting of O, N, and S, and wherein the nitrogen and sulfur atoms may be optionally oxidized and the nitrogen heteroatom may be optionally quaternized. The heteroatom(s) may be placed at any position of the heteroalkyl group, including between the rest of the heteroalkyl group and the fragment to which it is attached, as well as attached to the most distal carbon atom in the heteroalkyl group. Examples include: —O—CH$_2$—CH$_2$—CH$_3$, —CH$_2$—CH$_2$—CH$_2$—OH, —CH$_2$—CH$_2$—NH—CH$_3$, —CH$_2$—S—CH$_2$—CH$_3$, and —CH$_2$CH$_2$—S(=O)—CH$_3$. Up to two heteroatoms may be consecutive, such as, for example, —CH$_2$—NH—OCH$_3$, or —CH$_2$—CH$_2$—S—S—CH$_3$ As used herein, the term "alkoxy" employed alone or in combination with other terms means, unless otherwise stated, an alkyl group having the designated number of carbon atoms, as defined above, connected to the rest of the molecule via an oxygen atom, such as, for example, methoxy, ethoxy, 1-propoxy, 2-propoxy (isopropoxy) and the higher homologs and isomers. Preferred are (C$_1$-C$_3$) alkoxy, particularly ethoxy and methoxy.

As used herein, the term "halo" or "halogen" alone or as part of another substituent means, unless otherwise stated, a fluorine, chlorine, bromine, or iodine atom, preferably, fluorine, chlorine, or bromine, more preferably, fluorine or chlorine.

As used herein, the term "cycloalkyl" refers to a mono cyclic or polycyclic non-aromatic radical, wherein each of the atoms forming the ring (i.e. skeletal atoms) is a carbon atom. In one embodiment, the cycloalkyl group is saturated or partially unsaturated. In another embodiment, the cycloalkyl group is fused with an aromatic ring. Cycloalkyl groups include groups having from 3 to 10 ring atoms. Illustrative examples of cycloalkyl groups include, but are not limited to, the following moieties:

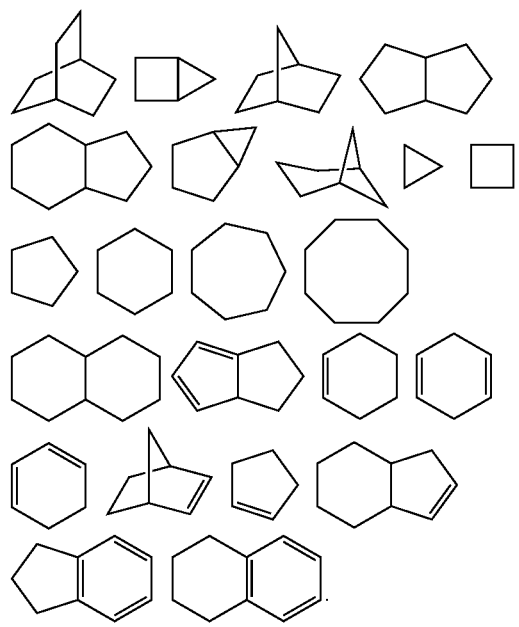

Monocyclic cycloalkyls include, but are not limited to, cyclopropyl, cyclobutyl, cyclopentyl, cyclohexyl, cycloheptyl, and cyclooctyl. Dicyclic cycloalkyls include, but are not limited to, tetrahydronaphthyl, indanyl, and tetrahydropentalene.

Polycyclic cycloalkyls include adamantine and norbornane. The term cycloalkyl includes "unsaturated nonaromatic carbocyclyl" or "nonaromatic unsaturated carbocyclyl" groups, both of which refer to a nonaromatic carbocycle as defined herein, which contains at least one carbon carbon double bond or one carbon carbon triple bond.

As used herein, the term "heterocycloalkyl" or "heterocyclyl" refers to a heteroalicyclic group containing one to four ring heteroatoms each selected from O, S and N. In one embodiment, each heterocycloalkyl group has from 4 to 10 atoms in its ring system, with the proviso that the ring of said group does not contain two adjacent O or S atoms. In another embodiment, the heterocycloalkyl group is fused with an aromatic ring. In one embodiment, the nitrogen and sulfur heteroatoms may be optionally oxidized, and the nitrogen atom may be optionally quaternized. The heterocyclic system may be attached, unless otherwise stated, at any heteroatom or carbon atom that affords a stable structure. A heterocycle may be aromatic or non-aromatic in nature. In one embodiment, the heterocycle is a heteroaryl.

An example of a 3-membered heterocycloalkyl group includes, and is not limited to, aziridine. Examples of 4-membered heterocycloalkyl groups include, and are not limited to, azetidine and a beta lactam. Examples of 5-membered heterocycloalkyl groups include, and are not limited to, pyrrolidine, oxazolidine and thiazolidinedione. Examples of 6-membered heterocycloalkyl groups include, and are not limited to, piperidine, morpholine and piperazine. Other non-limiting examples of heterocycloalkyl groups are:

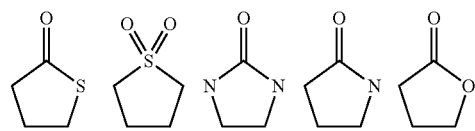

-continued

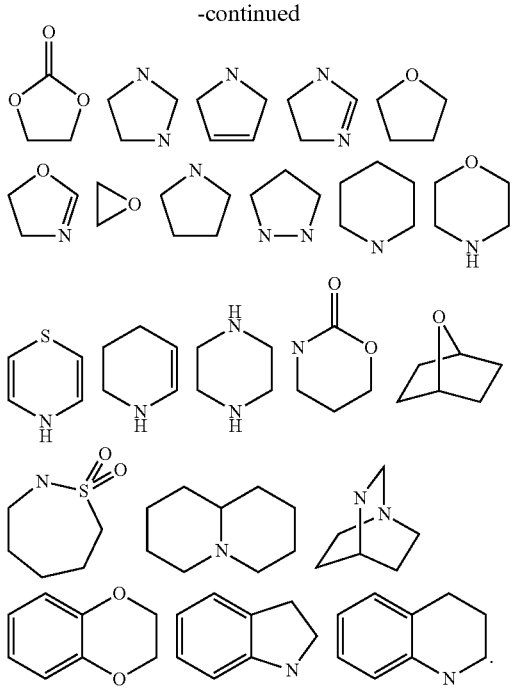

Examples of non-aromatic heterocycles include monocyclic groups such as aziridine, oxirane, thiirane, azetidine, oxetane, thietane, pyrrolidine, pyrroline, pyrazolidine, imidazoline, dioxolane, sulfolane, 2,3-dihydrofuran, 2,5-dihydrofuran, tetrahydrofuran, thiophane, piperidine, 1,2,3,6-tetrahydropyridine, 1,4-dihydropyridine, piperazine, morpholine, thiomorpholine, pyran, 2,3-dihydropyran, tetrahydropyran, 1,4-dioxane, 1,3-dioxane, homopiperazine, homopiperidine, 1,3-dioxepane, 4,7-dihydro-1,3-dioxepin, and hexamethyleneoxide.

As used herein, the term "aromatic" refers to a carbocycle or heterocycle with one or more polyunsaturated rings and having aromatic character, i.e. having (4n+2) delocalized 2n (pi) electrons, where n is an integer.

As used herein, the term "aryl," employed alone or in combination with other terms, means, unless otherwise stated, a carbocyclic aromatic system containing one or more rings (typically one, two or three rings), wherein such rings may be attached together in a pendent manner, such as a biphenyl, or may be fused, such as naphthalene. Examples of aryl groups include phenyl, anthracyl, and naphthyl. Preferred examples are phenyl and naphthyl, most preferred is phenyl.

As used herein, the term "aryl-($C_1$-$C_3$)alkyl" means a functional group wherein a one- to three-carbon alkylene chain is attached to an aryl group, e.g., —$CH_2CH_2$-phenyl. Preferred is aryl-$CH_2$— and aryl-$CH(CH_3)$—. The term "substituted aryl-($C_1$-$C_3$)alkyl" means an aryl-($C_1$-$C_3$)alkyl functional group in which the aryl group is substituted. Preferred is substituted aryl($CH_2$)—. Similarly, the term "heteroaryl-($C_1$-$C_3$)alkyl" means a functional group wherein a one to three carbon alkylene chain is attached to a heteroaryl group, e.g., —$CH_2CH_2$-pyridyl. Preferred is heteroaryl-($CH_2$)—. The term "substituted heteroaryl-($C_1$-$C_3$) alkyl" means a heteroaryl-($C_1$-$C_3$)alkyl functional group in which the heteroaryl group is substituted. Preferred is substituted heteroaryl-($CH_2$)—.

As used herein, the term "heteroaryl" or "heteroaromatic" refers to a heterocycle having aromatic character. A polycyclic heteroaryl may include one or more rings that are partially saturated. Examples include the following moieties:

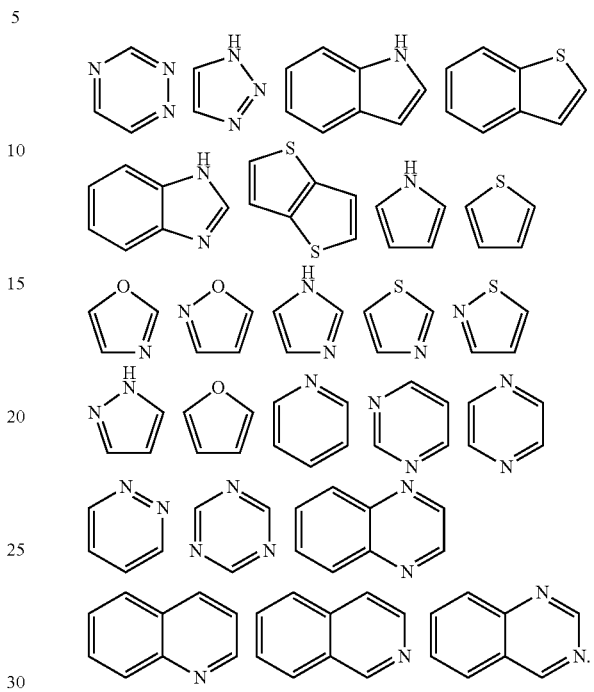

Examples of heteroaryl groups also include pyridyl, pyrazinyl, pyrimidinyl (particularly 2- and 4-pyrimidinyl), pyridazinyl, thienyl, furyl, pyrrolyl (particularly 2-pyrrolyl), imidazolyl, thiazolyl, oxazolyl, pyrazolyl (particularly 3- and 5-pyrazolyl), isothiazolyl, 1,2,3-triazolyl, 1,2,4-triazolyl, 1,3,4-triazolyl, tetrazolyl, 1,2,3-thiadiazolyl, 1,2,3-oxadiazolyl, 1,3,4-thiadiazolyl and 1,3,4-oxadiazolyl.

Examples of polycyclic heterocycles and heteroaryls include indolyl (particularly 3-, 4-, 5-, 6- and 7-indolyl), indolinyl, quinolyl, tetrahydroquinolyl, isoquinolyl (particularly 1- and 5-isoquinolyl), 1,2,3,4-tetrahydroisoquinolyl, cinnolinyl, quinoxalinyl (particularly 2- and 5-quinoxalinyl), quinazolinyl, phthalazinyl, 1,8-naphthyridinyl, 1,4-benzodioxanyl, coumarin, dihydrocoumarin, 1,5-naphthyridinyl, benzofuryl (particularly 3-, 4-, 5-, 6- and 7-benzofuryl), 2,3-dihydrobenzofuryl, 1,2-benzisoxazolyl, benzothienyl (particularly 3-, 4-, 5-, 6-, and 7-benzothienyl), benzoxazolyl, benzothiazolyl (particularly 2-benzothiazolyl and 5-benzothiazolyl), purinyl, benzimidazolyl (particularly 2-benzimidazolyl), benzotriazolyl, thioxanthinyl, carbazolyl, carbolinyl, acridinyl, pyrrolizidinyl, and quinolizidinyl.

As used herein, the term "substituted" means that an atom or group of atoms has replaced hydrogen as the substituent attached to another group. The term "substituted" further refers to any level of substitution, namely mono-, di-, tri-, tetra-, or penta-substitution, where such substitution is permitted. The substituents are independently selected, and substitution may be at any chemically accessible position. In one embodiment, the substituents vary in number between one and four. In another embodiment, the substituents vary in number between one and three. In yet another embodiment, the substituents vary in number between one and two.

As used herein, the term "optionally substituted" means that the referenced group may be substituted or unsubstituted. In one embodiment, the referenced group is optionally substituted with zero substituents, i.e., the referenced group is unsubstituted. In another embodiment, the referenced group is optionally substituted with one or more additional group(s) individually and independently selected from groups described herein.

In one embodiment, the substituents are independently selected from the group consisting of oxo, halogen, —CN, —NH$_2$, —OH, —NH(CH$_3$), —N(CH$_3$)$_2$, alkyl (including straight chain, branched and/or unsaturated alkyl), substituted or unsubstituted cycloalkyl, substituted or unsubstituted heterocycloalkyl, fluoro alkyl, substituted or unsubstituted heteroalkyl, substituted or unsubstituted alkoxy, fluoroalkoxy, —S-alkyl, S(=O)$_2$alkyl, —C(=O)NH[substituted or unsubstituted alkyl, or substituted or unsubstituted phenyl], —C(=O)N[H or alkyl]$_2$, —OC(=O)N[substituted or unsubstituted alkyl]$_2$, —NHC(=O)NH [substituted or unsubstituted alkyl, or substituted or unsubstituted phenyl], —NHC(=O)alkyl, —N[substituted or unsubstituted alkyl]C(=O)[substituted or unsubstituted alkyl], —NHC(=O)[substituted or unsubstituted alkyl], —C(OH)[substituted or unsubstituted alkyl]$_2$, and —C(NH$_2$)[substituted or unsubstituted alkyl]$_2$. In another embodiment, by way of example, an optional substituent is selected from oxo, fluorine, chlorine, bromine, iodine, —CN, —NH$_2$, —OH, —NH(CH$_3$), —N(CH$_3$)$_2$, —CH$_3$, —CH$_2$CH$_3$, —CH(CH$_3$)$_2$, —CF$_3$, —CH$_2$CF$_3$, —OCH$_3$, —OCH$_2$CH$_3$, —OCH(CH$_3$)$_2$, —OCF$_3$, —OCH$_2$CF$_3$, —S(=O)$_2$—CH$_3$, —C(=O)NH$_2$, —C(=O)—NHCH$_3$, —NHC(=O)NHCH$_3$, —C(=O)CH$_3$, and —C(=O)OH. In yet one embodiment, the substituents are independently selected from the group consisting of C$_{1-6}$ alkyl, —OH, C$_{1-6}$ alkoxy, halo, amino, acetamido, oxo and nitro. In yet another embodiment, the substituents are independently selected from the group consisting of C$_{1-6}$ alkyl, C$_{1-6}$ alkoxy, halo, acetamido, and nitro. As used herein, where a substituent is an alkyl or alkoxy group, the carbon chain may be branched, straight or cyclic, with straight being preferred.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

DESCRIPTION

The invention is partly based on the successful production of a semi-pure extract containing a compound of interest that has been tested in food applications including beverages, confectionery, dry mixes, bake goods, and the like. Accordingly, the invention provides compositions and methods of using a compound as a natural food colorant. In another embodiment, the compound of the invention can be used in cosmetic settings. In one embodiment, the compound of the invention provides an advantage to existing food colorants in the art. For example, the compound of the invention is significantly more stable to heat, light, and oxygen, more vibrant, and less toxic.

Compounds

The compounds of the present invention may be synthesized using techniques well-known in the art of organic synthesis. The starting materials and intermediates required for the synthesis may be obtained from commercial sources or synthesized according to methods known to those skilled in the art.

Alternatively, the compounds of the present invention may be isolated from avocado seed extract. Thus, the present invention provides a method for isolating compounds from avocado seed extract. In one embodiment, the method comprises blending avocado seeds, filtering the supernatant, lyophilizing the filtered supernatant, performing a first purification using flash chromatography, performing a second purification using an HPLC C18 column, eluting with a gradient of acetic acid and acetonitrile, performing a third purification using an HPLC Ultra Aromax column, eluting with a gradient of acetic acid and methanol, and obtaining an isolated compound In one embodiment, the invention is a benzotropolone or a benzotropolone derivative. In one embodiment, the benzotropolone is substituted with a sugar group. In one embodiment, the benzotropolone is substituted with an alkoxy-sugar group. In one embodiment, the benzotropolone is substituted with a monosaccharide. In one embodiment, the benzotropolone is substituted with a disaccharide. In one embodiment, the benzotropolone is substituted with a trisaccharide.

In one embodiment, the invention is a compound of general formula (A):

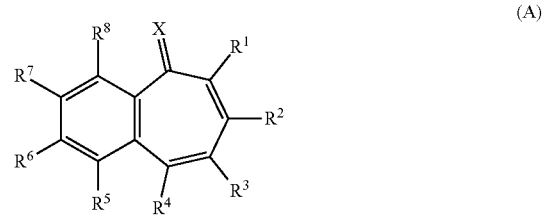

(A)

wherein in general formula (A), $R^1$ to $R^8$ are each independently selected from the group consisting of hydrogen, alkyl, substituted alkyl, alkenyl, substituted alkenyl, alkynyl, substituted alkynyl, cycloalkyl, substituted cycloalkyl, aryl, substituted aryl, heterocyclyl, substituted heterocyclyl, heteroaryl, substituted heteroaryl, (C(R$^9$R$^{10}$))$_n$, (C(R$^9$R$^{10}$))$_n$OR$^{11}$, (C(R$^9$R$^{10}$))$_n$(NR$^{12}$)R$^{11}$, N(R$^9$R$^{10}$), and OR$^9$, wherein any two of R$^1$ to R$^8$ are optionally joined to form a ring, wherein the ring is optionally substituted;

each occurrence R$^9$ and R$^{10}$ is independently selected from the group consisting of hydrogen, alkyl, substituted alkyl, alkenyl, substituted alkenyl, alkynyl, substituted alkynyl, cycloalkyl, substituted cycloalkyl, aryl, substituted aryl, heterocyclyl, substituted heterocyclyl, heteroaryl, and substituted heteroaryl, wherein R$^9$ and R$^{10}$ are optionally joined to form a ring, wherein the ring is optionally substituted;

each occurrence R$^{11}$ is independently selected from the group consisting of hydrogen, alkyl, substituted alkyl, alkenyl, substituted alkenyl, alkynyl, substituted alkynyl, cycloalkyl, substituted cycloalkyl, aryl, substituted aryl, heterocyclyl, substituted heterocyclyl, heteroaryl, substituted heteroaryl, a monosaccharide, a disaccharide, and a polysaccharide;

each occurrence $R^{12}$ is independently selected from the group consisting of hydrogen alkyl, substituted alkyl, alkenyl, substituted alkenyl, alkynyl, substituted alkynyl, cycloalkyl, substituted cycloalkyl, aryl, substituted aryl, heterocyclyl, substituted heterocyclyl, heteroaryl, and substituted heteroaryl;

each occurrence of n is independently an integer from 0 to 10; and

X is selected from the group consisting of O, NH and S.

In one embodiment, $R^3$ and $R^5$ are joined to form a ring, wherein the ring is optionally substituted. In one embodiment, the ring formed by $R^3$ and $R^5$ is a bicyclic ring. In one embodiment the ring is a five membered ring. In one embodiment, the ring is a six membered ring. In one embodiment, the ring is a seven membered ring. In one embodiment, the ring comprises a heteroatom. In one embodiment, the ring is a hydrocarbon ring.

In one embodiment $R^8$ is hydroxyl.

In one embodiment X is O.

In one embodiment, $R^1$ is $(C(R^9R^{10}))_nOR^{11}$. In one embodiment, $R^1$ is $(CH_2)(C\ R^9R^{10})(CH_2)_2OR^{11}$. In one embodiment, $R^9$ is $C(=O)OH$. In one embodiment, $R^{10}$ is $C(=O)OH$. In one embodiment $R^9$ and $R^{10}$ are joined to form a ring. In one embodiment, the ring comprises an O atom. In one embodiment, the ring comprises one or more carbonyls. In one embodiment, the ring is a 3, 4 or 5 membered ring. In one embodiment $R^1$ is a monosaccharide. In one embodiment, $R^{11}$ is glucose, fructose or galactose.

In one embodiment the compound of general formula (A) is a compound of general formula (B):

The compound of claim 1, wherein general formula (A) is represented by general formula (B)

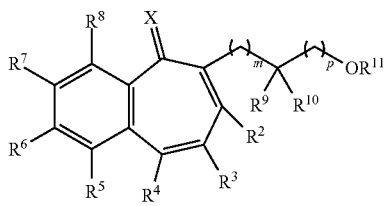

(B)

wherein, in general formula (B), $R^2$ to $R^8$ are each independently selected from the group consisting of hydrogen, alkyl, substituted alkyl, alkenyl, substituted alkenyl, alkynyl, substituted alkynyl, cycloalkyl, substituted cycloalkyl, aryl, substituted aryl, heterocyclyl, substituted heterocyclyl, heteroaryl, substituted heteroaryl, $(C(R^9R^{10}))_n$, $(C(R^9R^{10}))_nOR^{11}$, $(C(R^9R^{10}))_n(NR^{12})R^{11}$, $N(R^9R^{10})$, and $OR^9$, wherein any of $R^1$ to $R^8$ are optionally joined to form a ring, wherein the ring is optionally substituted;

each occurrence $R^9$ and $R^{10}$ is independently selected from the group consisting of hydrogen, alkyl, substituted alkyl, alkenyl, substituted alkenyl, alkynyl, substituted alkynyl, cycloalkyl, substituted cycloalkyl, aryl, substituted aryl, heterocyclyl, substituted heterocyclyl, heteroaryl, and substituted heteroaryl, wherein $R^9$ and $R^{10}$ are optionally joined to form a ring wherein the ring is optionally substituted;

each occurrence $R^{11}$ is independently selected from the group consisting of hydrogen, alkyl, substituted alkyl, alkenyl, substituted alkenyl, alkynyl, substituted alkynyl, cycloalkyl, substituted cycloalkyl, aryl, substituted aryl, heterocyclyl, substituted heterocyclyl, heteroaryl, substituted heteroaryl, a monosaccharide, a disaccharide, and a polysaccharide;

each occurrence $R^{12}$ is independently selected from the group consisting of hydrogen alkyl, substituted alkyl, alkenyl, substituted alkenyl, alkynyl, substituted alkynyl, cycloalkyl, substituted cycloalkyl, aryl, substituted aryl, heterocyclyl, substituted heterocyclyl, heteroaryl, and substituted heteroaryl;

each occurrence of n is independently an integer from 0 to 10;

m is an integer from 1 to 11;

p is an integer from 0 to 5; and

X is selected from the group consisting of O, NH and S.

In one embodiment, the compound of general formula (A) is a compound of general formula (C):

The compound of claim 1, wherein general formula (A) is represented by general formula (C)

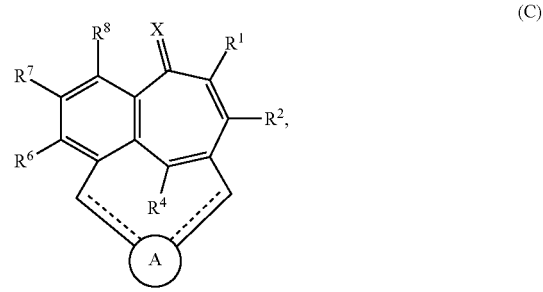

(C)

wherein in general formula (C), $R^1$, $R^2$, $R^4$, and $R^6$-$R^8$ are each independently selected from the group consisting of hydrogen, alkyl, substituted alkyl, alkenyl, substituted alkenyl, alkynyl, substituted alkynyl, cycloalkyl, substituted cycloalkyl, aryl, substituted aryl, heterocyclyl, substituted heterocyclyl, heteroaryl, substituted heteroaryl, $(C(R^9R^{10}))_n$, $(C(R^9R^{10}))_nOR^{11}$, $(C(R^9R^{10}))_n(NR^{12})R^{11}$, $N(R^9R^{10})$, and $OR^9$, wherein any of $R^1$, $R^2$, $R^4$, and $R^6$-$R^8$ are optionally joined to form a ring, wherein the ring is optionally substituted;

each occurrence $R^9$ and $R^{10}$ is independently selected from the group consisting of hydrogen, an alkyl, substituted alkyl, alkenyl, substituted alkenyl, alkynyl, substituted alkynyl, cycloalkyl, substituted cycloalkyl, aryl, substituted aryl, heterocyclyl, substituted heterocyclyl, heteroaryl, and substituted heteroaryl, wherein $R^9$ and $R^{10}$ are optionally joined to form a ring;

each occurrence $R^{11}$ is independently selected from the group consisting of hydrogen, alkyl, substituted alkyl, alkenyl, substituted alkenyl, alkynyl, substituted alkynyl, cycloalkyl, substituted cycloalkyl, aryl, substituted aryl, heterocyclyl, substituted heterocyclyl, heteroaryl, substituted heteroaryl, a monosaccharide, a disaccharide, and a polysaccharide;

each occurrence $R^{12}$ is independently selected from the group consisting of hydrogen, alkyl, substituted alkyl, alkenyl, substituted alkenyl, alkynyl, substituted alkynyl, cycloalkyl, substituted cycloalkyl, aryl, substituted aryl, heterocyclyl, substituted heterocyclyl, heteroaryl, and substituted heteroaryl;

each occurrence of n is independently an integer from 0 to 10;

X is selected from the group consisting of O, NH and S; and

A is an optionally substituted 3 to 10 membered ring.
In one embodiment, the compound is In one embodiment, the compound has a color. In one embodiment, the compound is yellow, orange or red.

In one embodiment, the invention is a compound of general formula (I):

(I)

wherein in general formula (I), $R^1$ is selected from the group consisting of $CH_3$, $CH_2OH$, —C(=O)OH, —C(=NH)OH, —C(=O)$NH_2$, —C(=NH)$NH_2$, —OH, and —$NH_2$;

$R^2$ is selected from the group consisting of H, $CH_3$, OH, —$NH_2$, —C(=O)OH;

$R^3$ is selected from the group consisting of H, $CH_3$, OH, a monosaccharide, a disaccharide, and a polysaccharide;

A is a cycloalkyl ring having from 5 or 6 ring atoms, wherein the cycloalkyl ring may optionally have 0 to 3 double bonds;

each occurrence of $R^4$ is independently selected from the group consisting of H, alkyl, substituted alkyl, alkenyl, aryl, substituted aryl, and OH, wherein two adjacent $R^4$ are optionally joined together to form a ring having 5 to 6 ring atoms, wherein the ring is optionally substituted;

$L^1$ and $L^2$ are each independently selected from the group consisting of a single bond, alkyl, alkenyl, aryl, cycloalkyl, alkylaryl, and alkylcycloalkyl, wherein the alkyl, aryl, cycloalkyl, alkylaryl, or alkylcycloalkyl group is optionally substituted;

each occurrence of X is independently selected from the group consisting of O, NH, and S; and n is an integer from 0 to 6.

In one embodiment, $R^1$ is C(=O)OH.

In one embodiment, $L^1$ is an alkyl. In other embodiments $L^1$ is an alkenyl. In certain embodiments, $L^1$ is selected from the group consisting of —$(CH_2)_{n2}$— and —$(CH=CH)_{n3}$—. In certain embodiments $L^1$ is $CH_2$. In another embodiment $L^1$ is CH=CH. In another embodiment $L^1$ is $(CH=CH)_2$. In yet another embodiment $L^1$ is $(CH=CH)_3$.

In one embodiment, $R^2$ is OH.

In some embodiments $R^3$ is a monosaccharide. In one embodiment, the monosaccharide is glucose. In another embodiment, the monosaccharide is fructose. In yet another embodiment, the monosaccharide is galactose.

In one embodiment $L^2$ is $CH_2$. In another embodiment, $L^2$ is $(CH_2)_2$. In yet another embodiment, $L^2$ is $(CH_2)_3$.

In one embodiment, X is O.

In one embodiment, A is a cycloalkyl ring having 6 ring atoms. In one embodiment the cycloalkyl ring having 6 ring atoms has 1 double bond. In another embodiment, cycloalkyl ring having 6 ring atoms has 2 double bonds. In yet another embodiment, cycloalkyl ring having 6 ring atoms has 3 double bonds.

In one embodiment, $R^4$ is OH. In another embodiment, two adjacent $R^4$ are joined together to form a 5-membered ring, wherein one of the $R^4$ is O. In certain embodiments, n is 2. In another embodiment, n is 3.

In certain embodiments, the compound of general formula (I) is a compound of general formula (II):

(II)

wherein in general formula (II), $R^1$ is selected from the group consisting of $CH_3$, $CH_2OH$, —C(=O)OH, —C(=NH)OH, —C(=O)$NH_2$, —C(=NH)$NH_2$, —OH, and —$NH_2$;

$R^2$ is selected from the group consisting of H, $CH_3$, OH, —$NH_2$, —C(=O)OH;

$R^3$ is selected from the group consisting of H, $CH_3$, OH, a monosaccharide, a disaccharide, and a polysaccharide;

each occurrence of $R^{4a}$, $R^{4b}$, $R^{4c}$, and $R^5$ is independently selected from the group consisting of H, alkyl, substituted alkyl, aryl, substituted aryl, and OH;

$L^1$ is selected from the group consisting of —$(CH_2)_{n2}$— and —$(CH=CH)_{n3}$—;

X is selected from the group consisting of O, NH and S;

$n^1$ is an integer from 0 to 6;

$n^2$ is an integer from 0 to 6, and $n^3$ is an integer from 0 to 3.

In some embodiments, $R^{4b}$ is OH. In another embodiment, $R^{4a}$ is H. In yet another embodiment, $R^{4c}$ is H.

In some embodiments n¹ is 2. In other embodiments n¹ is 3.
In one embodiment, $R^5$ is H.
In some embodiments, the compound of general formula (II) is selected from the group consisting of
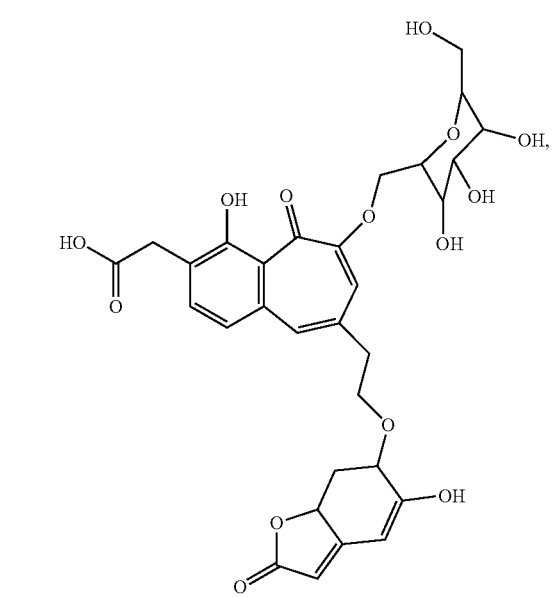
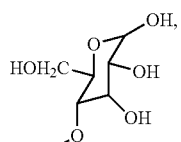
-continued
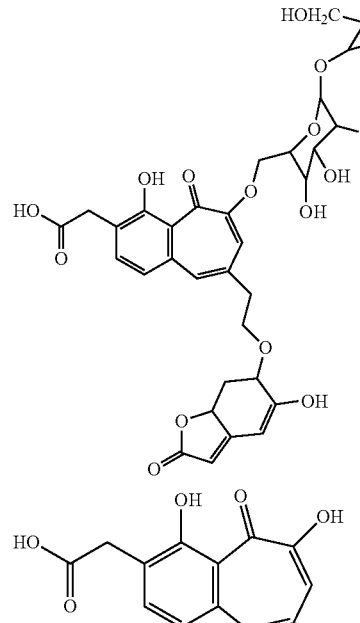
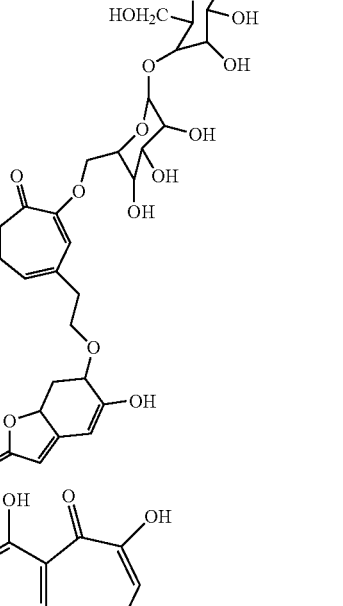
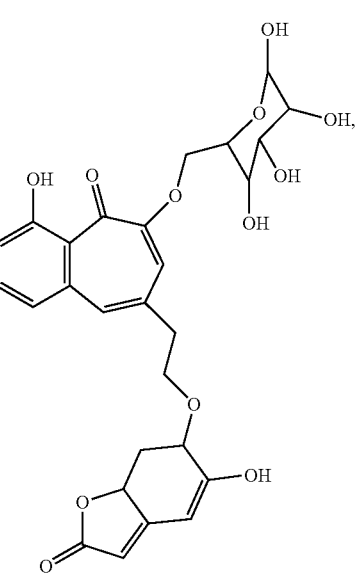

-continued

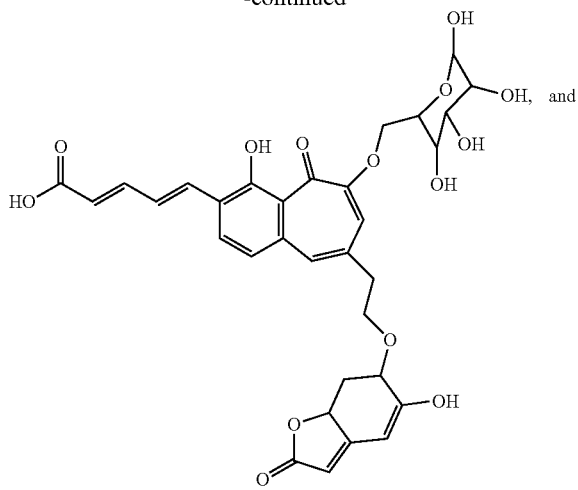

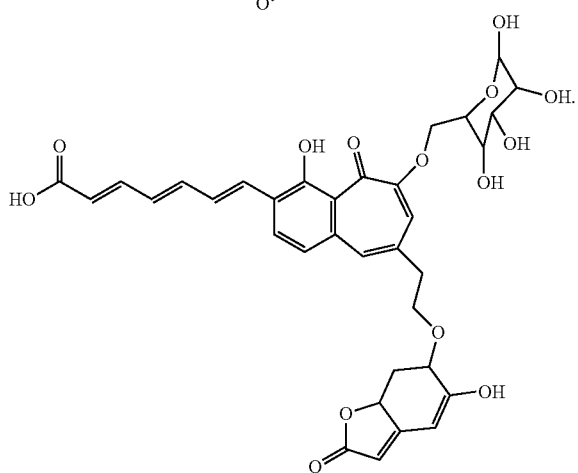

In certain embodiments, the compound of general formula (I) is a compound of general formula (III):

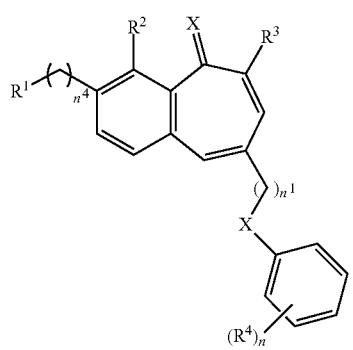
(III)

wherein,
R$^1$ is selected from the group consisting of CH$_3$, CH$_2$OH, —C(=O)OH, —C(=NH)OH, —C(=O)NH$_2$, —C(=NH)NH$_2$, —OH, and —NH$_2$;
R$^2$ is selected from the group consisting of H, CH$_3$, OH, —NH$_2$, —C(=O)OH;
R$^3$ is selected from the group consisting of H, CH$_3$, OH, a monosaccharide, a disaccharide and a polysaccharide;
each occurrence of R$^4$ is independently selected from the group consisting of H, alkyl, substituted alkyl, alkenyl, aryl, substituted aryl, and OH, wherein two adjacent R$^4$ are optionally joined together to form a ring having 5 to 6 ring atoms, wherein the ring is optionally substituted;
each occurrence of X is independently selected from the group consisting of O, NH, and S;
n$_1$ is an integer from 0 to 6; and
n$_2$ is an integer from 0 to 6.

In one embodiment R$^4$ is OH. In another embodiment R$^4$ is selected from the group consisting of (CH=CH)OH, (CH=CH)$_2$OH and (CH=CH)$_3$OH.

In some embodiments, two adjacent R$^4$ are joined together to form a ring having 5 ring atoms, wherein a first R$^4$ is O and a second R$^4$ is C.

In some embodiments, the compound of general formula (III) is selected from the group consisting of

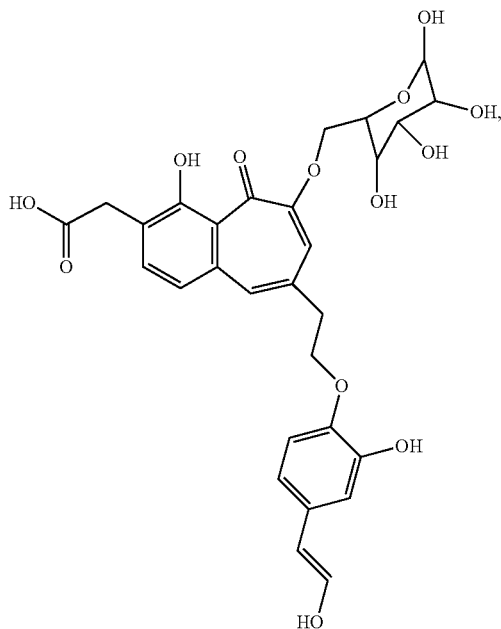

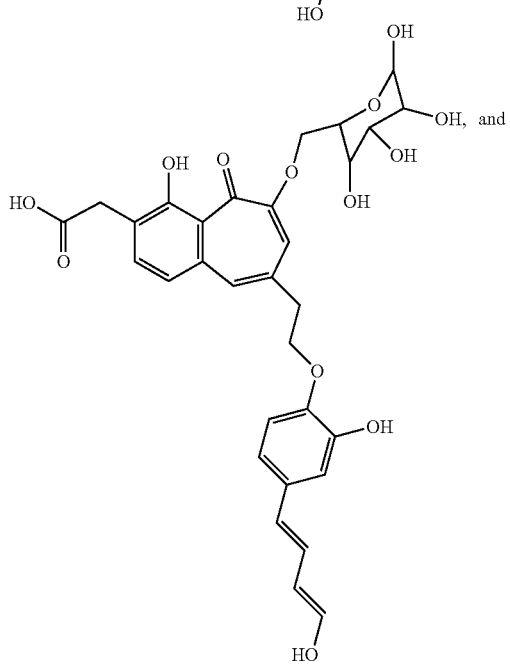

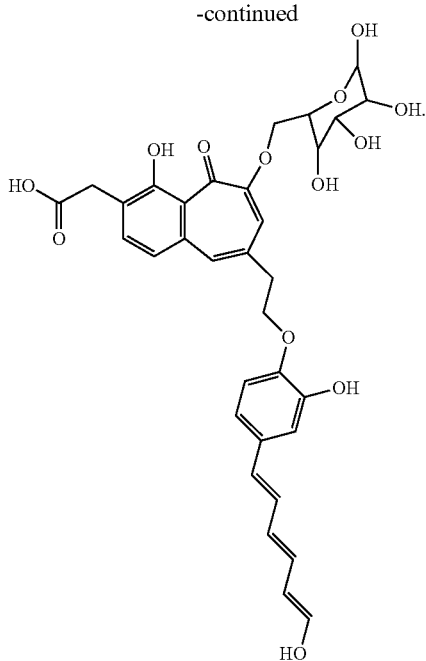

In another embodiment, the compound of general formula (I) is

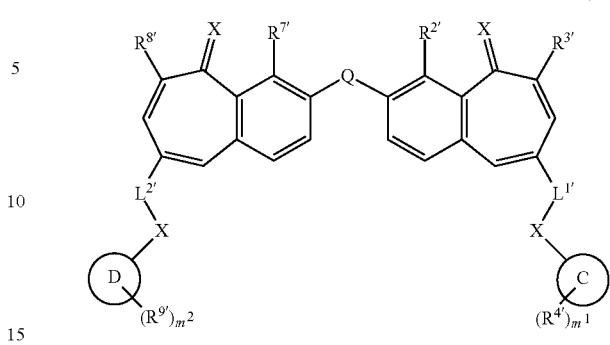

wherein general formula (IV),

Q is selected from the group consisting of $(CH_2)_{m3}$, $(CH=CH)_{m4}$, and $(CH_2)_{m5}(O)O(CO)(CH_2)_{m6}$;

$R^{2'}$ is selected from the group consisting of H, $CH_3$, OH, $-NH_2$, and $-C(=O)OH$;

$R^{3'}$ is selected from the group consisting of H, $CH_3$, OH, a monosaccharide, a disaccharide, and a polysaccharide;

C and D are each independently a cycloalkyl ring having from 5 or 6 ring atoms, wherein the cycloalkyl ring may optionally have 0 to 3 double bonds;

each occurrence of $R^{4'}$ is independently selected from the group consisting of H, alkyl, substituted alkyl, aryl, substituted aryl, and OH, wherein two adjacent $R^4$ are optionally joined together to form a ring having 5 to 6 ring atoms, wherein the ring is optionally substituted;

each of $L^{1'}$ and $L^{2'}$ is selected from the group consisting of a single bond, alkyl, aryl, cycloalkyl, alkylaryl, and alkylcycloalkyl, wherein the alkyl, aryl, cycloalkyl, alkylaryl, or alkylcycloalkyl group is optionally substituted;

each occurrence of X is independently selected from the group consisting of O, NH and S;

$R^{7'}$ is selected from the group consisting of H, $CH_3$, OH, $-NH_2$, and $-C(=O)OH$;

$R^{8'}$ is selected from the group consisting of H, $CH_3$, OH, a monosaccharide, a disaccharide, and a polysaccharide;

each occurrence of $R^{9'}$ is independently selected from the group consisting of H, alkyl, substituted alkyl, aryl, substituted aryl, and OH, wherein two adjacent $R^4$ are optionally joined together to form a ring having 5 to 6 ring atoms, wherein the ring is optionally substituted;

$m_1$ is an integer from 0 to 6;
$m_2$ is an integer from 0 to 6
$m_3$ is an integer from 0 to 3
$m_4$ is an integer from 0 to 3;
$m_5$ is an integer from 0 to 3; and
$m_6$ is an integer from 0 to 3.

In one embodiment $R^{2'}$

In one embodiment, $R^{7'}$ is OH.

In certain embodiments, $R^{3'}$ is a monosaccharide. In one embodiment, the monosaccharide is glucose. In another embodiment, the monosaccharide is fructose. In yet another embodiment, the monosaccharide is galactose.

In certain embodiments, $R^{8'}$ is a monosaccharide. In one embodiment, the monosaccharide is glucose. In another embodiment, the monosaccharide is fructose. In yet another embodiment, the monosaccharide is galactose.

In one embodiment, C is a cycloalkyl ring having 6 ring atoms. In one embodiment the cycloalkyl ring having 6 ring atoms has 1 double bond. In another embodiment, cycloal- In one aspect, the invention provides a compound of general formula (IV):

kyl ring having 6 ring atoms has 2 double bonds. In yet another embodiment, cycloalkyl ring having 6 ring atoms has 3 double bonds.

In one embodiment, D is a cycloalkyl ring having 6 ring atoms. In one embodiment the cycloalkyl ring having 6 ring atoms has 1 double bond. In another embodiment, cycloalkyl ring having 6 ring atoms has 2 double bonds. In yet another embodiment, cycloalkyl ring having 6 ring atoms has 3 double bonds.

In one embodiment, $R^{4'}$ is OH. In another embodiment, two adjacent $R^{4'}$ are joined together to form a 5-membered ring. In one embodiment, two adjacent $R^{4'}$ are joined together to form a 5-membered ring, wherein at least one $R^{4'}$ is O.

In one embodiment, $R^{9'}$ is OH. In another embodiment, two adjacent $R^{9'}$ are joined together to form a 5-membered ring. In one embodiment, two adjacent $R^{4'}$ are joined together to form a 5-membered ring, wherein at least one $R^{9'}$ is O.

In one embodiment $L^{1'}$ is $CH_2$. In another embodiment, $L^{1'}$ is $(CH_2)_2$. In yet another embodiment, $L^{1'}$ is $(CH_2)_3$.

In one embodiment $L^{2'}$ is $CH_2$. In another embodiment, $L^{2'}$ is $(CH_2)_2$. In yet another embodiment, $L^{2'}$ is $(CH_2)_3$.

In one embodiment Q is $R^{10}(C=O)O(C=O)R^{11}$

In some embodiments $R^{10}$ is selected from an alkyl, alkenyl, aryl, cycloalkyl, alkylaryl, and alkylcycloalkyl, wherein the alkyl, aryl, cycloalkyl, alkylaryl, or alkylcycloalkyl group is optionally substituted. In one embodiment $R^{10}$ is an alkyl. In yet another embodiment $R^{10}$ is $CH_2$.

In some embodiments $R^{11}$ is selected from an alkyl, alkenyl, aryl, cycloalkyl, alkylaryl, and alkylcycloalkyl, wherein the alkyl, aryl, cycloalkyl, alkylaryl, or alkylcycloalkyl group is optionally substituted. In one embodiment $R^{11}$ is an alkyl. In yet another embodiment $R^{11}$ is $CH_2$.

In one embodiment Q is $CH_2(C=O)O(C=O)CH_2$.

In one embodiment, the compound of general formula (IV) is

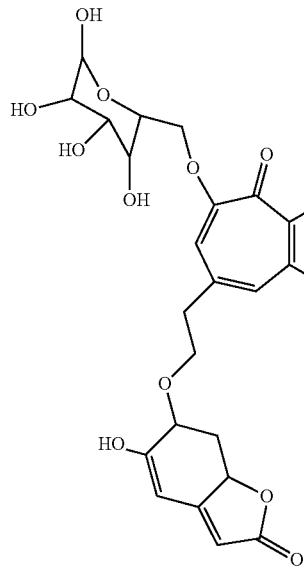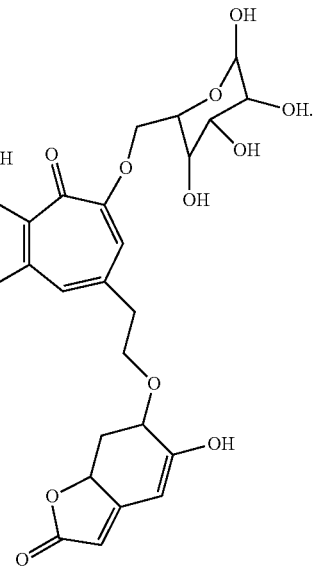

Compound Preparation

In one embodiment, the invention provides compound prepared by a process comprising the following steps: A compound prepared by a process comprising the steps of:

obtaining a seed of *Persea americana*; grinding size reduction of the seed to obtain a slurry; incubating the slurry; extracting the compound by incubating the slurry with an alcohol to form a first mixture; isolating a first substance from the first mixture; removing the insoluble particles from the first substance; precipitating the substance to form a second mixture; isolating a second substance from the second mixture; adsorbing the second substance to a resin; and isolating the compound by eluting the compound from the resin with an alcohol.

In one embodiment, the alcohol is methanol, ethanol, acetone, citric acid, acetic acid or any combination thereof. In one embodiment, the alcohol is diluted in water.

In one embodiment, the step grinding size reduction of the seed comprises two steps, a course size reduction step and a second fine reduction step.

In one embodiment, the step incubating the slurry comprises incubating the slurry for at least one minute. In one embodiment, the incubation is for more than 30 minutes.

In one embodiment, the incubation is up to 48 hours. In one embodiment, the step incubating the slurry comprises incubating the slurry for 0-40° C. In one embodiment, the incubation is at 20-40° C. In one embodiment, the incubation is at 20° C.

In one embodiment, the step isolating a first liquid from the first mixture comprises centrifugation or filtration through a filter.

In one embodiment, the step removing the insoluble particles from the first substance comprises filtration through a filter.

In one embodiment, precipitating the slurry comprises incubating the slurry for at least 24 hours and up to 48 hours. In one embodiment, incubating the substance comprises incubating the liquid at 4° C.

In one embodiment, the step isolating a second substance from the second mixture comprises filtration or centrifugation.

In one embodiment, the step adsorbing the second substance to a resin comprises applying the liquid to a XAD-7 resin. In one embodiment, the resin is washed twice.

In one embodiment, the compound is isolated by eluting the compound from the resin with an alcohol. In one embodiment compound is concentrated by evaporation. In one embodiment the compound is dried by freeze drying or spray drying. In one embodiment, the dried compound is mixed with an excipient. In one embodiment the excipient is maltodextrin or sugar.

Salts of the Compounds of the Invention

The compounds described herein may form salts with acids or bases, and such salts are included in the present invention. The term "salts" embraces addition salts of free acids or free bases that are compounds of the invention.

Compositions of the Invention

The invention includes an edible composition comprising a compound of the invention. In one embodiment, the compound of the invention in the edible material is present in an amount from about 0.25 mg/mL to about 10 mg/mL. In one embodiment, the edible material comprising a compound of the invention has a hue selected from the group consisting of red, orange and yellow.

In one aspect of the invention, compounds of the invention may be combined with one or more natural or artificial food colorants such as those approved by the U.S. Food and Drug Administration (http://www.fda.gov/ForIndustry/ColorAdditives/ColorAdditiveInventories/ucm115641.htm). In one embodiment, the natural food colorant includes, but is not limited to Citrus Red #2, safranol curcumin, capsaicin, β-carotene, bixin, and carmine, annato extract, dehydrated beets, canthaxanthin, caramel, β-apo-8'-carotenal, cochineal extract, carmine, sodium copper chlorophyllin, toasted partially defatted cooked cottonseed flour, ferrous gluconate, ferrous lactate, grape color extract, synthetic iron oxide, fruit juice, vegetable juice, carrot oil, paprika, paprika oleoresin, mica-based pearlescent pigments, riboflavin, saffron, *spirulina* extract, titanium dioxide, tomato lycopene extract, tomato lycopene concentrate, turmeric, and turmeric oleoresin.

In another embodiment, the artificial food colorant includes but is not limited to FD&C Blue #1, FD&C Blue #1 Aluminum Lake, FD&C Blue #2, FD&C Blue #2 Aluminum Lake on alumina, FD&C Green #3, FD&C Red #3, FD&C Red #40 and its Aluminum Lake, FD&C Yellow #5, FD&C Yellow #5 Aluminum Lake, FD&C Yellow #6, FD&C Yellow #6, FD&C Yellow #6 Aluminum Lake, titanium complexes, and Orange B.

In one aspect, the composition of the invention further comprises an aluminum-containing compound, to form an aluminum lake, wherein the unpleasantness of the taste and/or odor of the coloring material is reduced by said combination with the aluminum-containing compound. In another aspect, the composition of the invention further comprises calcium.

In another embodiment, the composition of the invention further comprises a diluent and is in a form including, but not limited to, liquids, powders, gels, and pastes.

In one aspect, the composition of the invention could be an extract of avocado seeds. In another aspect, the composition is freeze-dried or spray-dried.

Methods of the Invention

In one aspect, the present invention provides methods for coloring a material. In one embodiment, the material is an edible material, a food product, a cosmetic product, a drug product or a medical device. In certain embodiments, the material is orange. In other embodiments, the material is yellow. In yet another embodiment, the material is red. In one embodiment, the method for coloring a material comprises adding a compound of the invention to the material.

In one embodiment, the method further comprises adding a compound of the invention to the edible material at a desired concentration. In one embodiment, the concentration is from about 0.25 mg/mL to about 10 mg/mL. In one embodiment, the concentration is from about 1 ppm to 10 ppm. In one embodiment the concentration is from about 1 ppm to 100 ppm. In another embodiment the concentration is from about 1 ppm to 1000 ppm. In yet embodiment the concentration is from about 1 ppb to 10 ppb. In yet embodiment the concentration is from about 1 ppb to 100 ppb. In yet embodiment the concentration is from about 1 ppb to 500 ppb.

In some embodiments, the invention provides a method of imparting a color to a substrate. In some embodiments, the method of imparting a red, orange or yellow color to a substrate (e.g., a food item, a cosmetic, a drug or nutraceutical product, a textile product, a device such as a medical device) comprises contacting the substrate with a colorant composition comprising at least one compound of the invention described herein. In some embodiments, the colorant composition is prepared by mixing a compound herein with a color additive (e.g. a FDA approved color additive). In some embodiments, the substrate is an edible material. In some embodiments, the substrate is a food item. In some embodiments, the substrate is a medical device. In some embodiments, the substrate is a drug product. In some embodiments, the substrate is a nutraceutical product. In some embodiments, the substrate is a cosmetic product.

In certain embodiments, the amount of a colorant composition to be incorporated into a material depends on the final color to be achieved. In some embodiments, the food product, the cosmetic product, the drug product, the medical device, comprises a colorant composition disclosed herein in an effective amount, by itself or with another colorant, to impart the edible material, food product, cosmetic product, drug product or medical device a color including, but not limited to orange, yellow and red.

In one embodiment, the invention provides a method of coloring a material, wherein the color is a yellow hue, a red hue or an orange hue.

In one embodiment, the invention provides a method of coloring a material, wherein the color is a yellow hue, including, but not limited to Amber, Apricot, Arylide yellow, Aureolin, Beige, Buff, Cadmium pigments, Chartreuse, Chrome yellow, Citrine, Citron, Color term, Cream, Dark goldenrod, Diarylide pigment, Ecru, Flax, Fulvous, Gamboge, Gold, Goldenrod, Hari, Harvest gold, Icterine, Isabelline, Jasmine, Jonquil, Khaki, Lemon, Lemon chiffon, Lime, Lion, Maize, Marigold, Mikado yellow, Mustard, Naples yellow, Navajo white, Old gold, Olive, Or (heraldry), Peach, Pigment Yellow 10, Pigment Yellow 16, Pigment Yellow 81, Pigment yellow 83, Pigment yellow 139, Saffron, Sage, School bus yellow, Selective yellow, Stil de grain yellow, Straw, Titanium yellow, Urobilin, or Vanilla.

In one embodiment, the invention provides a method of coloring a material, wherein the color is a red hue, including, but not limited to, Scarlet, Imperial red, Indian red, Spanish red, Desire, Lust, Carmine, Ruby, Crimson, Rusty red, Fire engine red, Cardinal red, Chili red, Cornell Red, Fire brick, Redwood, OU Crimson, Dark red, Maroon, Barn red, and Turkey red.

In one embodiment, the invention provides a method of coloring a material, wherein the color is an orange hue, including, but not limited to, Papaya whip, Peach, Apricot, Melon, Atomic tangerine, Tea rose, Carrot orange, Orange peel, Princeton orange, UT Orange, Spanish orange, Tangerine, Pumpkin, Giants orange, Vermilion (Cinnabar), Tomato, Bittersweet, Persimmon, Persian orange, Alloy orange, Burnt orange, Bittersweet shimmer, Brown. In one embodiment the yellow hue has a wavelength from 585 nm-620 nm.

The effectiveness of the colorant composition can be determined by comparing (e.g., by visual comparison) a color to be achieved (e.g., a red) with the product or device colored with an amount of the colorant composition.

In one aspect, the compounds of the invention can be used in cosmetic settings. In another aspect of the invention the compounds can be used for coloring drugs. In yet another application, the compounds can be used to color nutritional supplements.

EXAMPLES

The invention is now described with reference to the following Examples. These Examples are provided for the purpose of illustration only, and the invention is not limited to these Examples, but rather encompasses all variations that are evident as a result of the teachings provided herein.

Example 1: Characterization of a Natural Orange Pigment Found in Hass Avocado (*Persea americana*) Seed for Use as a Natural Food Colorant Avocado seed extract represents a novel source of yellow-orange-red natural colors, which are stable in a variety of conditions. The use of colored avocado seed extracts are particularly appealing for products with long shelf-lives such as beverages and candies, as well as products which are baked or undergo pasteurization. Using avocado seed extract as a natural colorant will provide a new value-added use for avocado seeds which are typically viewed as a low-value waste product.

There is a great demand presently for natural colors to replace artificial colorants. However, a large limitation for natural colorants is their instability. The data presented herein provides natural compounds and derivatives thereof which have greater color intensity and are significantly more stable to heat, light and oxygen than other natural colorants, especially those in the yellow-red range. Moreover, because of the superior stability, the compounds of the present invention are less toxic.

The materials and methods employed in the experiments presented in this Example are now described.

Preparation of a Semi-Pure Colored Avocado Seed Extract

Hass avocados, Great Value Pure Cane Sugar, Sprite, Great Value 100% Apple Juice, Ocean Spray 100% White Grapefruit Juice, Pillsbury Tradition Vanilla Cake Mix, and other baking food materials were purchased from local grocery stores. Chemicals used were reagent grade and were used as supplied except where noted. Lyophilization was performed using a Virtis Genesis 25 XL Pilot Lyophilizer (Warminster, Pa.). Organic solvents were removed using a rotary evaporator (Heidolph; Germany). L*a*b* values were determined using a Minolta CR-200 Chroma Meter (Japan). All LC samples were filtered using 25 mm syringe filter with 0.45 μm cellulose acetate membrane (VWR; Radnor, Pa.). All other reagents were of the highest quality available.

After removal from the avocados, seeds were cleaned, peeled, and chopped by hand into small pieces. The pieces were then were blended with deionized, distilled water in a laboratory blender (Waring; Wilmington, N.C.) for 60 s. The resulting seed/water mixture was placed in the refrigerator at 4° C. for 24 h. After 24 h, the supernatant was gravity filtered through blotting paper (grade 703, VWR). The filtered supernatant was frozen in plastic trays and lyophilized to produce a dried, raw extract (~3.73% yield). The dried raw extract was further purified by flash chromatography using a nitrogen pressurized (<2 ppm moisture, Penn State General Stores) glass column packed with amberlite XAD7-HP (Sigma; Cleveland, Ohio). The column was eluted with water to removed sugars from the extract, and a colored fraction eluted using methanol containing 0.1% (v/v) acetic acid. The organic solvent was removed using a rotary evaporator, and the remaining water frozen and lyophilized to produce a semi-pure colored extract (~29% yield). This semi-pure extract was used in all color and stability studies.

Color and Stability of Semi-Pure CASE in Some Commercial and Model Food Products Color Studies Semi-pure CASE (colored avocado seed extract) was added to Sprite (pH 3.29), apple juice (pH 3.71), white grapefruit juice (pH 3.25), and white cupcake mix at final concentrations of 0, 0.25, 0.75, 1, 3, 5, 8, and 10 mg/mL. For the cupcakes, L*a*b* values were determined after baking and were measured on both the middles and tops of the cakes.

For each food product, L*a*b* values were found and ΔE values calculated using the uncolored food product as the control and using the equation $$\Delta E = \sqrt{(L_0-L)^2+(a_0-a)^2+(b_0-b)^2}$$

where $L_0$, $a_0$, and $b_0$ are the respective values of the uncolored food sample.

To prepare cheese sauces, regular orange and color-additive free white Kraft cheese powders were provided by Wincrest Bulk Foods (Munnsville, N.Y.). Orange cheese powders were prepared using 1, 5, 10, and 20% by weight semi-pure CASE in the white cheese powder. L*a*b* values were determined for each dry cheese powder as well as prepared cheese sauce (1 g cheese powder combined with 2 mL warm, skim milk). L*a*b* values were used to calculate ΔE for each sample, with white cheese powder used as the control Stability Studies in Model Sugar Drinks Samples were prepared by adding semi-pure CASE to a model sugar drink solution (2.6 M sodium citrate buffer containing 500 g/L sucrose). The solutions were adjusted to either pH 2.5 or pH 5.85. Semi-pure CASE was added to final concentrations of 0, 1, and 5 mg/mL. The samples were prepared in duplicate and placed into screw-cap GC vials. After being sealed into the GC vials, samples were bubbled with nitrogen to remove oxygen from the sample and the headspace. The samples were then divided into four treatment groups and sampled as outlined in Table 1. Sample testing at each time point included pH determination, L*a*b* values, and UV-Vis spectroscopy. At each time point, a 3 mL aliquot was removed from each sample using a gas-tight syringe while bubbling nitrogen through the sample in order to retain an oxygen free environment.

TABLE 1

Sampling time points (days) on which each treatment group was sampled.

| Dark, 40° C. | Dark, 23° C. | Dark, 4° C. | Light, 26° C. |
|---|---|---|---|
| 1 | 1 | — | 1 |
| 2 | 2 | — | 2 |
| 3 | — | — | — |
| 4 | — | — | — |
| 5 | — | — | — |
| 6 | — | — | — |
| 7 | — | — | — |
| 8 | 8 | 8 | 8 |
| — | 15 | 15 | 15 |
| — | 21 | 21 | 21 |
| — | 29 | 29 | 29 |
| — | 37 | 37 | 37 |
| — | 43 | 43 | 43 |
| — | 50 | 50 | — |
| — | 56 | 56 | — |

Effects of pH on the Color of CASE

Two identical samples of semi-pure colored extract were prepared by dissolving 0.05 g of the extract in 10 mL distilled, deionized water. Samples were stirred with stir plates. The native pH of the treatment and control samples was 3.32 and 3.42, respectively. The treatment sample was treated with 10 M NaOH until the sample reached pH 12.32. The treatment sample was then treated with 6 M HCl until pH 1.59 was reached. In all cases an equivalent volume of water was added to the control sample in order to maintain similar concentrations. The final pH of the control sample was 3.50, and the treatment sample was finally adjusted to pH 3.57.

Preparation of Colored and Uncolored Avocado Seed Extracts for Metabolomics

Five biological replicates were prepared of both colored and uncolored extracts. Each replicate contained approximate 10 g portions from two avocado seeds, totaling 20 g of seed per replicate. Colored replicates were prepared by blending ~20 g of seeds into 400 mL of deionized, distilled water. For uncolored replicates, ~20 g of seeds was blended into 400 mL of deionized distilled water containing tropolone (5.0 mg, 0.041 mmol). Studies were completed at the Penn State Metabolomics Core facility with the help of Phillip Smith, in the laboratory of Andrew Patterson. LC-MS/MS was completed using a Shimadzu (Kyoto, Japan) Prominence UFLC and an AB SCIEX (Framingham, Mass.) 5600 Triple TOF Mass Spectrometer and principal component analysis (PCA) was performed used SIMCA P statistical package.

Structure Elucidation of the Colored Compound

HPLC Purification

The semi-pure, post-amberlite CASE was further purified using an Agilent PrepStar system with 440-LC fraction collector (Santa Clara, Calif.). The extract was dissolved in deionized, distilled water to a final concentration of 20 mg/mL and filtered. Samples (10 mL) were injected onto a Viva C18 250 mm×10 mm×5 μm column (Restek, Bellefonte, Pa.). Samples were separated using a gradient of deionized water containing 0.1% acetic acid and acetonitrile. The percentage of acetonitrile increased with time as follows; 0 min, 5%; 0-40 min, 5-30%; 40-45 min, 30-95%; 45-48 min, 95%; 48-49 min, 95-5%; 49-51 min, 5% at a flow rate of 4 mL/min. Fractions were collected at 30 s intervals (2 mL each) from 19.5 min to 26 min. The peak of interest, F12, eluted at approximately 22 min. All subsequent fractions containing F12 were combined and lyophilized to produce "rough F12." In some instances, F12 as referred elsewhere herein, may have an IUPAC names as follows: 2-(4-hydroxy-8-(2-((5-hydroxy-2-oxo-2,6,7,7a-tetrahydrobenzofuran-6-yl)oxy)ethyl)-5-oxo-6-(((2R,4R,5R)-3,4,5,6-tetrahydroxytetrahydro-2H-pyran-2-yl)methoxy)-5H-benzo[7]annulen-3-yl)acetic acid.

Once dried, the rough F12 samples were diluted with deionized water and 10 mL samples were injected onto an Ultra Aromax 250 mm×10 mm×5 μm column (Restek). Samples were resolved using a gradient method of deionized water containing 0.1% acetic acid, and methanol. The percentage of methanol was increased as a function of time as follows: 0 min, 48%; 0-13.5 min, 48-65%; 13.5-14.5 min, 65%; 14.5-15 min, 65-48%; 15-17 min, 48%, at a flow rate of 4 mL/min. Fractions were collected at 24 sec intervals (1.6 mL each from 8.9 min to 14.5 min. The peak of interest eluted as the later of 2 overlapping peaks at approximately 10.6 min to produce pure F12.

Pure F12 fractions were combined and lyophilized. 20 μL injections were made onto an ultra Aromax 150 mm×4.6 mm×5 μm column (Restek; Bellefonte, Pa.). A gradient method was used with solvent being filtered DDI water with 0.1% acetic acid and solvent B being methanol. The method was as follows: 0 min, 45%; 0-25, 45-62%; 25-28 min, 62%; 28-29 min, 62-45%; 29-31 min, 45%. If additional purification was necessary, the fractions were again fractionated using the PrepStar system.

High Resolution MS/MS Analysis

Samples (5 ul) were separated by reverse phase HPLC using a Prominence 20 UFLCXR system (Shimadzu, Columbia Md.) with a Waters (Milford, Mass.) BEH C18 column (100 mm×2.1 mm 1.7 um particle size) maintained at 55° C. and a 20 minute aqueous acetonitrile gradient, at a flow rate of 250 ul/min. Solvent A was HPLC grade water with 0.1% formic acid and Solvent B was HPLC grade acetonitrile with 0.1% formic acid. The initial condition were 97% A and 3% B, increasing to 45% B at 10 min, 75% B at 12 min where it was held at 75% B until 17.5 min before returning to the initial conditions. The eluate was delivered into a 5600 (QTOF) TripleTOF using a Duospray™ ion source (all AB Sciex, Framingham, Mass.). The capillary voltage was set at 5.5 kV in positive ion mode and 4.5 kV in negative ion mode, with a declustering potential of 80V. The mass spectrometer was operated in IDA (Information Dependent Acquisition) mode with a 100 ms survey scan from 100 to 1200 m/z, and up to 20 MS/MS product ion scans (100 ms) per duty cycle using a collision energy of 50V with a 20V spread. Principal component analysis was processed using square root mean square analysis. Known compounds were identified using the Scripps METLIN metabolomics database.

Attenuated Total Reflectance Fourier Transform Infrared Spectroscopy (ATR)

ATR experiments were conducted using a Bruker (Billerica, Mass.) Vertex 70v scanning the mid-IR range.

High Resolution NMR Analysis

Experiments used a Bruker Avance II HD 500 MHz NMR with $LN_2$ cryoprobe. 1D $^1H$ and $^{13}C$ experiments, as well as 2D Correlation Spectroscopy (COSY), Total Correlation Spectroscopy (TOCSY), Heteronuclear Multiple Bond Correlation (HMBC), and Distortionless Enhancement by Polarization Transfer (DEPT) edited Homonuclear Single bond Quantum Correlation (HSQC) experiments were conducted on two separate samples, one in $D_2O$ and one in $(CD_3)_2SO$. Additionally a 2D Nuclear Overhauser Effect Spectroscopy (NOESY) and selective TOCSY and Rotating Frame NOESY (ROESY) experiments were conducted on the $D_2O$ sample. Data was processed using Topspin and MestReNova software.

The results of the experiments presented in this Example are now described.

Colorant Properties of Semi-Pure CASE in a Panel of Commercial Food Products

Figure 2:
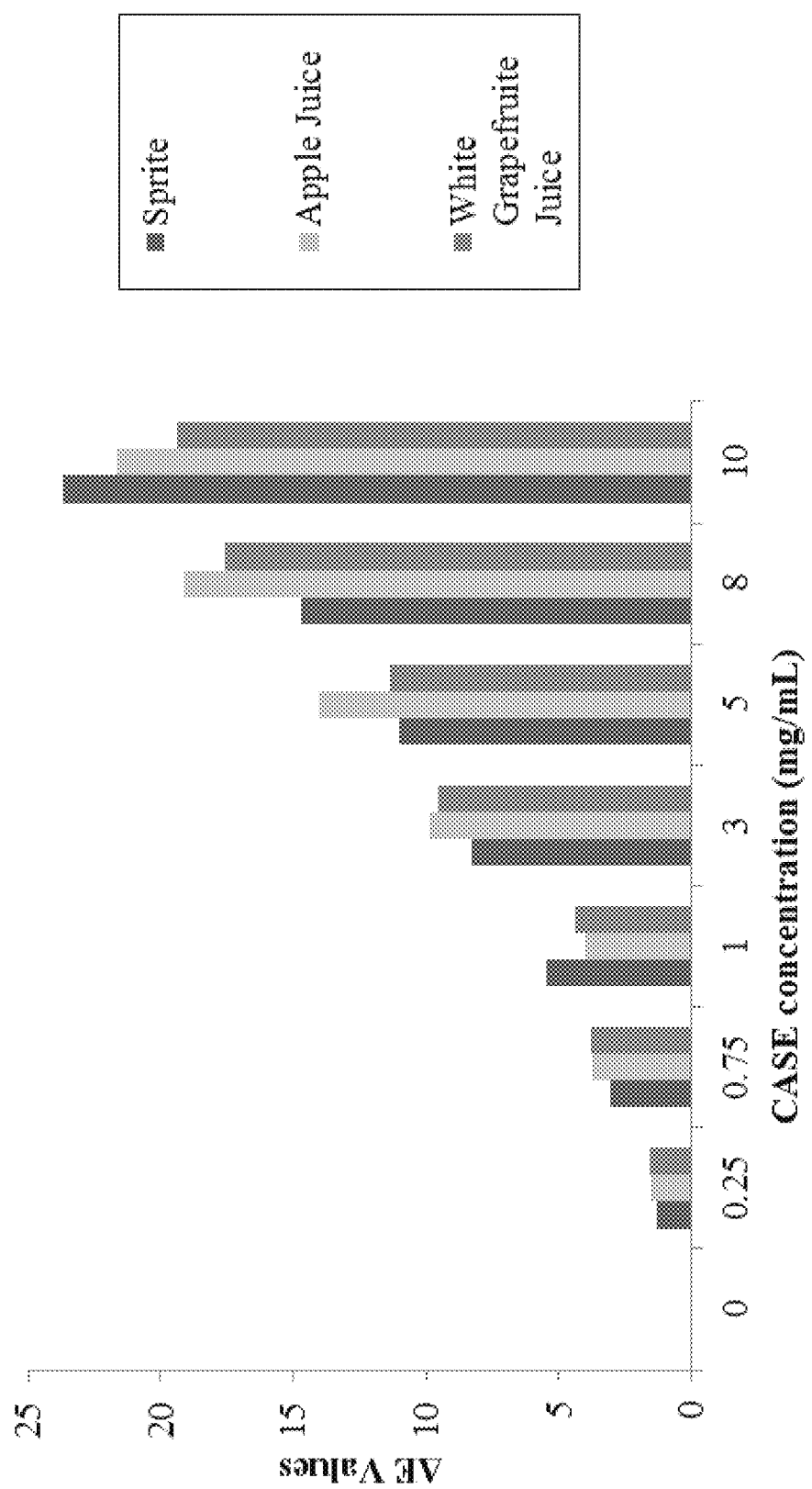
FIG. 2 depicts results of experimental examples showing the ΔE values of semi-pure CASE in soda (Sprite), apple juice, and white grapefruit juice.
Figure 3:
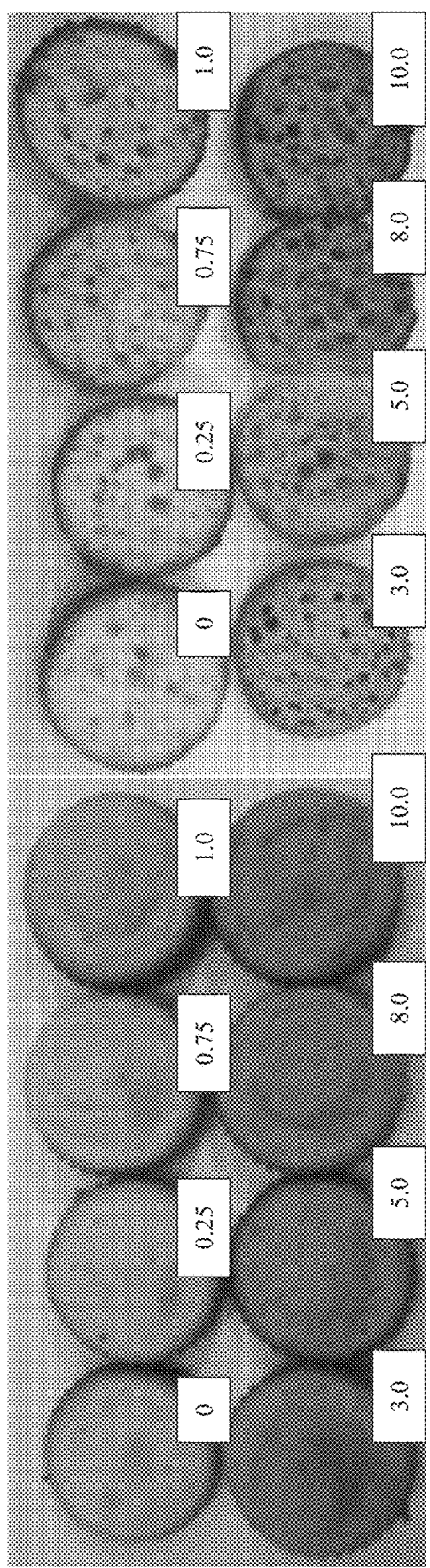
FIG. 3, comprising
Figure 4:
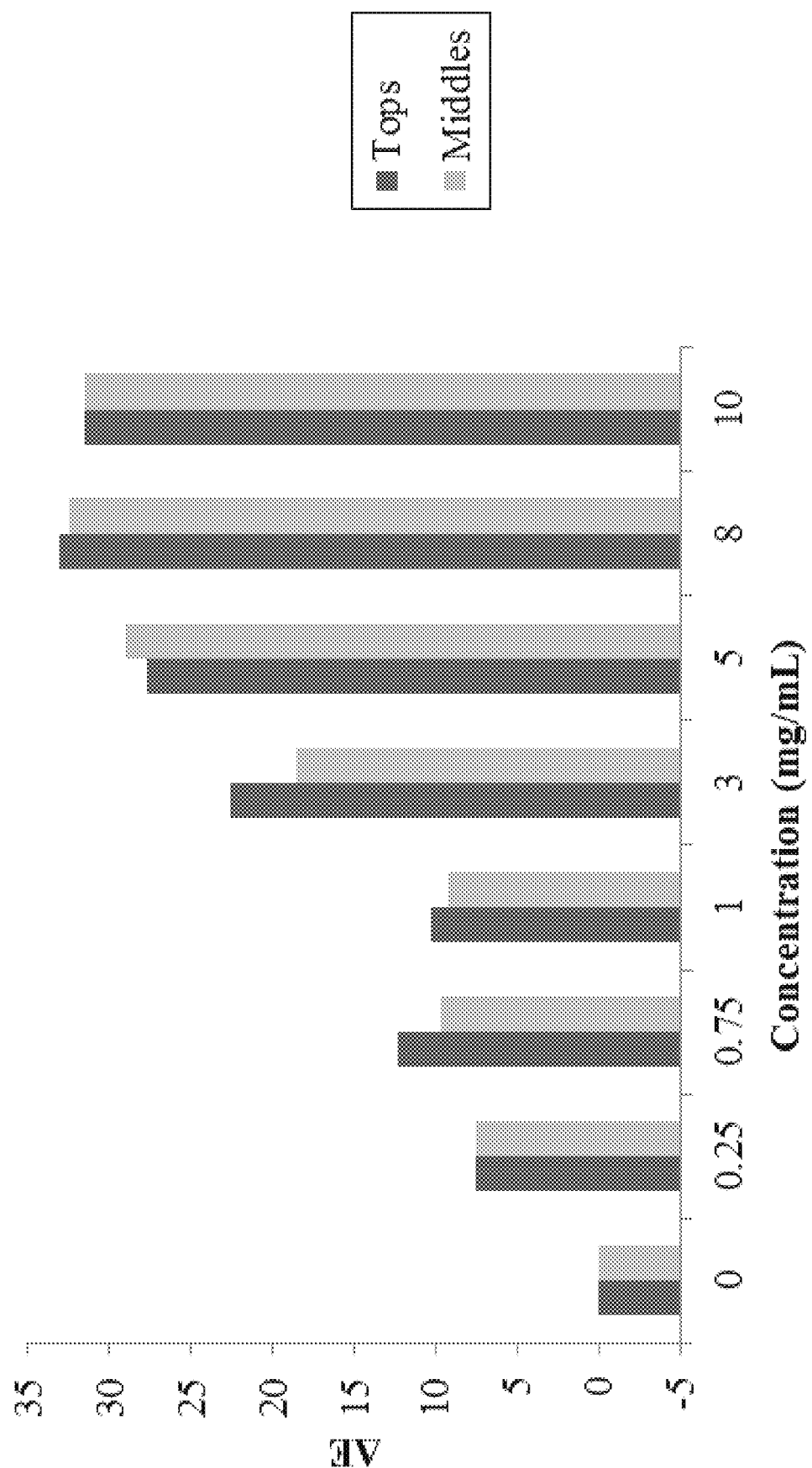
FIG. 4 depicts results of experimental examples showing the ΔE values of semi-pure CASE in cupcake tops and middles.

Semi-pure CASE was added to three commercial beverages to assess the behavior of the pigment in a variety of matrices (FIG. 1). Visually, the color of the extract appeared to be the most vibrant in the Sprite. FIG. 2 shows the calculated ΔE values for the samples. When used in baking, the semi-pure CASE retained its colorant properties well, although it should be noted that higher concentrations of the extract produced a denser crumb (FIG. 3). Baked samples were prepared in duplicate. The addition of semi-pure CASE showed a steady climb in ΔE values in both the tops and middles of the cupcakes (FIG. 4).

Figures 5A, 5B:
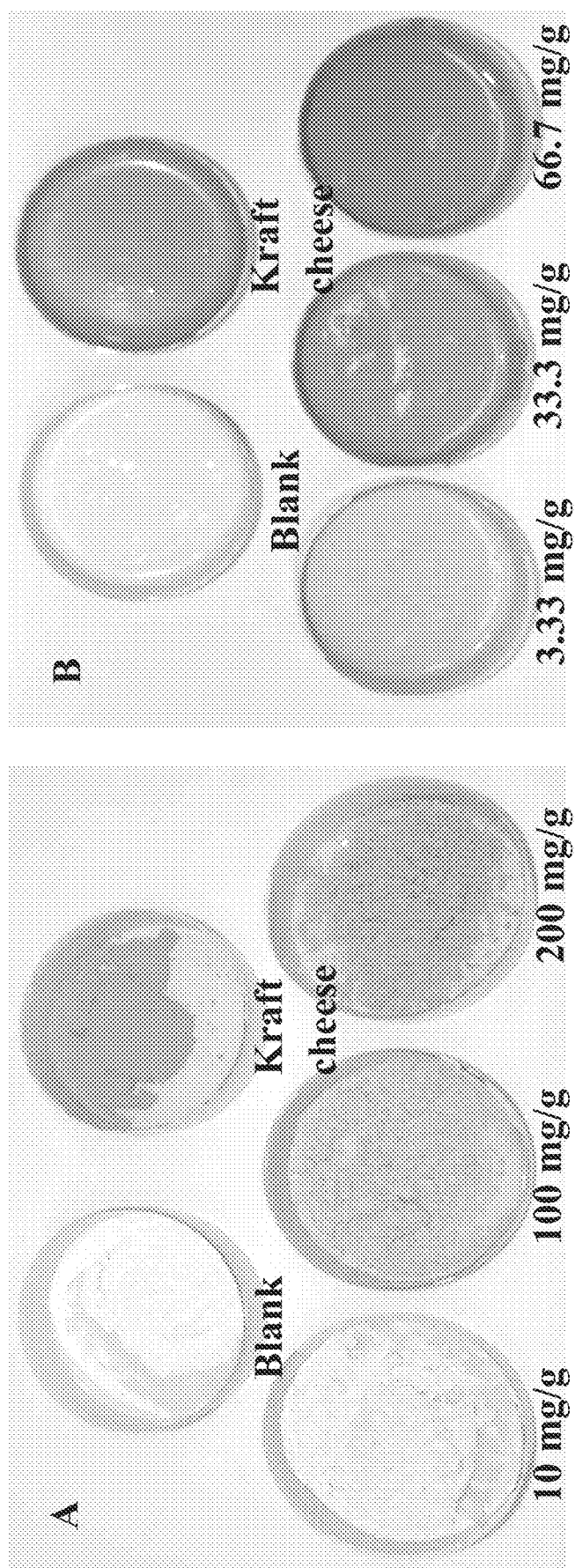
FIGS. 5A and 5B, depicts results of experimental examples demonstrating the color of cheese when semi-pure CASE was added to a white no-color-added cheese powder (blank). Warm milk was then added to the resulting samples in order to prepare a cheese sauce.
Figure 6:
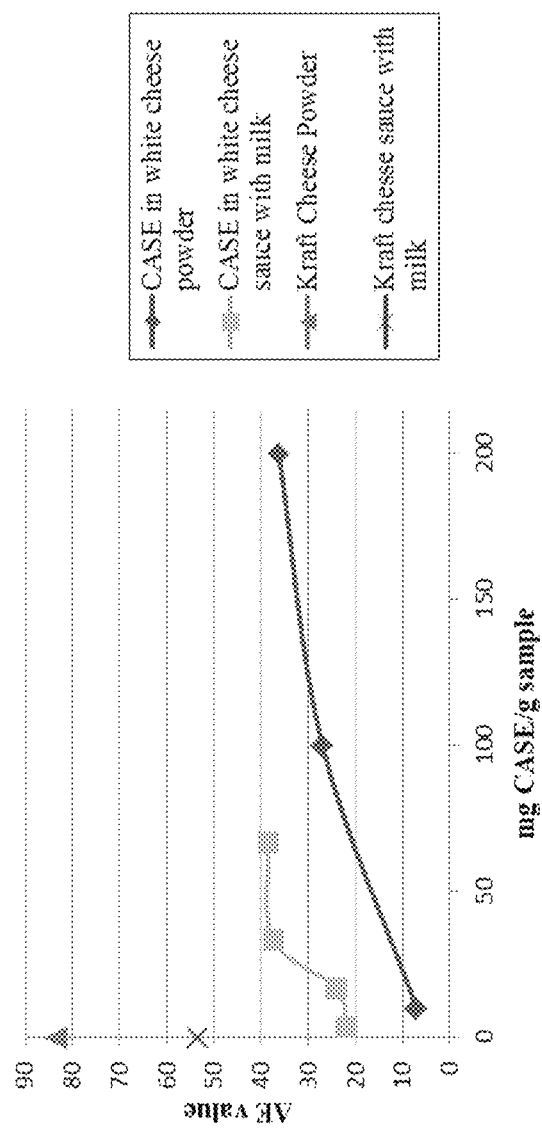
FIG. 6 depicts results of experimental examples demonstrating the ΔE values of CASE in a white no-color-added Kraft cheese powder. ΔE of the white and regular Kraft cheese powders were also calculated and appear as zero-points along the x-axis.

Semi-pure CASE was also added to white cheese powder (blank) and compared to regular orange Kraft cheese powder (FIG. 5A). To create a cheese sauce, warm milk (2 mL/g) was added to the cheese powders (FIG. 5B). The CASE produced a strong orange color, but was not as bold or bright as the regular Kraft cheese powder. The ΔE values appear to reach a maximum around 100 mg/g dry sample or 33.3 mg/g prepared sample. A similar result was observed in the white cake mix around 8 mg/mL semi-pure CASE.

Stability of Semi-Pure CASE in a Model Sugar Drink

Figures 7A, 7B, 7C, 7D:
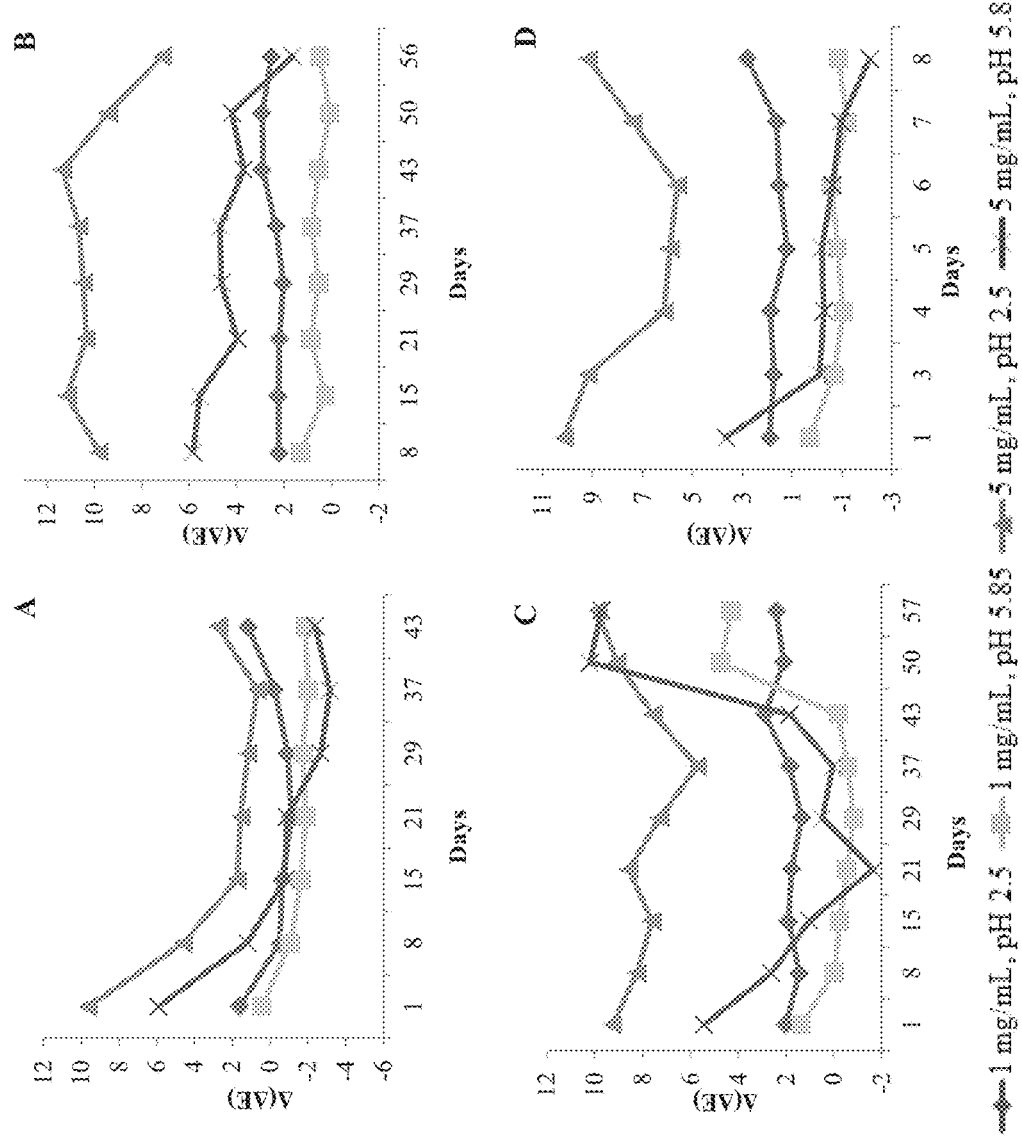
FIGS. 7A through 7D, depicts results of experimental examples demonstrating the change in ΔE of samples.
Figure 8:
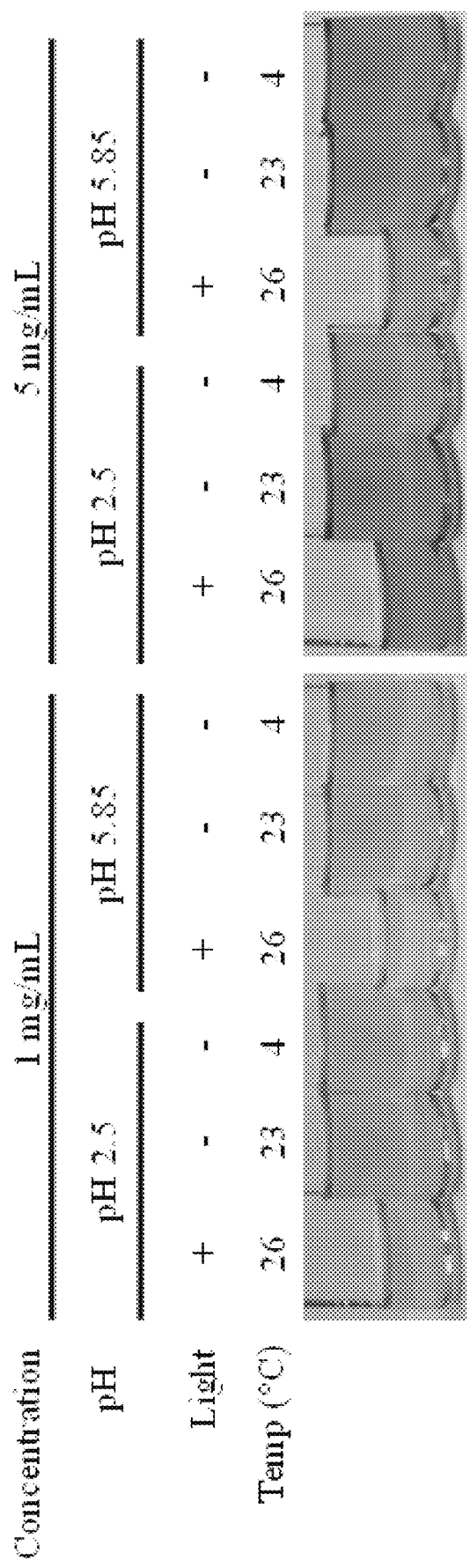
FIG. 8 depicts results of experimental examples demonstrating color of CASE in model sugar drink samples on day 36 of the stability study.
Figures 9A, 9B, 9C, 9D:
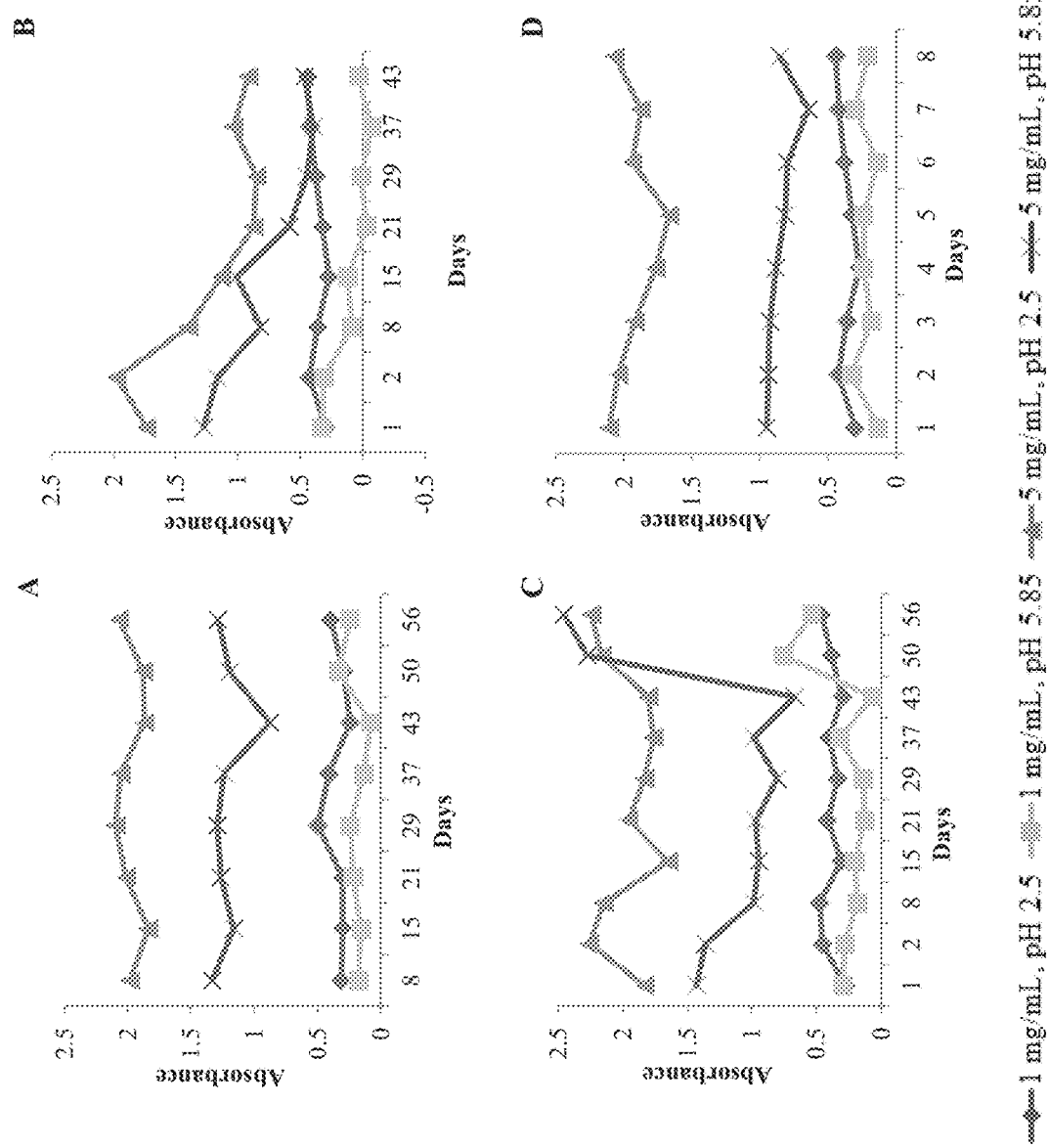
FIGS. 9A through 9D, depicts results of experimental examples demonstrating the change in 445 nm absorbance.

Semi-pure CASE samples were prepared in a model sugar drink with concentrations of 1 mg/mL or 5 mg/mL, and at pH 2.5 and pH 5.85. Treatment groups consisted of three dark groups at 4° C., 23° C., and 40° C., and one treatment group of lighted samples at 26° C. Samples were prepared in duplicate, and L*a*b* measurements of each sample were performed twice. ΔE values for the samples can be seen in FIG. 7. In general, the greater the ΔE value, the more likely it is that the corresponding color change is perceptible to the human eye. It is widely accepted that a change of ΔE<2.5 is insignificant, or likely to be imperceptible to the human eye (Salameh et al., 2014, Int J Esthet Dent 9:1-9). After deoxygenation by bubbling nitrogen through samples, a change in pH in the order of –0.35 pH units was observed for all samples. The pH of all samples then remained constant throughout the remainder of the experiment. Some variation in ΔE is expected due to the nature of the experiment. Apart from some minor fluctuations, samples retained their bright colors even after 50 d. Photos of the samples on day 36 are shown below in FIG. 8. Samples were measured on the spectrometer during the experiment to determine any change in sample absorbance at 445 nm, the wavelength corresponding to the most prominent colored compound (FIG. 9). Though the light treated samples experienced a minor decrease in ΔE values over time, they showed no significant change in absorbance at 445 nm. Both the 1 mg/mL at pH 5.85 and the 5 mg/mL samples at pH 2.5 samples experienced increases in ΔE and absorbance at 445 in the darkened, room temperature samples during the final three weeks. This may have been due to formation of a precipitate or improper sampling technique, as no such trend is observed in any of the other samples.

Effect of pH on Color of Semi-Pure CASE

Figures 10A, 10B, 10C:
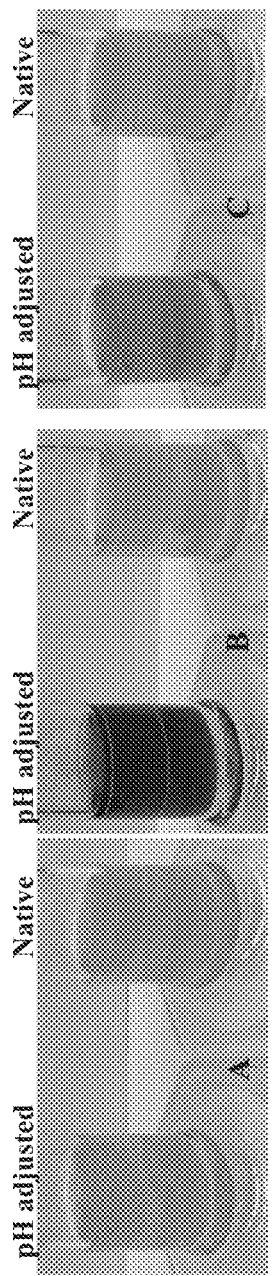
FIGS. 10A through 10C, depicts results of experimental examples demonstrating semi-pure CASE samples compared to a control sample.
Figure 11:
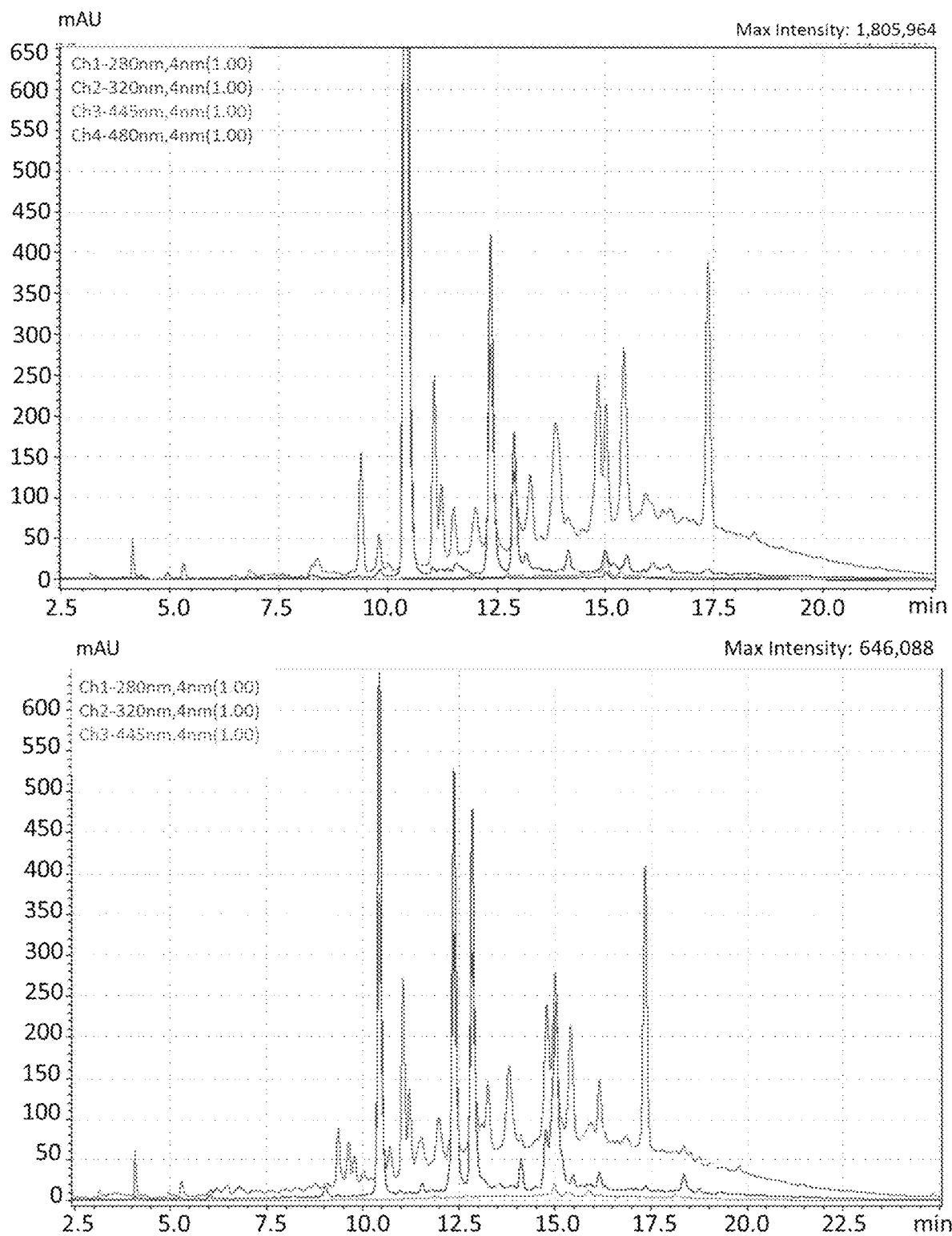
FIG. 11 depicts results of experimental examples demonstrating the full LC profile of the semi-pure CASE in water control sample (top) and base treated semi-pure CASE in water (bottom). The peak of interest, F12 appears at 15 min on both chromatograms. Line colors are pink, 280 nm; blue, 320 nm; green, 445 nm.
Figure 12:
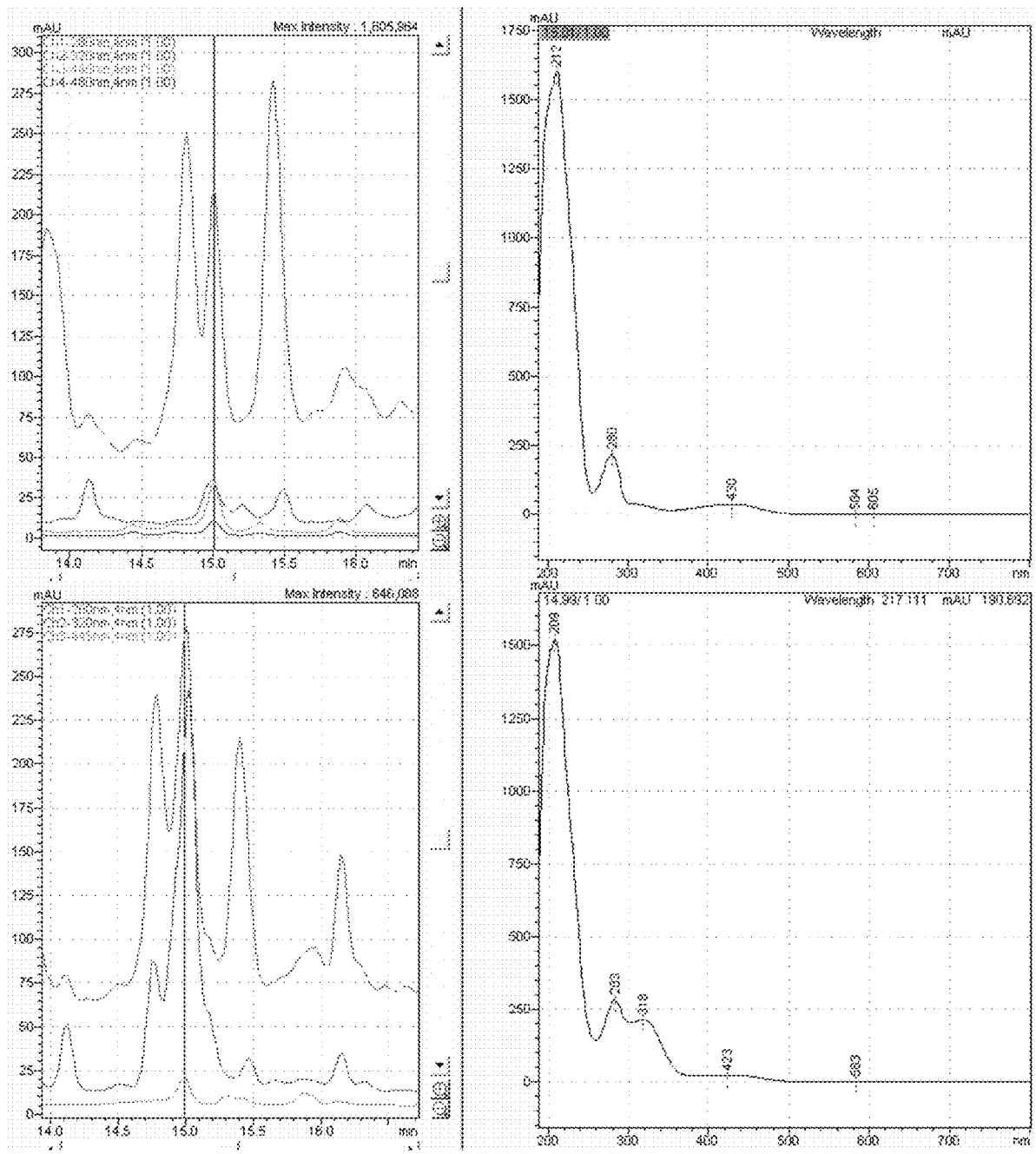
FIG. 12 depicts results of experimental examples demonstrating the LC profile and areas of maximum absorbance for F12 peak in semi-pure CASE in water (top) and pH adjusted semi-pure CASE in water. Line colors are pink, 280 nm; blue, 320 nm; green, 445 nm.

The effect of pH on raw CASE samples has been previously reported (Dabas et al., 2011. J. Food Sci 76:C1335-41; Dabas, 2012, Ph.D. Thesis, The Pennsylvania State University). Here, the effect of pH in semi-pure CASE is reported. Semi-pure CASE in water at a final concentration of 5 mg/mL has a pH of 3.32 and a yellow color (FIG. 10). Indeed, adjusting the pH to neutral levels again produced a deeper orange color, and increasing the pH to 10-12 created a dark red, and finally brownish red color. Upon returning the sample to its native pH range, and even lower to pH 1.59 produced a sample in which color was still pH dependent, but the color range had been shifted to a more orange-red range. Spec data showed an increase in sample absorbance at both 445 nm and 480 nm (FIG. 11). LC profiles showed that the most prominent colored peak, F12, was still present after treatment with base. The 280 nm profile remained as well, though decreased, while a substantial increase was seen in the 320 nm profile (FIGS. 11 and 12). This red-shift in color and increase in the 320 nm peaks indicates that there may be some extended conjugation forming in compounds where conjugation may have previously been limited.

Figure 13:
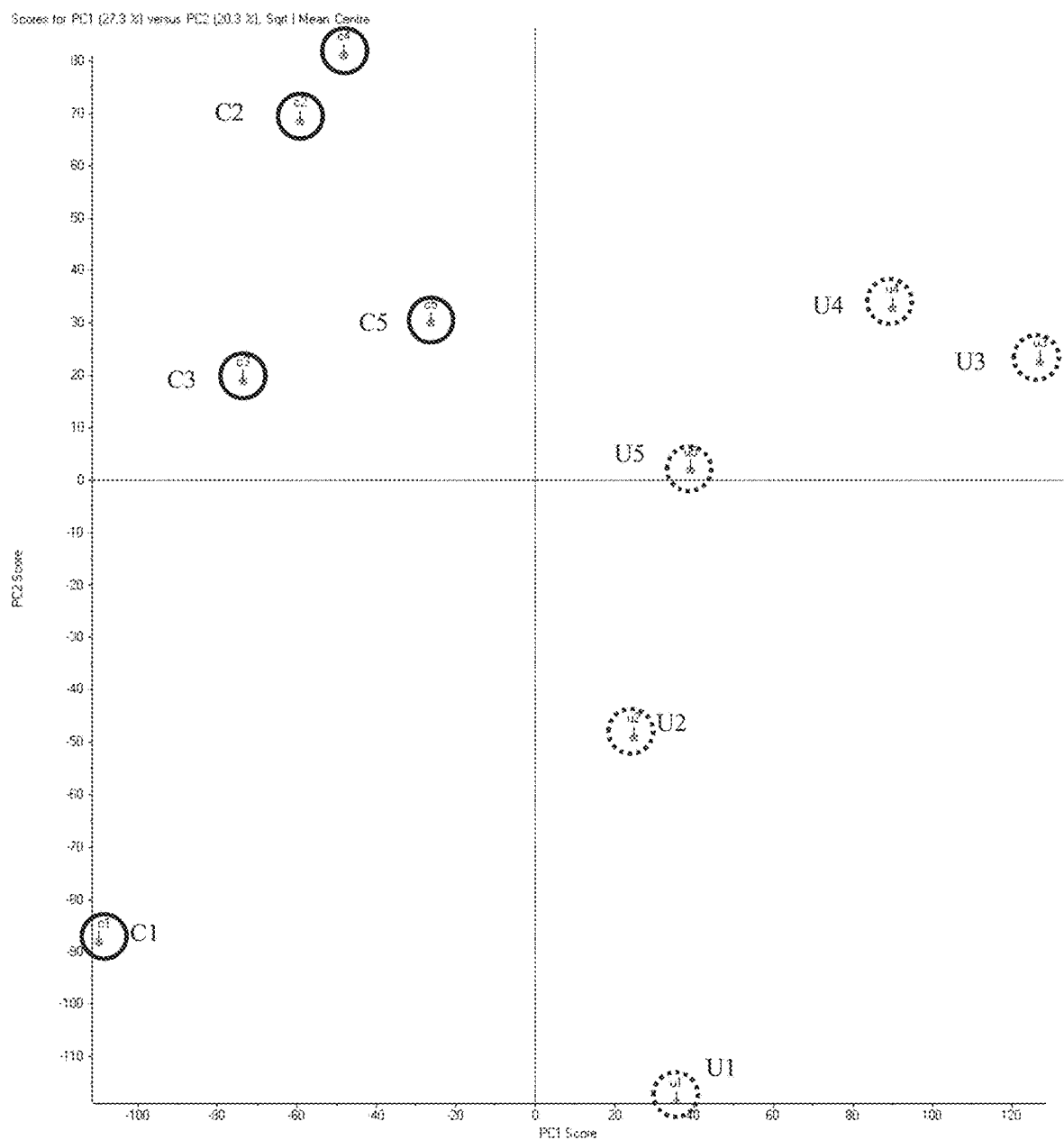
FIG. 13 depicts results of experimental examples demonstrating the PCA clustering scores for samples analyzed in positive mode.

Principal Component Analysis (PCA) of Colored and Uncolored Avocado Seed Extracts An uncolored avocado seed extract was prepared by inhibiting the action of PPO through the addition of tropolone. By comparing biological replicates of colored and uncolored extracts, it was possible to determine masses unique to each sample. FIG. 13 shows the clustering of masses in samples analyzed in positive mode. Variation between samples is common when analyzing natural products such as avocados, and that variation can be observed in this data by the divergence between clustering of replicates, as seen in FIG. 13.

Figure 14:
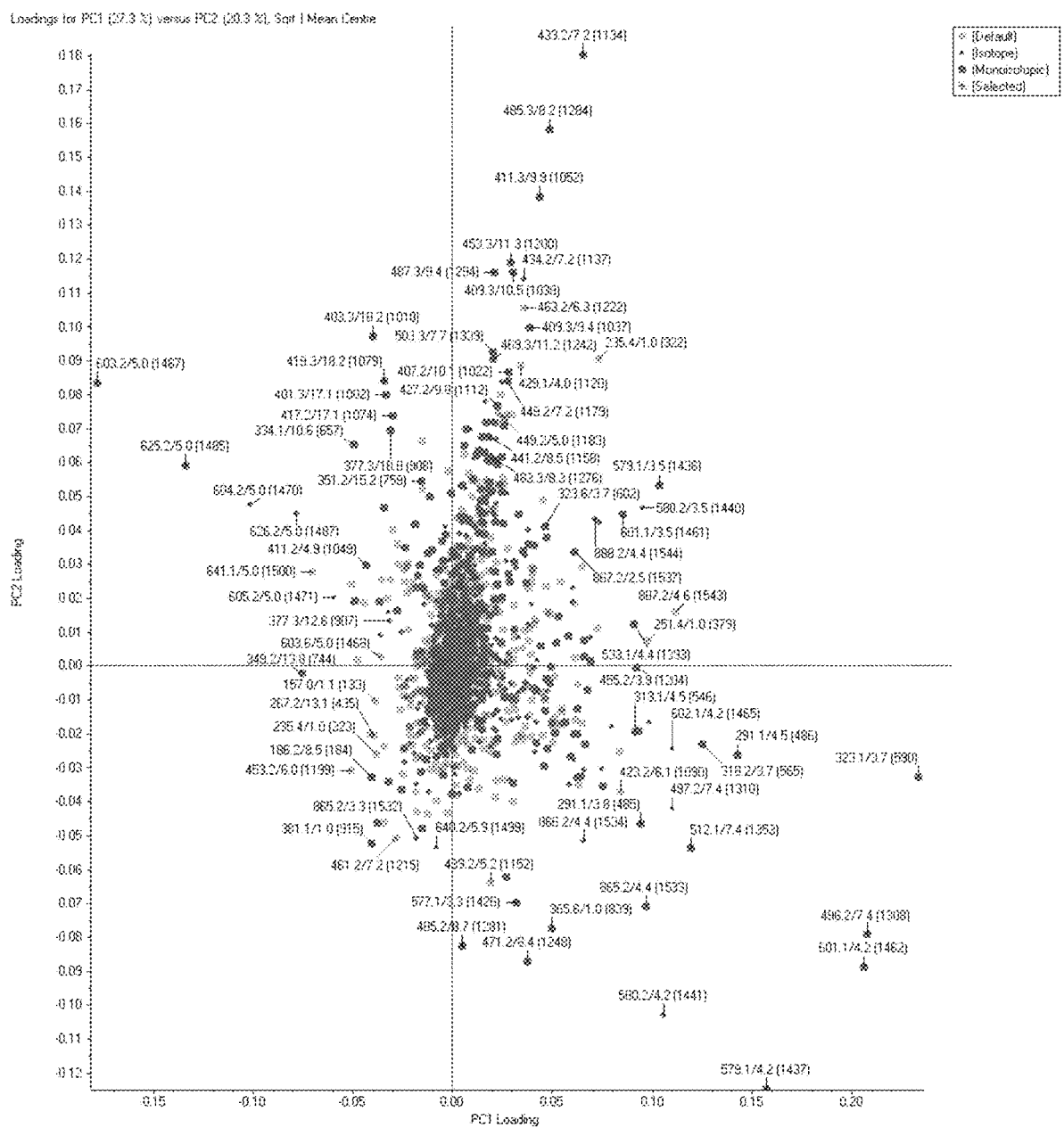
FIG. 14 depicts results of experimental examples demonstrating the PCA of colored and uncolored extracts in positive mode.
Figure 15:
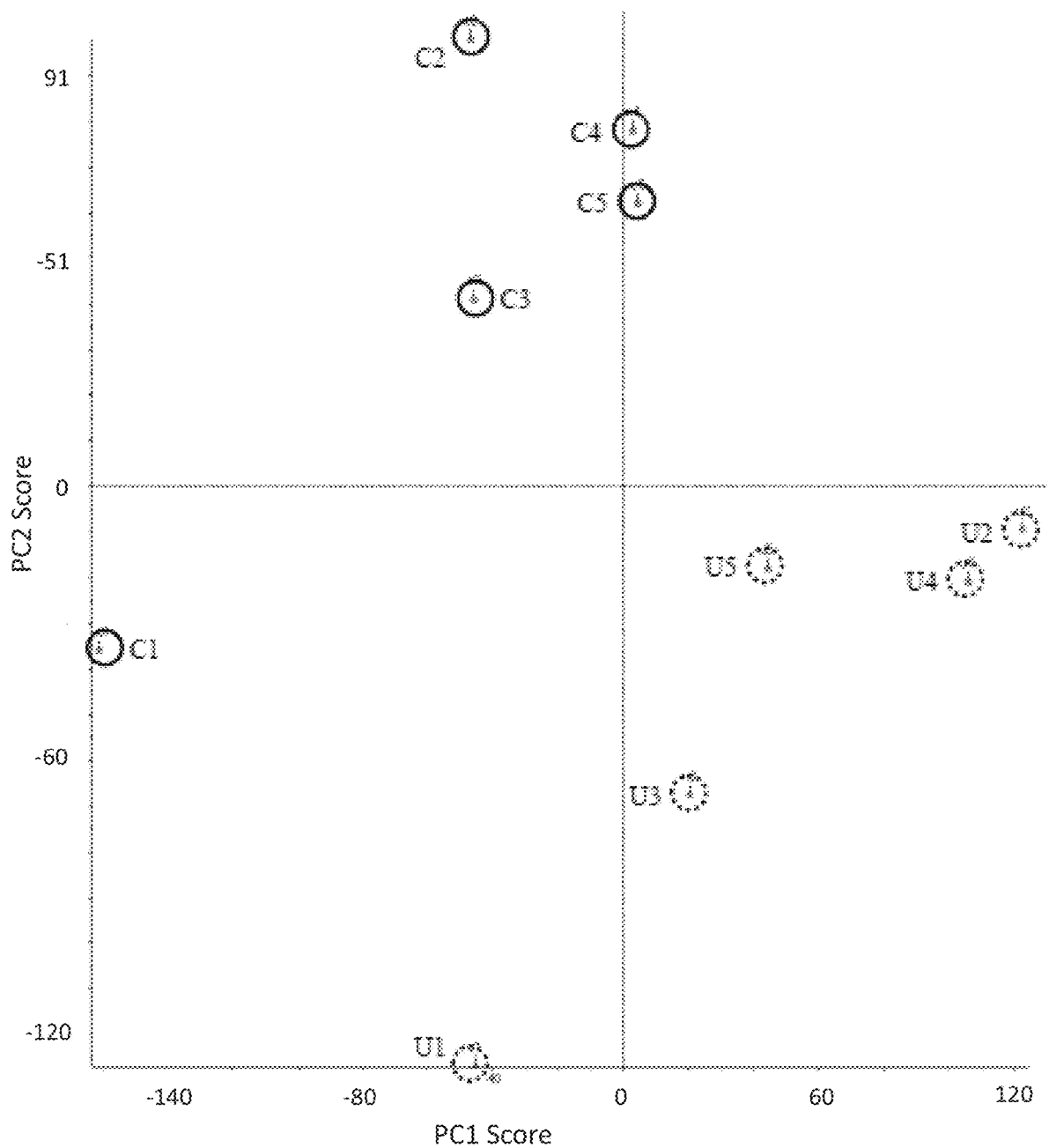
FIG. 15 depicts results of experimental examples demonstrating the PCA of colored (solid line) and uncolored (dashed line) extracts in positive mode.
Figure 16:
FIG. 16 depicts results of experimental examples demonstrating the PCA of colored and uncolored extracts in positive mode.

Masses near the upper left tended to be present at higher concentrations in the colored samples, while samples towards the lower right tended to be present at higher concentrations in the uncolored samples. FIG. 14 shows each unique mass found in the samples in positive mode. The clustering of samples analyzed in negative mode is shown in FIG. 15, while the total principal component analysis is shown in FIG. 16. Again masses near the upper left tended to be present at higher concentrations in the colored samples, while samples towards the lower right tended to be present at higher concentrations in the uncolored samples. Principal component analysis showed approximately forty-nine masses unique to the colored or uncolored extract. Abscisic acid, and perseitol, the 7-member sugar alcohol, were present in both extracts while epicatechin, catechin, procyanidin B2 and salidroside were found only in the uncolored extract. Table 2 shows a list of masses found to be unique to one the extracts.

TABLE 2

Compounds found in colored & uncolored avocado seed extracts via principal component analysis.

| Extract (Compound) | Retention time (min) | Mode | Molecular Ion | Fragments |
| --- | --- | --- | --- | --- |
| Both (perseitol) | 0.96 | negative | 211.082 | 193.0171, 149.0457, 131.0353, 119.0347, 113.0243, 101.025, 89.0255, 85.0309, 71.0163, 59.0173, 57.038, 55.0227 |

TABLE 2-continued

Compounds found in colored & uncolored avocado seed extracts via principal component analysis.

| Extract (Compound) | Retention time (min) | Mode | Molecular Ion | Fragments |
|---|---|---|---|---|
| Both (abcsisic acid) | 4.05 | positive | 265.1413 | 247.1325, 135.134, 229.1225, 219.1386, 217.1219, 211.1116, 203.1054, 196.0858, 187.1131, 175.0743, 161.0945, 147.0797, 135.0791, 128.0619, 115.0552, 95.0498, 91.0547 |
| Uncolored (epicatechin/ catechin) | 4.51 | negative | 289.073 | 271.0623, 247.0636, 245.0829, 227.0725, 221.0833, 205.0518, 203.0726, 187.0408, 161.0616, 159.0459, 151.0404, 137.0252, 125.0247, 123.0456, 109.0303, 97.0303, 95.051 |
| Uncolored (catechin/ epicatechin) | 3.76 | negative | 289.0726 | 245.0828, 123.0459, 109.031 |
| Uncolored (Procyanidin B2) | 4.17 | positive | 579.1484 | 439.1004, 427.1019, 411.1085, 409.0885, 303.0826, 301.0698, 291.0857, 289.0682, 287.0547, 259.0612, 247.0601, 229.0499, 215.0698, 205.0465, 201.0542, 191.0333, 187.0373, 179.0321, 177.0547, 175.0398, 167.0334, 165.0542, 163.0382, 159.0445, 149.0222, 147.0443, 139.0381, 135.0439, 127.039, 123.0435, 109.0304, 68.9977 |
| Uncolored (salidroside) | 3.67 | positive | 323.1096 | None |
| uncolored | 3.64 | negative | 299.1134 | 179.0547, 137.061, 119.0494, 101.0245, 89.025, 71.0155 |
| uncolored | 3.64 | negative | 345.1193 | 299.1134, 179.0561, 161.0457, 137.0613, 119.0439, 113.0249, 89.0255, 71.0157, 59.0168 |
| uncolored | 2.45 | negative | 575.127 | 557.1182, 531.1353, 513.41, 487.143, 449.0897, 423.0757, 407.0825, 363.0927, 351.0499, 327.0516, 325.0733, 309.0438, 307.0617, 287.0576, 243.0306, 241.0524, 217.0513, 175.041, 167.0355, 125.0245 |
| uncolored | 3.86 | negative | 431.1571 | 299.1094, 191.0582, 149.047, 119.05, 99.0113, 89.0259, 71.0144, 59.0145 |
| uncolored | 4.52 | negative | 357.0588 | 311.0537, 289.0721, 245.0821, 203.0711, 137.0245, 109.0302 |
| uncolored | 5.8 | negative | 437.0509 | 419.0418, 391.049, 285.3968, 285.0378, 284.0348, 283.0264, 227.0345, 171.0448, 151.0035, 123.0059 |
| uncolored | 4.16 | negative | 577.1356 | 451.1055, 425.0901, 407.0788, 339.0898, 289.0725, 287.0565, 245.0819, 203.0691, 137.0238, 125.0244 |
| uncolored | 3.43 | negative | 577.1423 | 559.1265, 457.1053, 425.0921, 407.0798, 339.0899, 289.0736, 245.0829, 161.0252, 125.0248 |
| uncolored | 2.42 | negative | 863.1943 | 711.1417, 693.1323, 649.1332, 575.1234, 513.123, 449.0925, 407.0818, 297.0422, 287.0565, 243.0302, 167.0353 |
| uncolored | 6.04 | negative | 597.1882 | 477.1443, 357.1041, 345.1067, 339.0859, 315.0899, 233.0458, 209.0467, 191.0366, 167.0354, 125.0244 |
| uncolored | 7.37 | negative | 540.149 | 494.1429, 472.1618, 472.1854, 350.0873, 321.0949, 254.043, 232.0646, 212.0338, 172.0403, 144.0457, 132.0454 |
| uncolored | 5.8 | negative | 575.1223 | 539.101, 449.0882, 423.0769, 407.0779, 327.0521, 289.0725, 287.0548, 285.0419, 177.0193, 175.0397, 163.0038, 125.0247 |
| uncolored | 4.17 | positive | 601.1302 | 449.0829, 431.716, 311.0526 |
| uncolored | 7.4 | positive | 496.157 | none |

TABLE 2-continued

Compounds found in colored & uncolored avocado seed extracts via principal component analysis.

| Extract (Compound) | Retention time (min) | Mode | Molecular Ion | Fragments |
|---|---|---|---|---|
| uncolored | 4.53 | positive | 291.0866 | 207.0651, 165.0548, 161.0593 |
| uncolored | 3.67 | positive | 318.1545 | 265.1079, 247.0967, 229.0857, 147.0437, 139.0387, 123.0439, 115.0543, 111.0441, 91.0552, 77.0399, 65.0406, 55.0207 |
| uncolored | 7.4 | positive | 512.1319 | none |
| Uncolored | 4.42 | positive | 865.1955 | 713.1505, 695.1389, 575.1172, 205.0844, 187.0751, 163.0598, 145.0497, 127.0387, 121.0653, 85.0299, 77.0401, 69.0351, 57.036, 53.0416 |
| Uncolored | 3.8 | positive | 291.0859 | 207.0643, 179.0682, 165.0539 |
| Uncolored | 3.67 | positive | 470.1613 | 399.0965, 339.0746, 320.1014, 161.0598, 147.0436, 139.0388, 123.0439, 119.0485, 115.0544, 111.0438, 91.0554, 77.0391 |
| Uncolored | 4.53 | positive | 313.0674 | 279.0533 |
| Uncolored | 4.64 | positive | 575.1019 | 539.098, 529.134, 279.0533, 261.0269, 251.0664, 219.0314, 201.0065, 177.0222, 170.406, 158.9965, 140.9861, 121.0652, 98.9752, 77.0406 |
| Uncolored | 1.04 | positive | 365.6434 | 203.052, 185.0414 |
| Uncolored | 8.35 | positive | 471.2209 | 335.095 |
| Uncolored | 3.33 | positive | 577.1332 | 541.1306, 451.0998, 449.0806 |
| Uncolored | 3.66 | positive | 385.081 | 339.3446 |
| Uncolored | 4.56 | positive | 330.0386 | 311.4504, 279.0465, 237.0408, 201.0073, 175.005, 163.006, 126.969, 110.9749, 98.9766, 68.9664 |
| Uncolored | 4.03 | positive | 617.6813 | 311.0522, 287.0526, 191.0045, 173.019, 160.9945, 140.0411, 139.0389 |
| Uncolored | 4.53 | positive | 329.041 | 190.9962, 172.9939, 160.988 |
| Uncolored | 7.4 | positive | 336.107 | 192.0642, 174.0522, 146.0596, 132.9961 |
| Uncolored | 5.27 | positive | 383.1665 | 221.1129, 128.049 |
| Uncolored | 3.9 | positive | 471.1259 | None |
| Uncolored | 4.8 | positive | 577.1338 | 559.1175, 451.0739, 435.0754, 409.0917, 301.0684, 289.0726, 275.0703, 271.0583, 245.0411, 163.0373, 123.0434 |
| Colored | 4.99 | negative | 603.1596 | 449.1087, 439.1136, 421.0948, 299.0563, 271.0261, 259.0621, 175.04 |
| Colored | 4.99 | negative | 623.1428 | 471.0916, 449.1119, 381.0565, 293.0443, 269.0619, 269.0464, 227.0335 |
| colored | 3.34 | negative | 447.1531 | 315.108, 191.0565, 174.9567, 135.0455, 89.0257 |
| colored | 4.96 | negative | 733.2036 | 581.1564, 571.1712, 439.1058, 421.0892, 259.0599 |
| colored | 5.18 | negative | 887.2102 | 725.1714, 449.1034, 394.0628 |
| colored | 4.99 | negative | 691.1336 | 645.1358, 623.1358, 623.1447, 539.0832, 471.0935, 449.1107, 381.0565, 309.0367, 293.4312, 269.0458, 225.0515 |
| colored | 4.99 | negative | 601.4094 | none |
| colored | 10.59 | positive | 334.1114 | 306.1059, 230.0734, 229.0682 |
| colored | 5.01 | positive | 625.6052 | 473.1048, 311.0514, 203.0624, 127.0308, 126.0243, 105.0458, 77.0403, 58.9978, 51.0265 |
| colored | 5.01 | positive | 603.169 | 451.1201, 441.1167, 395.1102, 289.0697, 271.0589, 243.0636, 215.0697, 147.0432 |

Structure Elucidation

Figure 17:
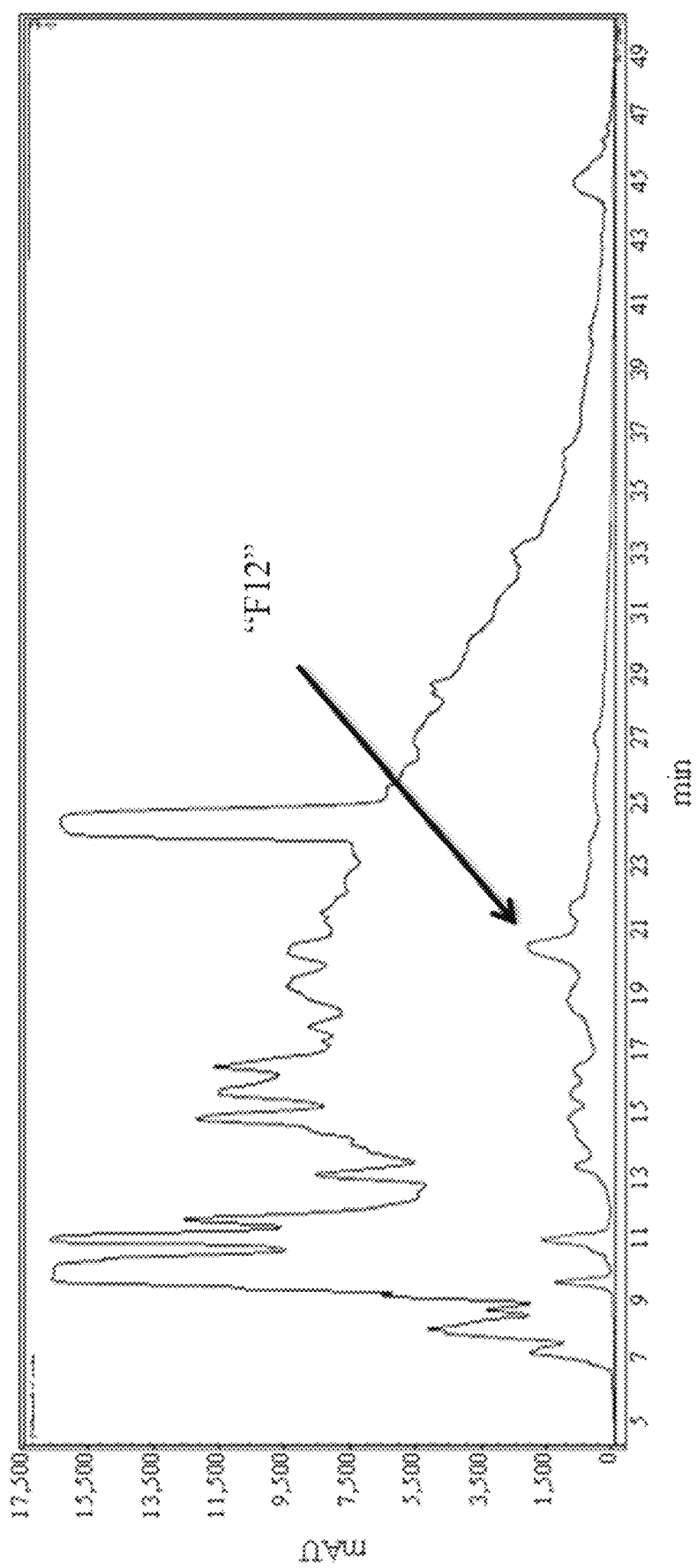
FIG. 17 depicts results of experimental examples of the HPLC chromatograph of the semi-pure, post-amberlite CASE. Samples were analyzed at 280 nm (top, black) and at 445 nm (bottom, red).
Figure 18:
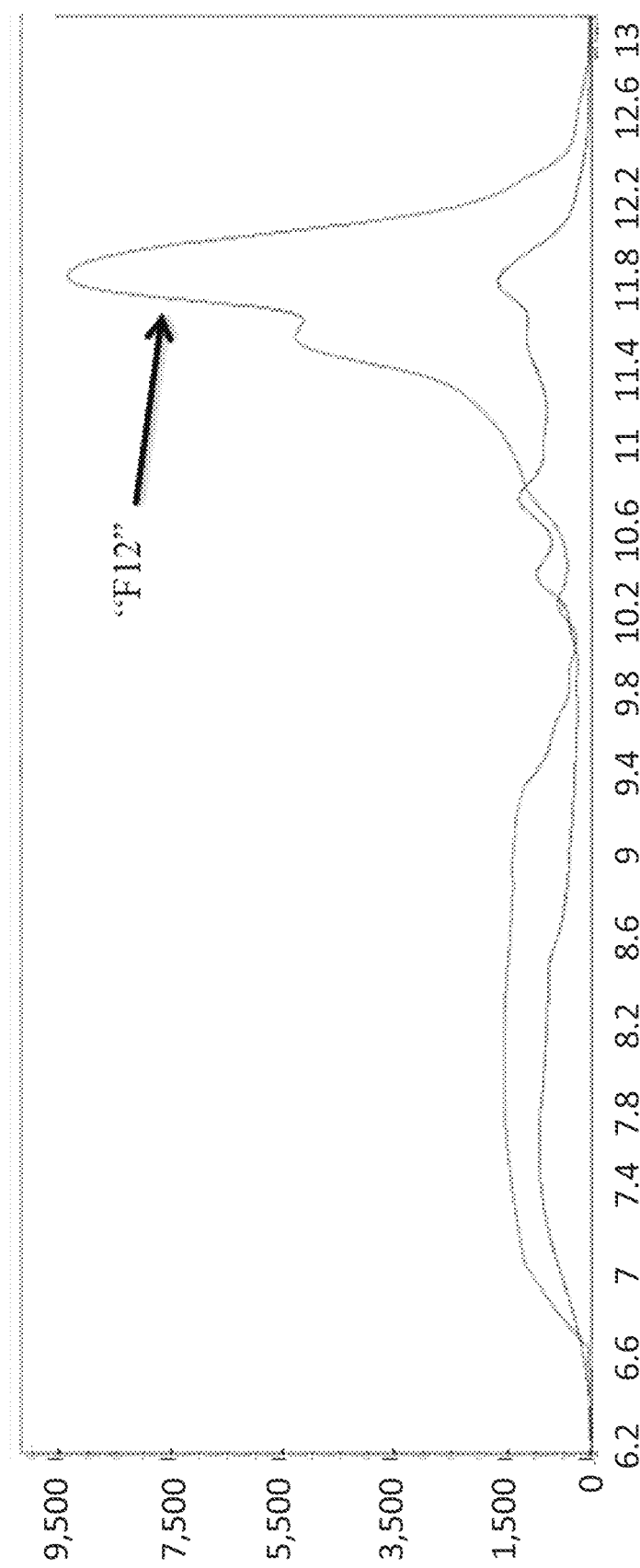
FIG. 18 depicts results of experimental examples of the HPLC chromatograph post-C18 rough F12. Samples were analyzed at 280 nm (bottom, black) and at 445 nm (top, red).
Figure 19:
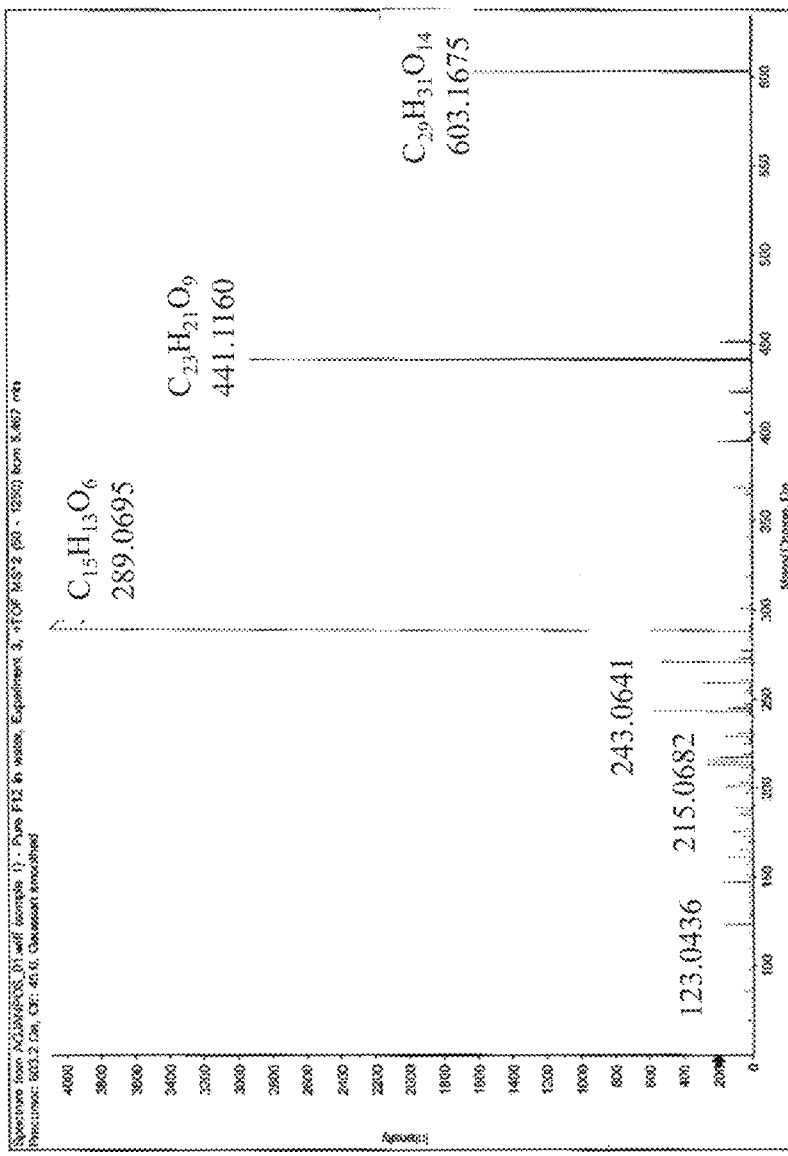
FIG. 19 depicts results of experimental examples demonstrating the MS/MS analysis indicated a $[M+H]^+$ 603.1675 parent peak.
Figure 20:
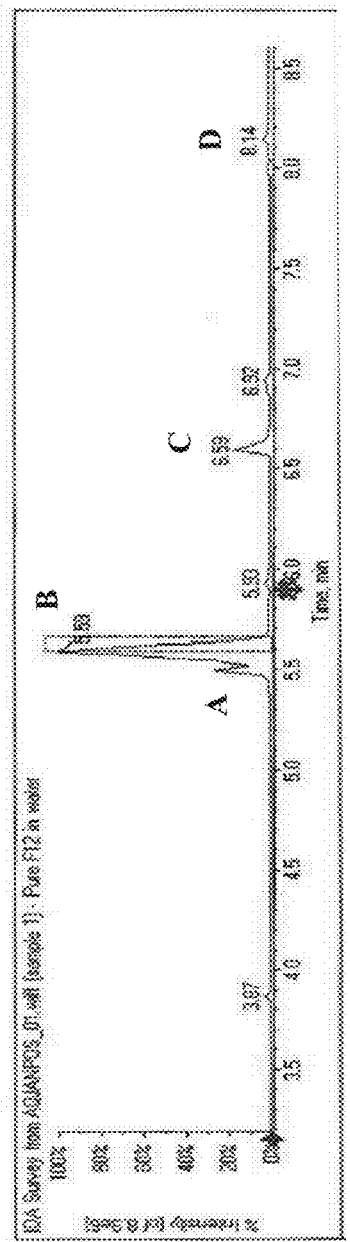
FIG. 20 depicts results of experimental examples demonstrating analysis of pure F12 included a $[M+H]^+$ 917.2639 peak (A), the compound of interest, $[M+H]^+$ 603.1675 peak (B), a $[M+H]^+$ 603.1687 peak (C), and $[M+H]^+$ 1205 dimer produced from the combination of two $[M+H]^+$ 603 compounds (D).
Figure 21:
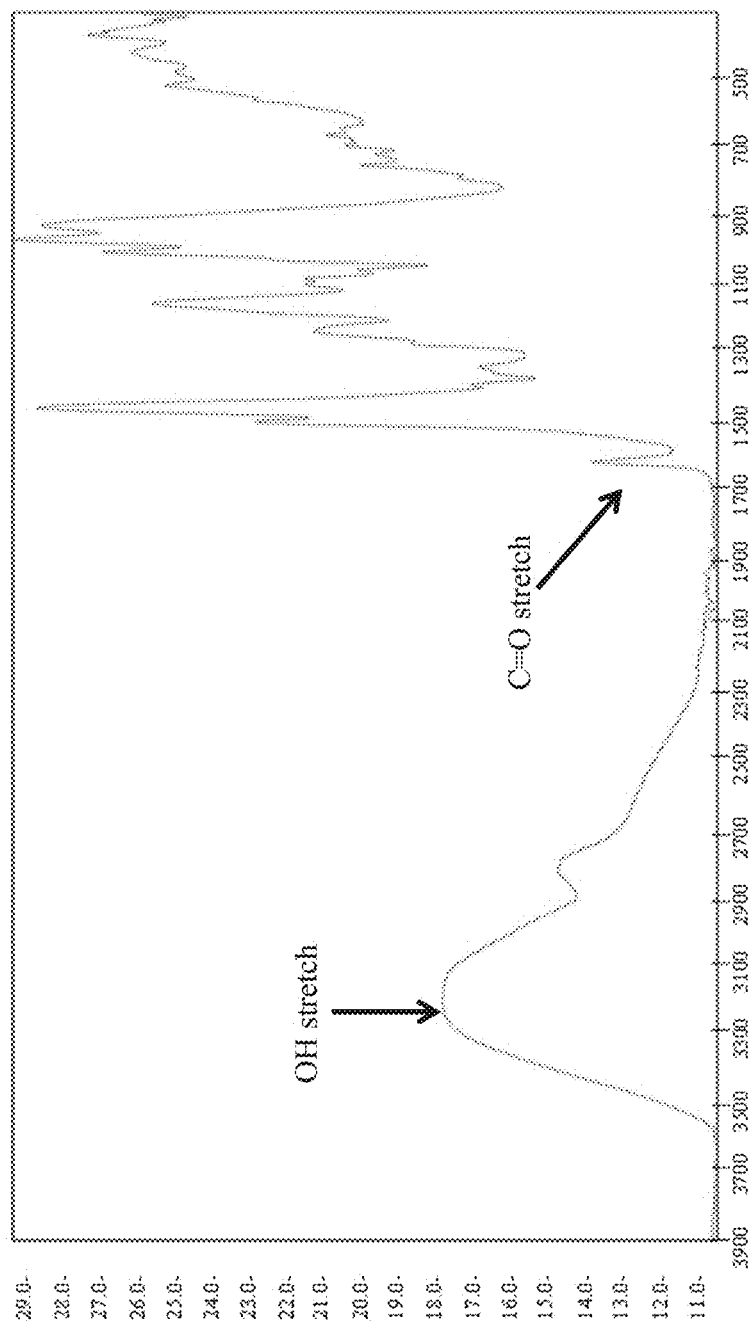
FIG. 21 depicts results of experimental examples demonstrating the ATR-FTIR analysis of "pure F12," the most prominent colored compound.
Figure 22:
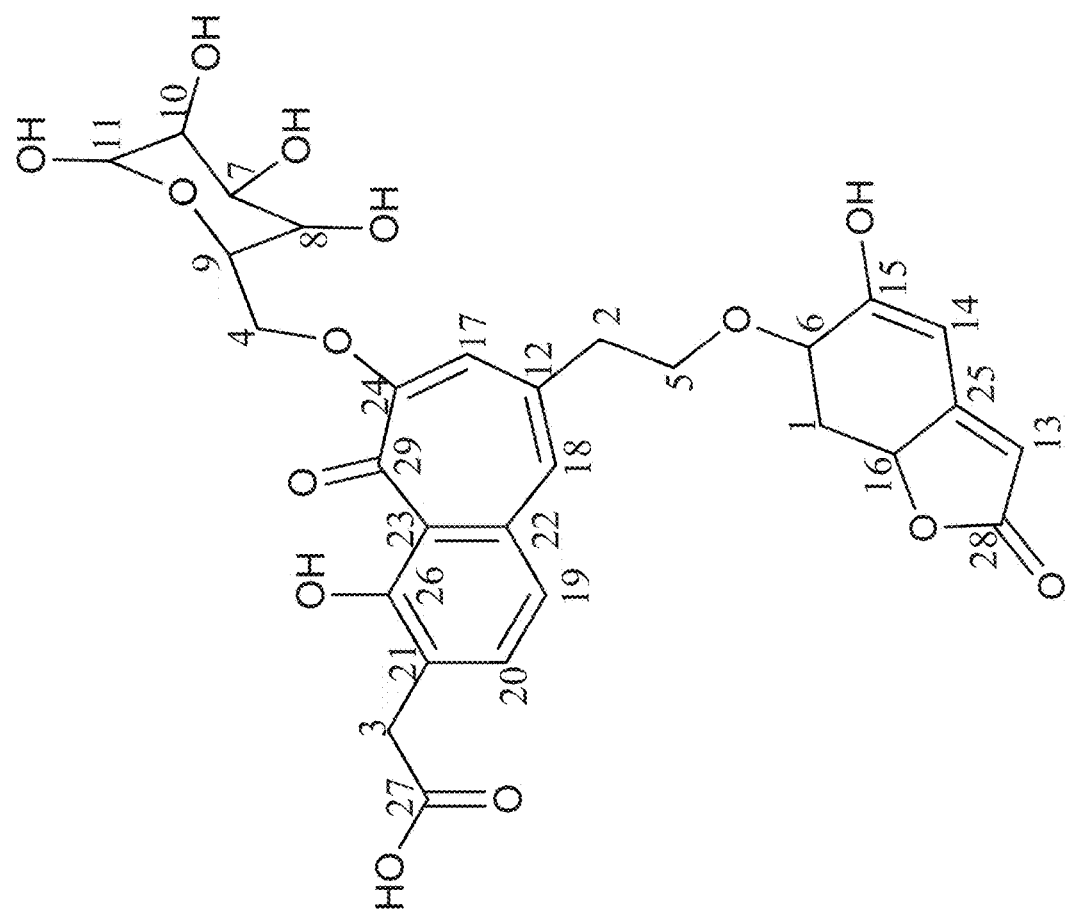
FIG. 22 depicts results of experimental examples showing the structure of the most prominent colored compound, F12.
Figure 23:
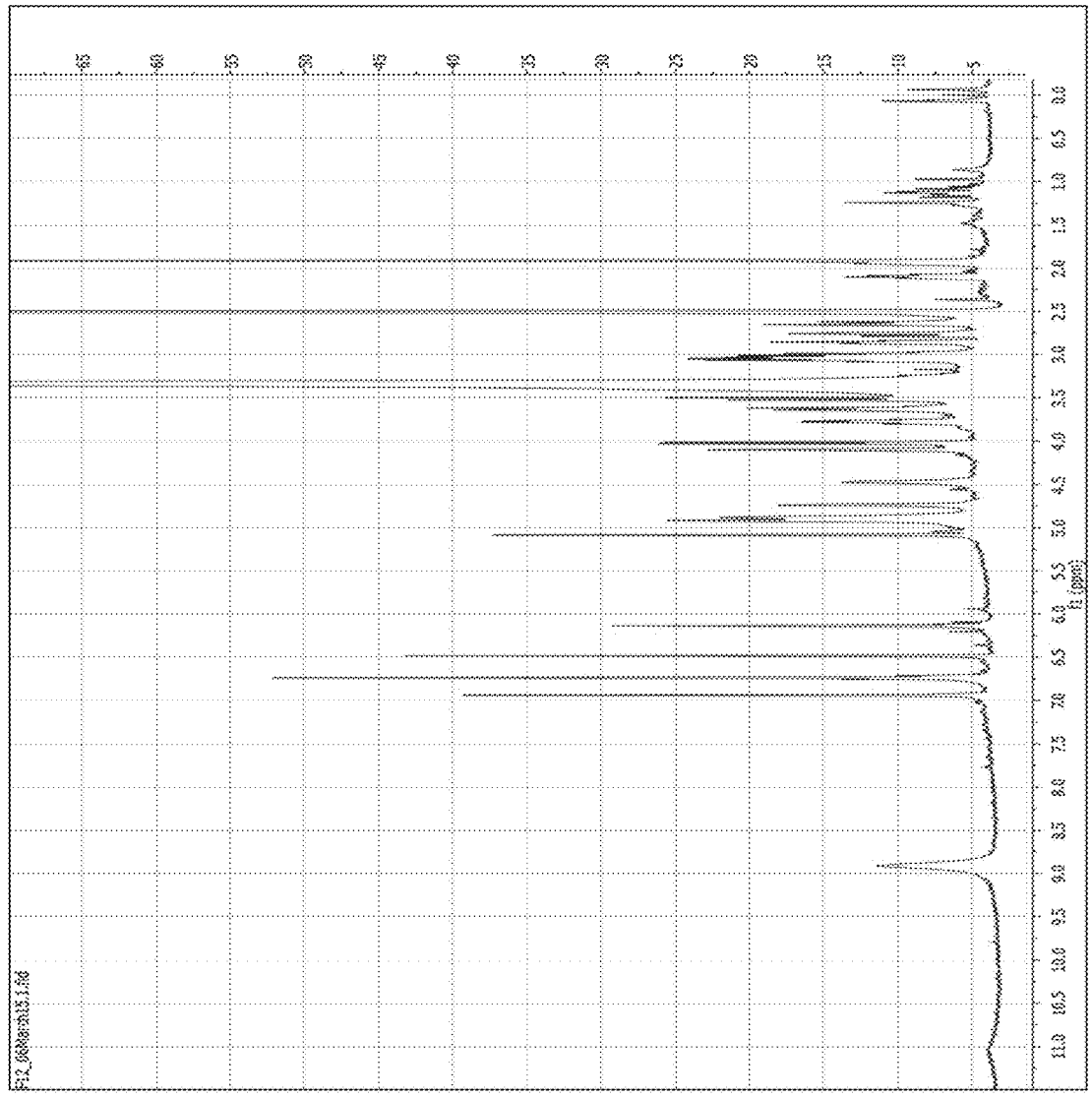
FIG. 23 depicts the $^1H$ NMR spectrum of F12 in $(CD_3)_2SO$.
Figure 24:
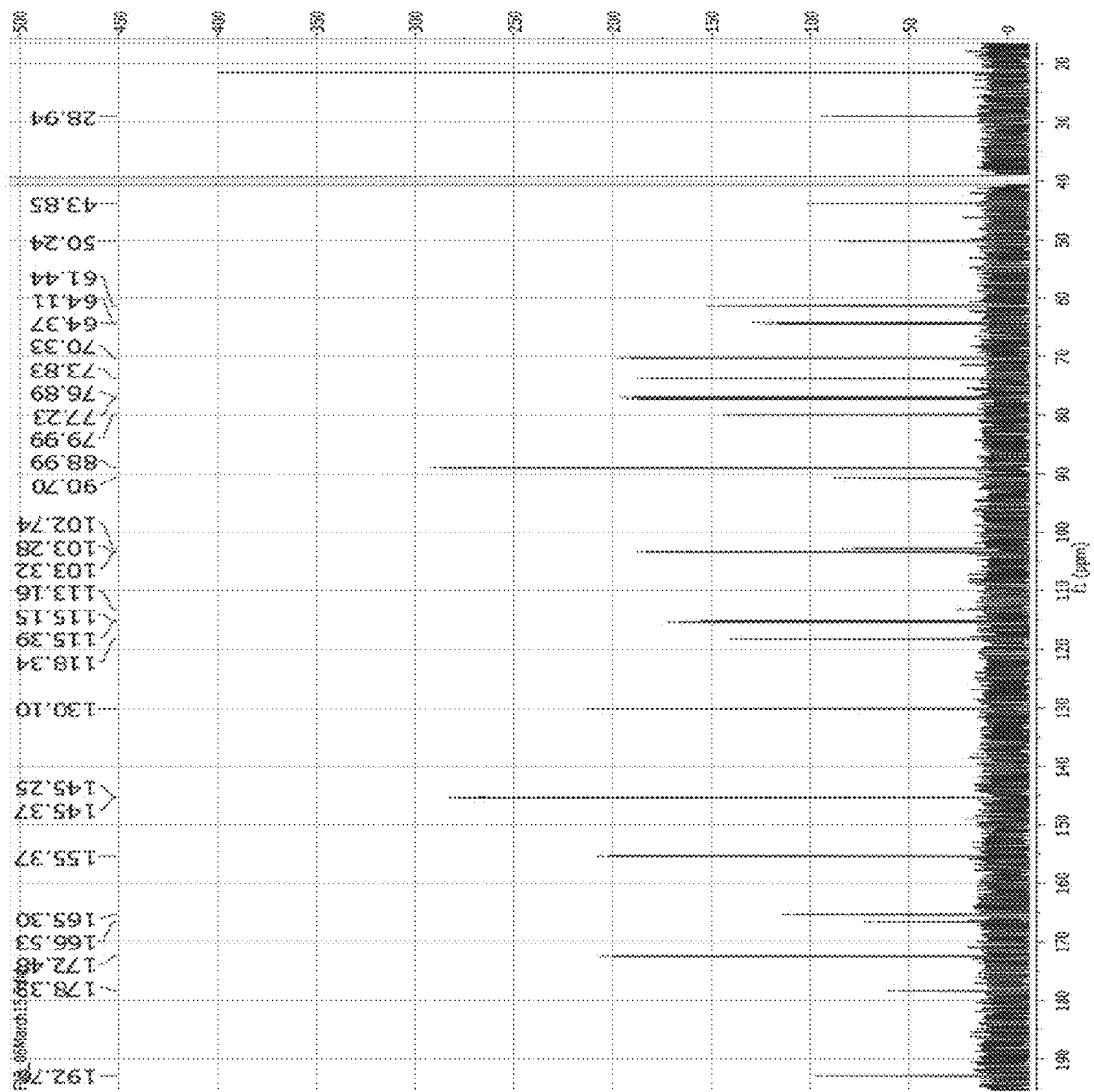
FIG. 24 depicts the $^{13}C$ NMR spectrum of F12 in $(CD_3)_2SO$.
Figure 25:
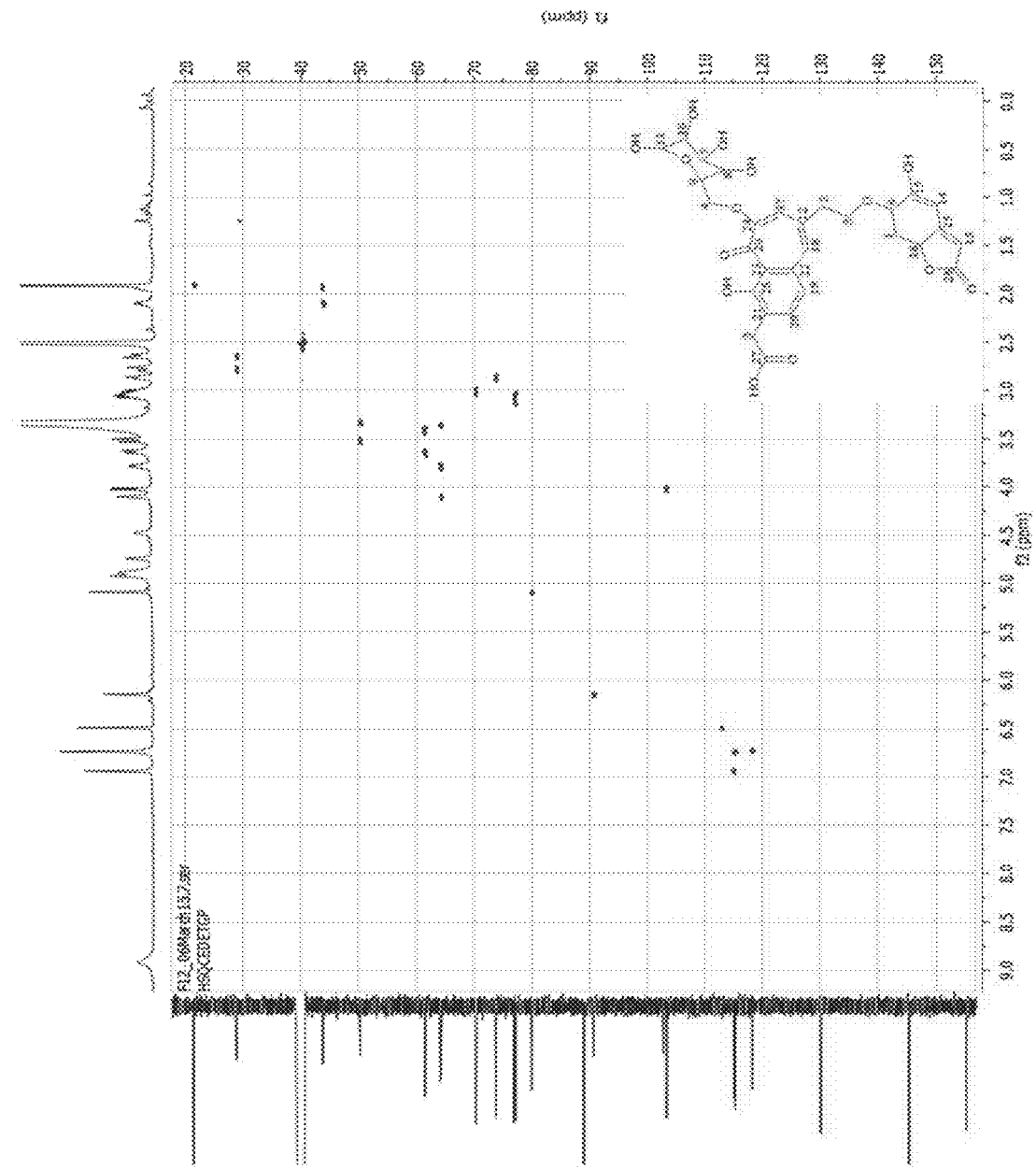
FIG. 25 depicts the DEPT-edited HSQC spectrum of F12 in $(CD_3)_2SO$.

Purifying the extract consisted of multiple chromatographic steps. As is customary with natural products, changes in the LC profile where encountered between seed batches. The initial purification step was filtration and purification with amberlite, leading to a redder extract (~29% yield). The semi-pure, post-amberlite extract was then purified using a preparatory C18 HPLC column (FIG. 17). A single fraction from that analysis, F12, was further purified using a Restek ultra aromax preparatory HPLC column (FIG. 18). The compound eluted as the second of two overlapping compounds. The pure F12 sample, collected from the ultra aromax column, was analyzed via high resolution MS/MS. F12 was found to be a yellow solid. Total concentration in seed extract was not calculated due to the limited quantity, but it is believed to be in the low PPB range. HRMS calculated molecular formula for 603.1675 the peak was $C_{29}H_{31}O_{14}$. An abundant m/z 441.1160 fragment (Δm/z 162), indicated the presence of a glucose moiety (FIG. 19). After passing through 3-6 purification steps, the extract still retained some impurities including another $[M+H]^+$ 603.1687 compound, an $[M+H]^+$ 917.2639 compound containing an m/z 603 moiety, and finally an $[M+H]^+$ 1205 dimer produced from the combination of two $[M+H]^+$ 603 compounds (FIG. 20). Full MS data for the purified compound F12 are listed below. The spectrum is shown in FIG. 19. The MS m/z (relative intensity) was 603.1675 (42.1%), 441.1160 (74.4%), 289.0695 (100%), 243.0641 (15.2%), 215.0682 (7.3%), 123.0436 (4.9%). Attenuated Total Reflectance Fourier Transform Infrared spectroscopy (ATR-FTIR) analysis showed a broad OH band at 3300 cm$^{-1}$ and a peak at 1740 cm$^{-1}$ indicating the presence of a C=O stretch (FIG. 21). The full ATR data for purified F12 is as follows. IR (cm$^{-1}$): 3300, 2900, 1740, 1640, 1580, 1475, 1350, 1300, 1200, 1120, 1100, 1030, 850, 800, 650, 550, 500. Based on the above data, as well as high resolution NMR analysis, the compound was found to be a glycosylated benzotropolone with multiple side chains, having a molecular formula of $C_{29}H_{30}O_{14}$ (FIG. 22). A summary of the NMR data for F12 can be seen in Table 3. Spectra from samples in $(CD_3)_2SO$ can be seen in FIGS. 23-28.

TABLE 3

NMR Correlations of F12 in $(CD_3)_2SO$

| Position | C ppm | H ppm | HMBC | COSY |
|---|---|---|---|---|
| 1* | 28.9362 | 2.777, 2.647 | | 6, 16 |
| 2* | 43.8557 | 2.099, 1.943 | | 5 |
| 3* | 50.2423 | 3.523, 3.338 | | |
| 4* | 61.442 | 3.639, 3.400 | 29 | |
| 5* | 64.1187 | 3.782, 3.364 | | 2 |
| 6* | 64.3734 | 4.1 | | 1 |
| 7* | 70.3375 | 3 | 10 | |
| 8* | 73.8364 | 2.86 | 10 | |
| 9 | 76.8902 | 4.47 | | 4 |
| 10* | 77.2339 | 3.05 | 7, 8 | |
| 11* | 79.9933 | 5.09 | | |
| 12 | 88.9941 | | 2, 17 | |
| 13* | 90.704 | 6.14 | 14, 25 | |
| 14 | 102.7507 | | 13 | |
| 15 | 103.2829 | | 1 | |
| 16* | 103.331 | 4.01 | | 1 |
| 17* | 113.1622 | 6.49 | | |
| 18* | 115.1565 | 6.94 | | |
| 19* | 115.3991 | 6.75 | | |
| 20* | 118.3498 | 6.73 | 18 | |
| 21 | 130.1123 | | 19, 20 | |
| 22 | 145.2667 | 8.91 | 19, 20 | |
| 23 | 145.3811 | 8.91 | 18 | |
| 24 | 155.383 | | | |
| 25 | 165.3164 | | 13 | |
| 26 | 166.5427 | | 3 | |
| 27 | 172.4969 | | | |
| 28 | 178.3405 | | | |
| 29 | 192.7777 | | 4 | |

The full data for F12 in $(CD_3)_2SO$ are listed below. Additional experiments were conducted on F12 dissolved in $D_2O$, however it was primarily the $(CD_3)_2SO$ data that were used in assigning positions in the structure. Data of F12 in $D_2O$ can be found in FIG. 30-36.

Due to structurally similar impurities in F12, some additional peaks are expected and may be due to these contaminates. The $^1H$ NMR spectra (FIG. 23) (500 MHz, $(CD_3)_2SO$) shows δ 8.91 (s, 2H), 6.94 (s, 1H), 6.74 (dd, 2H), 6.48 (s, 1H), 6.14 (s, 1H), 5.08 (s, 1H), 4.90 (d, J=15.5 Hz, 1H), 4.14-4.06 (m, 2H), 4.02 (d, J=7.7 Hz, 1H), 3.78 (td, J=9.3, 6.1 Hz, 1H), 3.63 (d, J=11.7 Hz, 1H), 3.51 (d, J=14.6 Hz, 1H), 3.33 (m, 3H), 3.03 (dp, J=25.5, 9.3, 8.9 Hz, 1H), 2.86 (t, J=8.3 Hz, 1H), 2.77 (dd, J=16.6, 4.0 Hz, 1H), 2.64 (d, J=16.0 Hz, 1H), 2.10 (ddd, J=14.5, 8.6, 5.7 Hz, 1H), 1.91 (m, 1H). The proton spectrum (FIG. 23) showed many multiplets in the 5-2 ppm region, indicative of sugar protons and OH groups. There are five $CH_2$ groups, however, for those groups on carbons 3, 4, and 5, one proton signal from each $CH_2$ group is hidden by a large water peak at approximately 3 ppm, making them difficult to identify. The spectrum also showed a very broad, low intensity peak near 11 ppm. This peak is likely to be due to the interaction between the OH on C26 and the C=O at C29. These HO—O=C correlations have been observed in similar compounds, often appearing very downfield around 10-13 ppm. It was necessary to use $(CD_3)_2SO$ and $D_2O$ as solvents due to low solubility of F12 in any organic solvent. Unfortunately these solvents cause some difficulties when trying to identify $CH_2$ protons, and the many OH groups which possess protons which exchange rapidly in these solvents, leading to a decrease in the intensity of their signals.

In the carbon spectrum (FIG. 24), 30 peaks were found, 29 of which were assigned to F12. Assigned peaks are marked. Specifically, the peaks are assigned as follows δ 192.76 (C=O, C29), 178.33 (C=O, C28), 172.48 (C=O, C27), 166.53 (C26), 165.30 (C25), 155.37 (C24), 145.37 (C23), 145.25 (C22), 130.10 (C21), 118.34 (CH, C20), 115.39 (CH, C19), 115.15 (CH, C18), 113.16 (CH, C17), 103.32 (CH, C16), 103.28 (C15), 102.74 (CH, C14), 90.70 (CH, C13), 88.99 (C12), 79.99 (CH, C11), 77.23 (CH, C10), 76.89 (CH, C9), 73.83 (CH, C8), 70.33 (CH, C7), 64.37 (CH, C6), 64.11 ($CH_2$, C5), 61.44 ($CH_2$, C4), 50.24 ($CH_2$, C3), 43.85 ($CH_2$, C2), 28.94 ($CH_2$, C1). A carbon at 113.16 ppm had a broad signal of very low intensity, possibly because of a short $T_2$ relaxation time, however, correlations in both the DEPT-edited-HSQC as well as in the HMBC, prove that it was a true peak, the carbon of which belonged to F12. DEPT-edited-HSQC confirmed sixteen carbon-hydrogen connections, including the presence of five $CH_2$ groups, indicated by red (negative) signals in FIG. 25.

Figure 26:
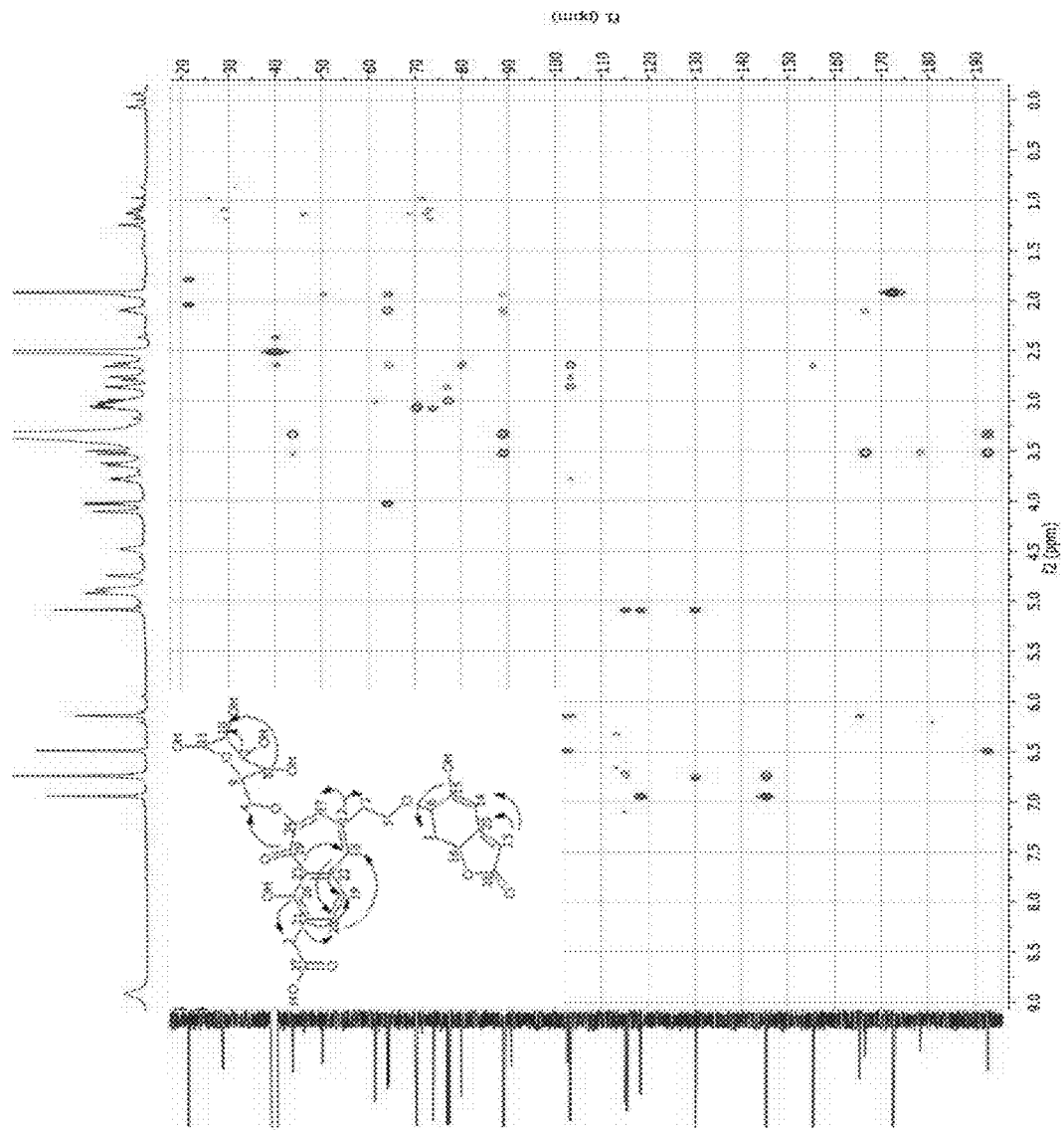
FIG. 26 depicts the HMBC NMR spectrum, of F12 in $(CD_3)_2SO$. Arrows on the structure indicate correlations.
Figure 27:
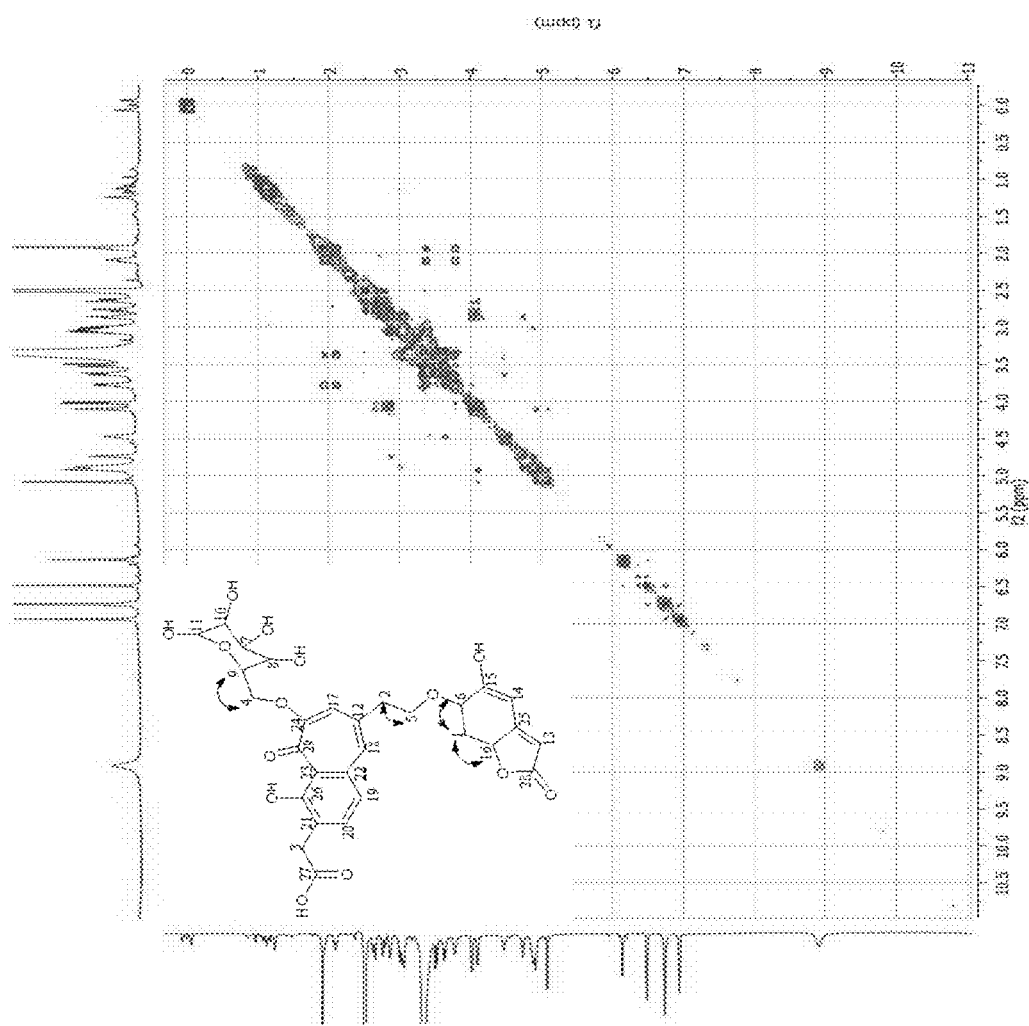
FIG. 27 depicts the COSY analysis of F12 in $(CD_3)_2SO$.
Figure 28:
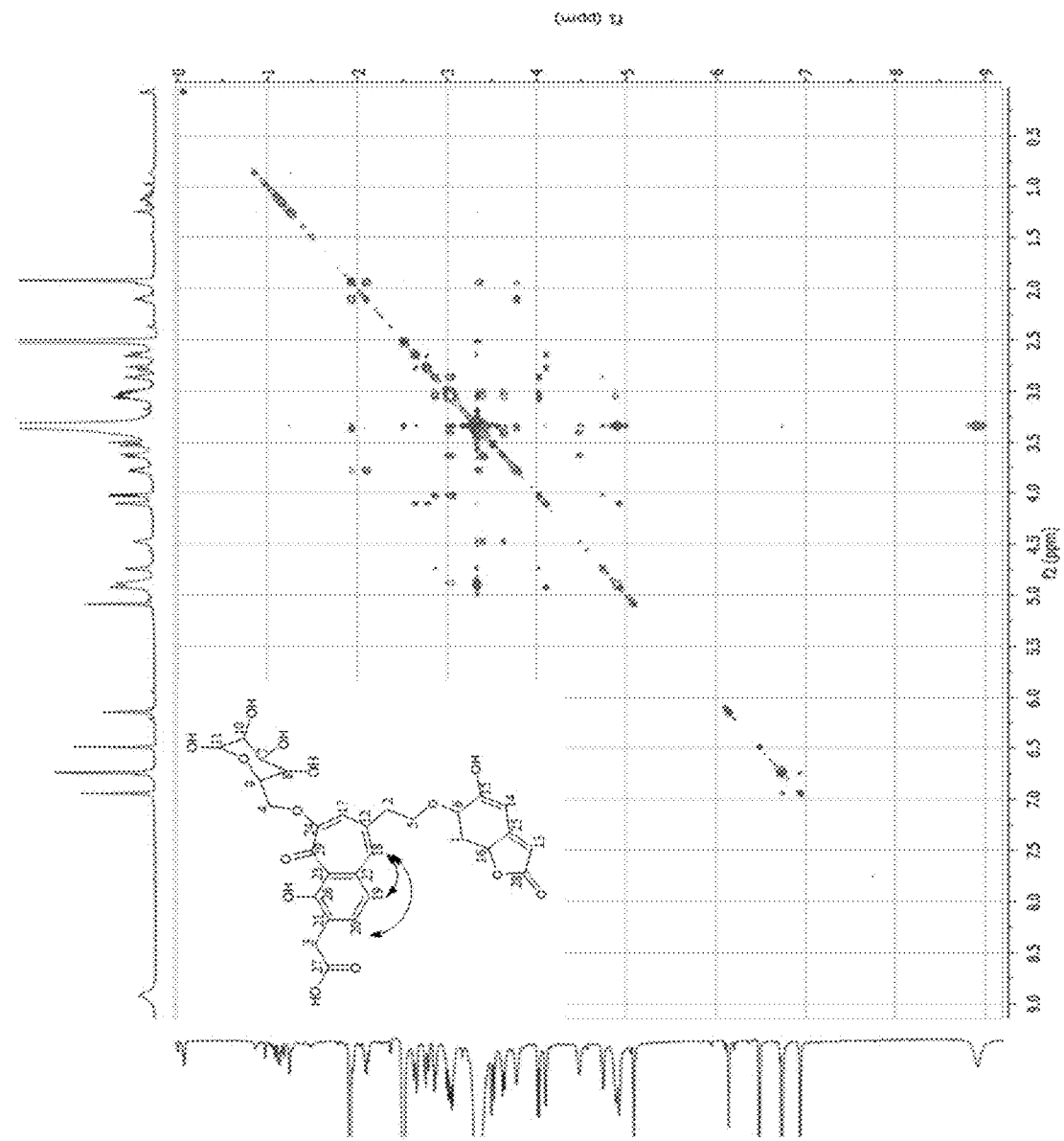
FIG. 28 depicts the TOCSY analysis of F12 in $(CD_3)_2SO$.

HMBC spectrum correlations, indicated by arrows, are shown in FIG. 26. A correlation between carbon 29 and 4 may indicate the presence of the glucose moiety on the tropolone ring, while a correlation between carbon 26 and 3 may indicate the presence of another, isolated $CH_2$ on the aromatic ring.

COSY correlations (FIG. 27) were crucial in determining the presence of two adjacent $CH_2$ groups on carbons 2 and 5. It also indicated the presence of a separate, non-aromatic ring spin-system around carbons 6, 1, and 16. The lack of a COSY correlation to carbon 3 indicated its isolation from adjacent protons, while a single COSY correlation between carbon 4 and 9 indicating that it was the $CH_2$ of the glucose moiety. TOCSY correlations indicated connections between protons of the glucose moiety. A correlation between carbon 18, 19, and 20 indicated their close proximity on the benzotropolone moiety.

F12 as a Food Colorant and Synthesis of F12

In the stability study, CASE proved to be a relatively stable colorant even over a variety of light and temperature conditions. As it is water soluble, CASE lends itself particularly to beverage and candy uses, but would also do well as a component of a flavor or sauce mix. For baking purposes, CASE provides a rich, heat stable color which is a common concern when working with natural colorants. However, special care must be taken when considering the final texture and mouthfeel of CASE colored food products, as high concentrations may lead to a denser crumb texture, or an antioxidant related decrease in maillard browning (Dabas et al., 2011. J. Food Sci 76:C1335-41; Dabas, 2012, Ph.D. Thesis, The Pennsylvania State University). For other food products such as frostings and fillings, it may be possible to combine CASE with alumina or some other material to create a lake. The use of semi-pure CASE in food products is possible; however it is necessary to add a concentration 10-100 times more CASE than the corresponding amount of artificial colorant needed to produce a similar color. This is due to the low concentration of colored compounds within the extract. F12 is believed to be particularly potent, as it produces a vibrant color in the seed extract despite its presence in the low PPB range. It will be important to assure the safety of CASE consumption before production of foods with added CASE, especially those with relatively large amounts of semi-pure CASE.

Synthetic production of F12 is likely to become a more efficient method of acquiring the compound than the extensive time and materials needed to purify the compound directly from seeds. F12 will be able to produce a wide range of colors from pale yellow, to orange, to red, to a deep red-brown color. This wide range of colors is achievable by placing the compound under alkali conditions before readjusting to the desired pH. This means that even in low pH foods CASE can provide a range of yellow and orange colors, which is ideal for its use in beverages juices and sodas, as well as the many unique fall or Halloween treats such as orange colored milk.

Preparation of Comparison of colored and uncolored seed extracts showed a number of known compounds as well as some of undetermined structure. Some of these compounds may act as precursors for F12, however, due to the low amount needed for complete formation of F12, it is unlikely that a change in the overall concentration of those precursors would be observed. Preparation of an uncolored extract proved to be particularly difficult, as even immediate addition of the seeds to a tropolone solution led to a slightly yellow extract. Once a seed is cut or damaged in anyway, it immediately begins forming the orange compounds. For that reason completely colorless extract was unable to be produced.

Purification of F12 from avocado seeds proved to be a very time and resource intensive process with many steps. The inhibition of color formation caused by the addition of tropolone implied the likelihood of a benzotropolone moiety in the colored compound. High resolution mass spectrometry, as well as NMR analysis, confirmed the presence of a glucose moiety which is believed to be the cause of the compound's low solubility in organic solvents. ATR confirmed the presence of C=O bonds, and specifically the presence of a carboxylic acid. The presence of an aromatic ring-CH2-carboxylic acid system was confirmed through a combination of NMR experiments.

Figure 29:
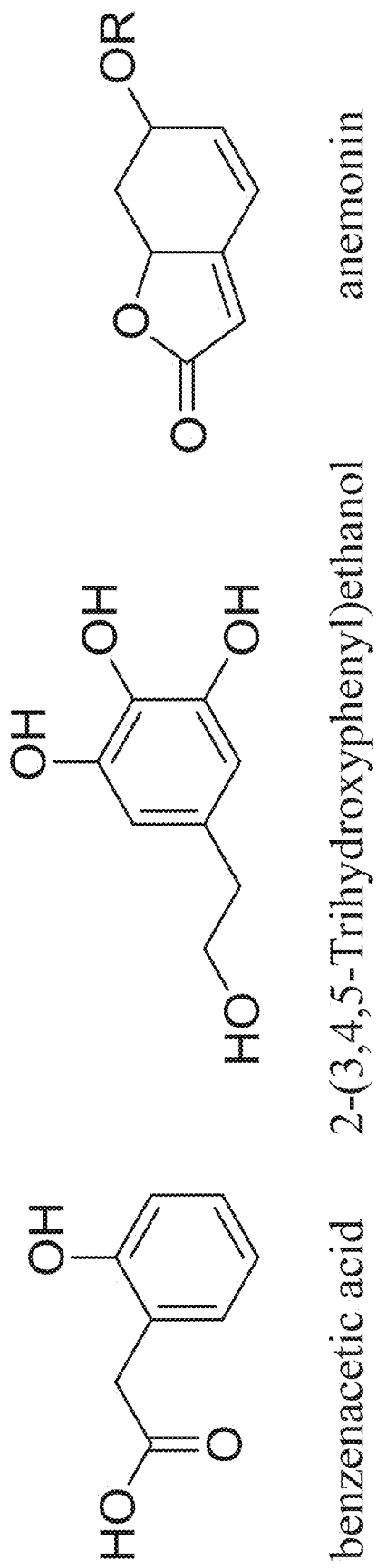
FIG. 29 depicts results of experimental examples demonstrating potential precursors for enzymatic synthesis of F12.
Figure 30:
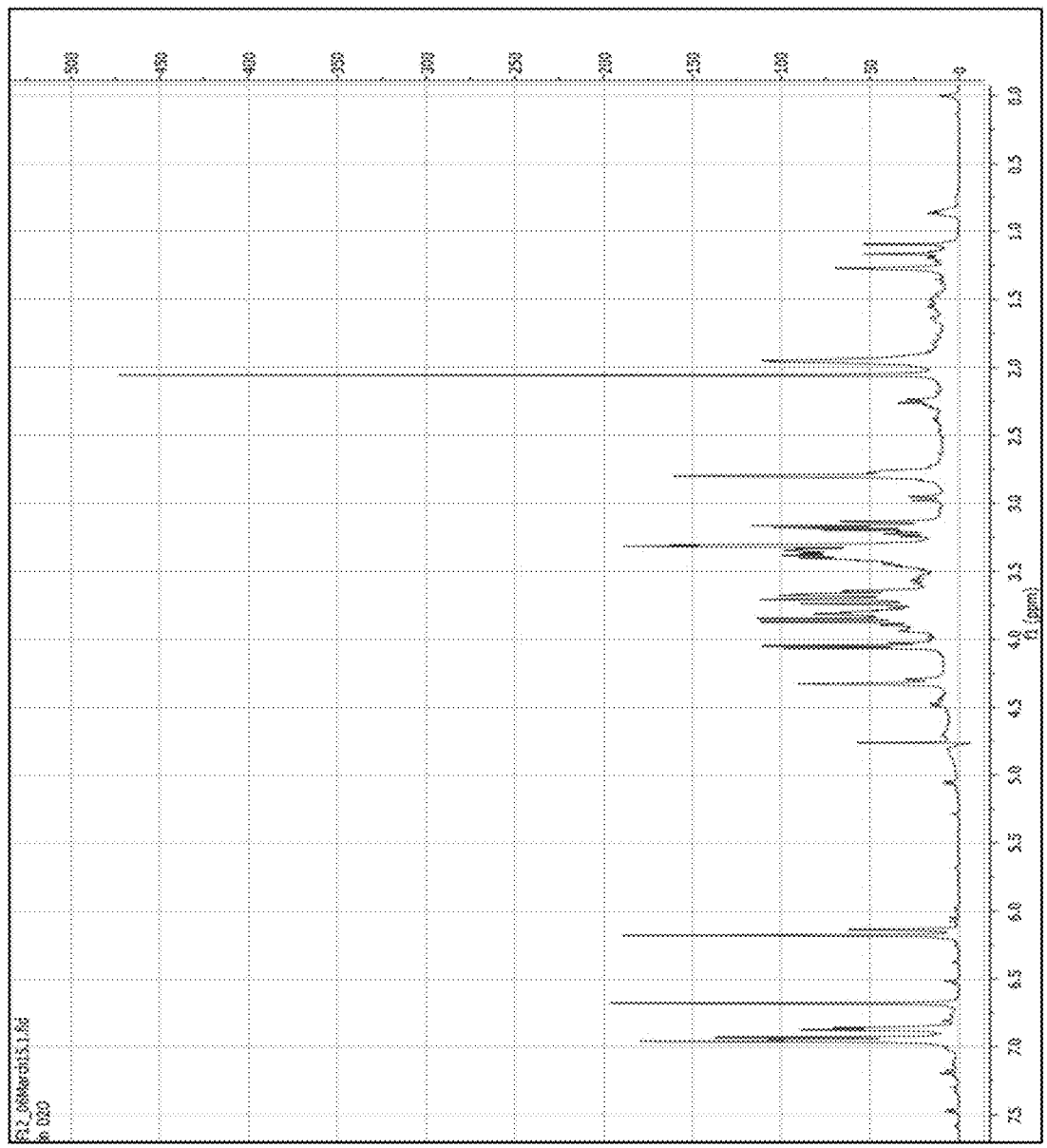
FIG. 30 depicts the $^1H$ NMR spectrum of F12 in $D_2O$.
Figure 31:
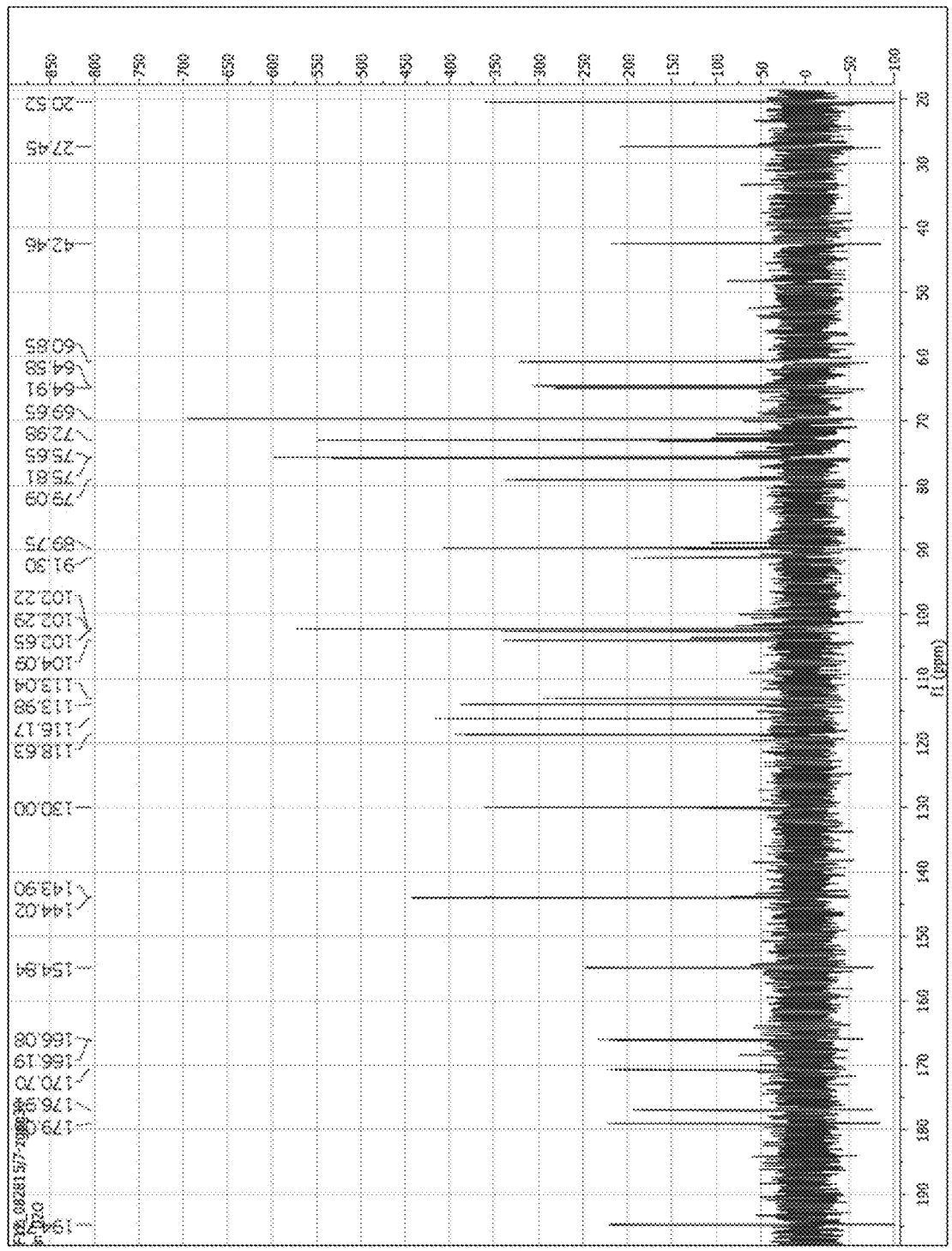
FIG. 31 depicts the $^{13}C$ NMR spectrum of F12 in $D_2O$.
Figure 32:
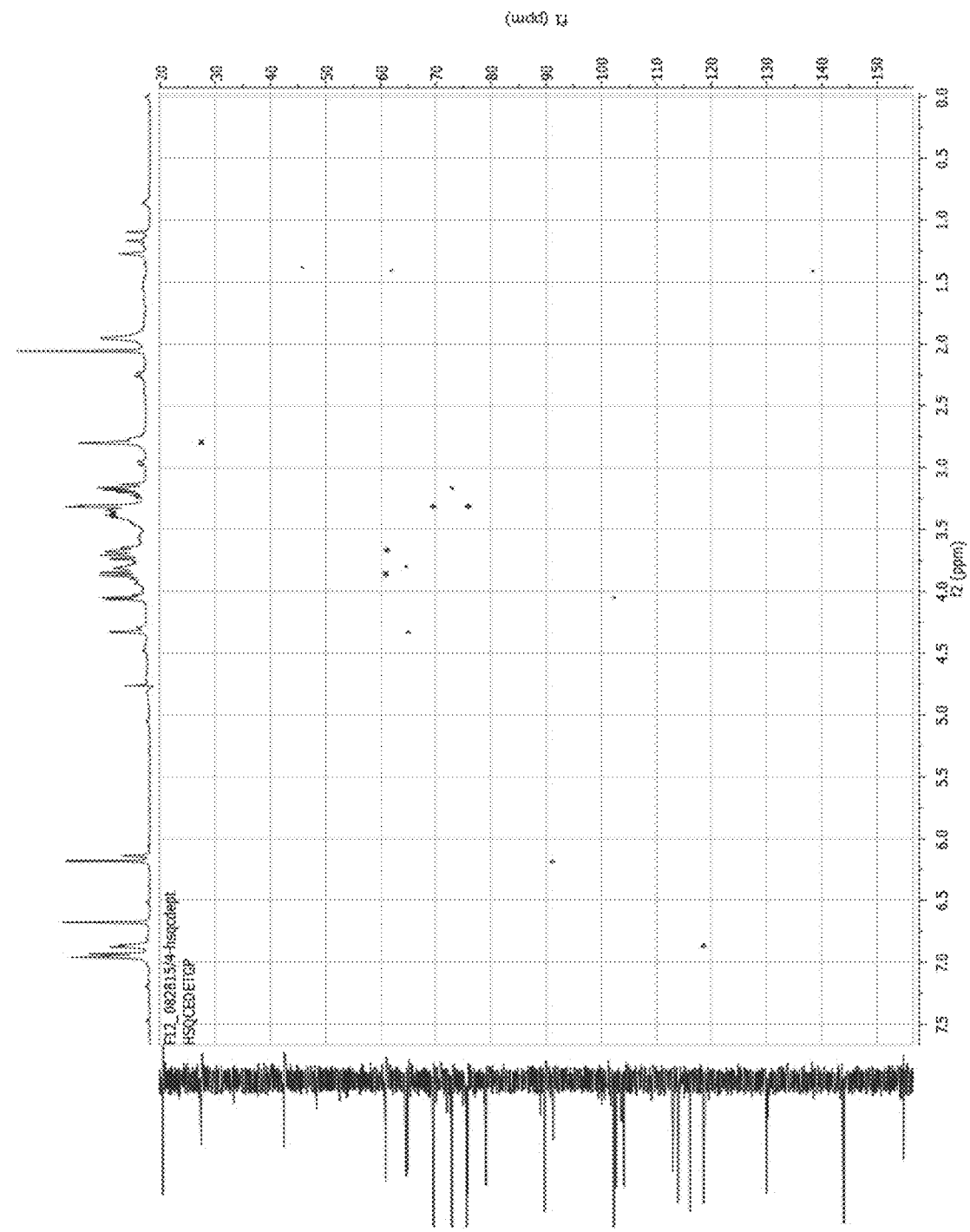
FIG. 32 depicts the DEPT-edited HSQC spectrum of F12 in $D_2O$.
Figure 33:
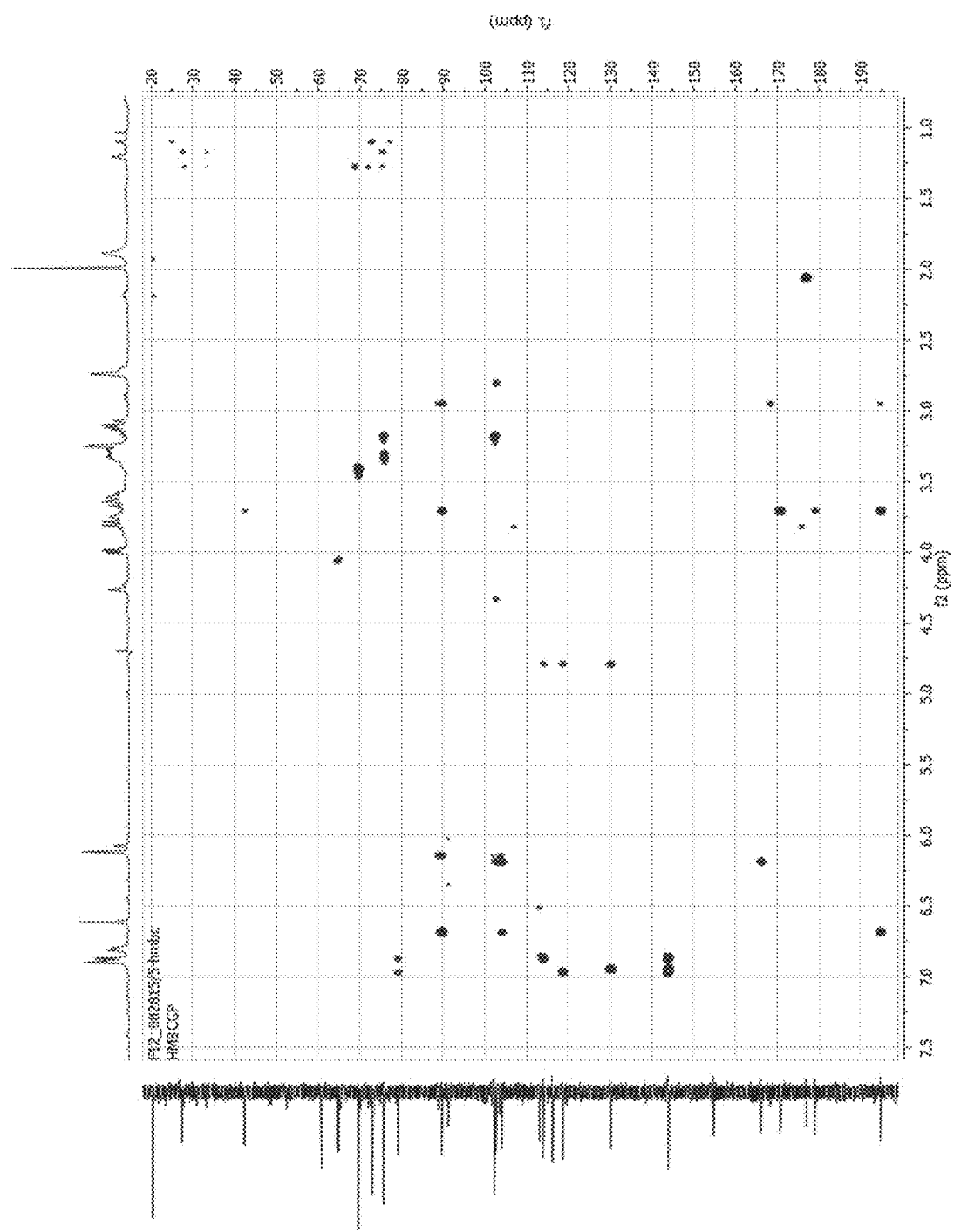
FIG. 33 depicts the HMBC spectrum of F12 in $D_2O$.
Figure 34:
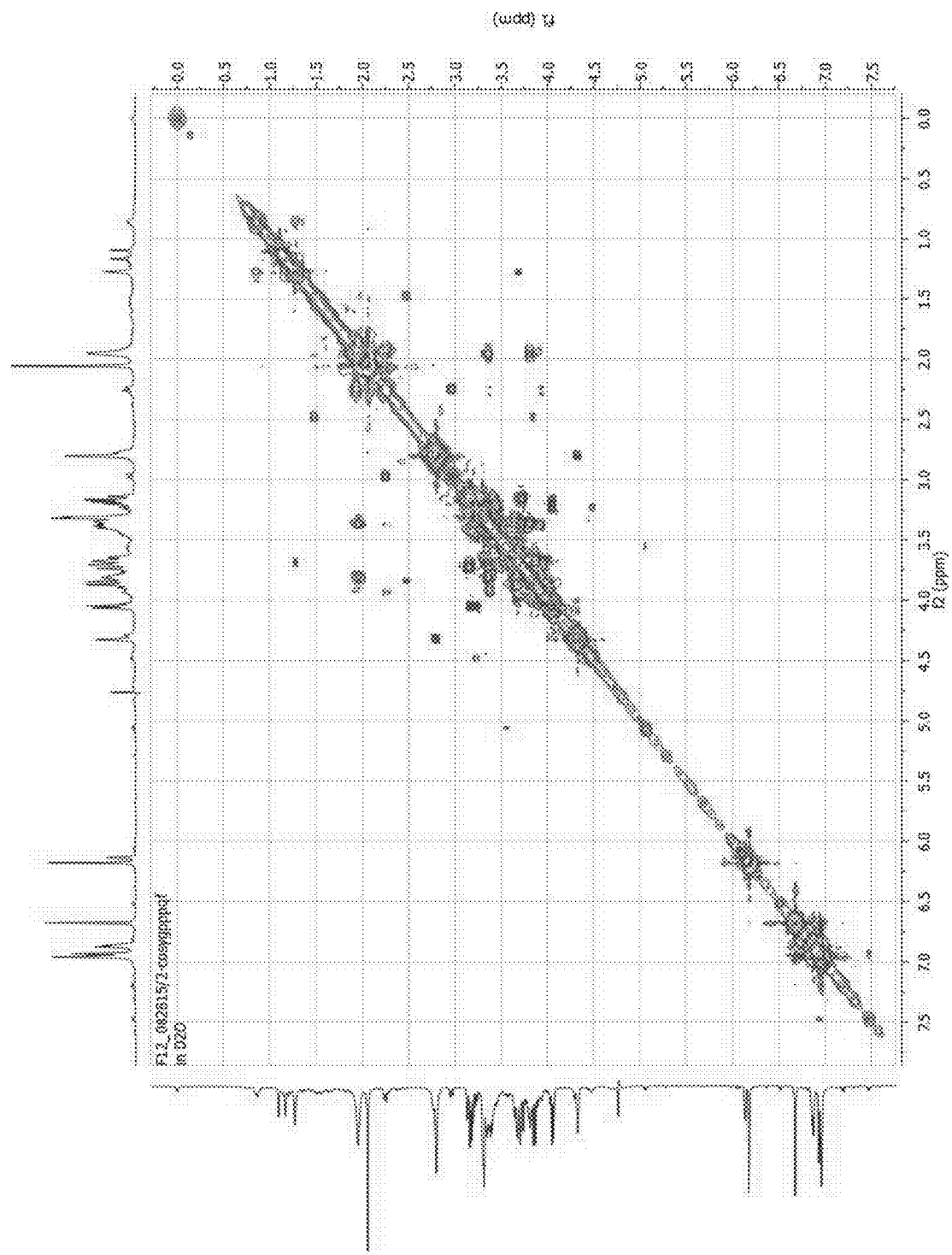
FIG. 34 depicts the COSY analysis of F12 in $D_2O$.
Figure 35:
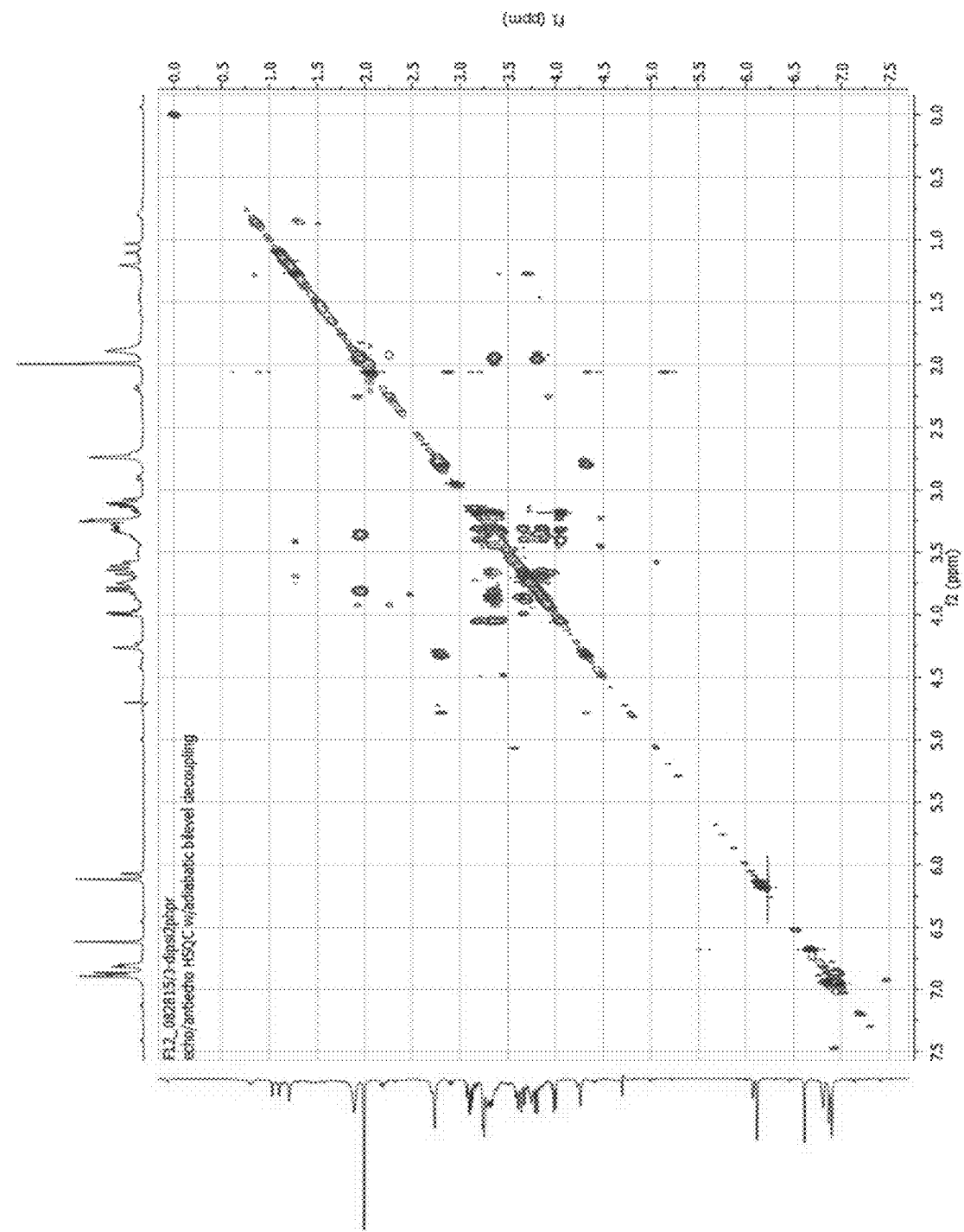
FIG. 35 depicts the TOCSY analysis of F12 in $D_2O$.
Figure 36:
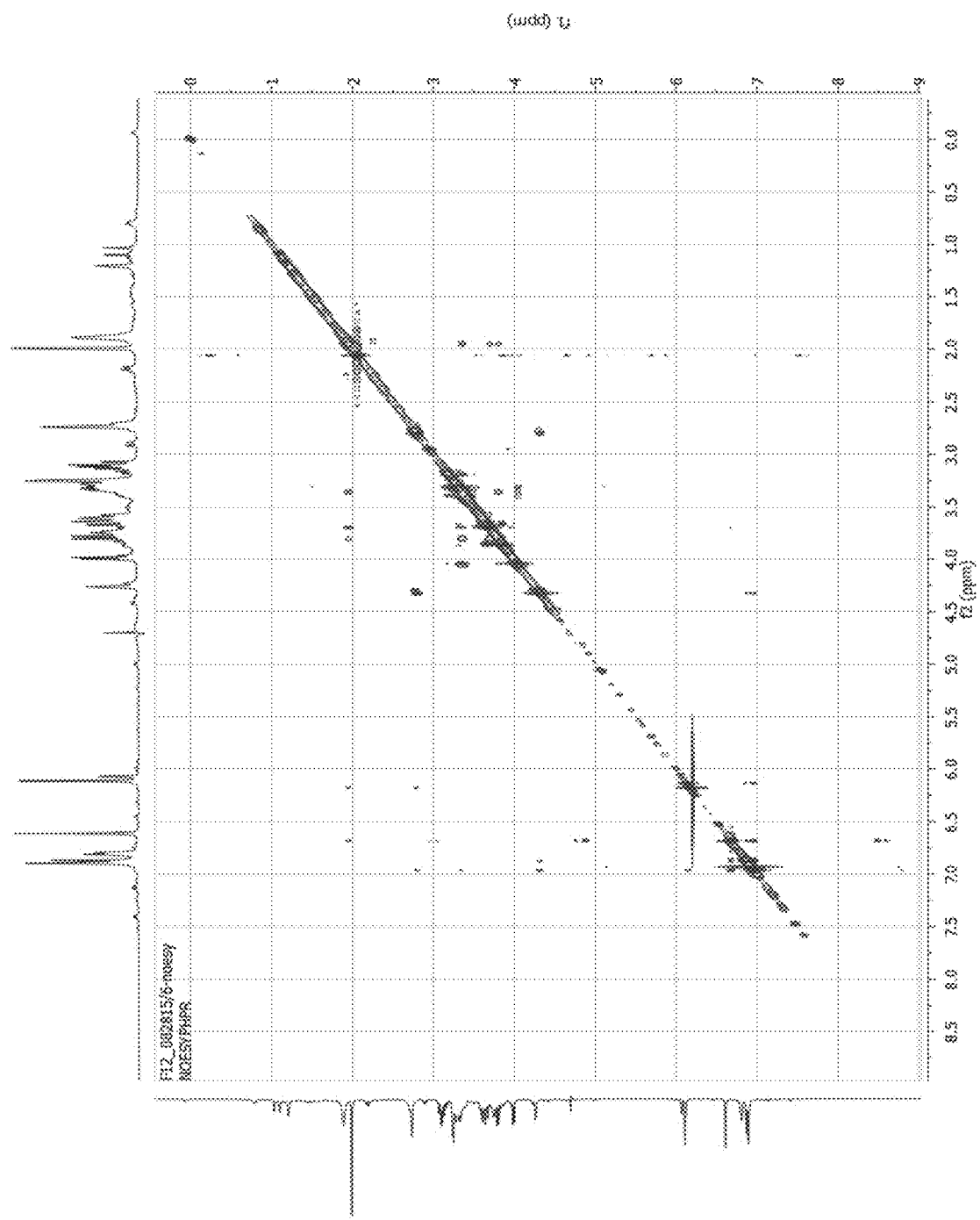
FIG. 36 depicts the NOESY analysis of F12 in $D_2O$.

F12 was indeed found to be a novel glycosylated benzotropolone compound. COSY and TOCSY experiments confirmed the presence of another spin system, removed from the benzotropolone moiety which was found to be a ring-fused butenolide moiety (FIG. 29), similar to that found in buttercups, or the crow's foot family (Ranunculaceae) (Guerriero and Pietra, 1984, Phytochemistry 23:2394-6). An initial synthesis attempt could make use tyrosinase from mushrooms or horseradish peroxidase to provide the enzymatic formation of the 7-membered ring. Compounds such as benzenacetic acid and 2-(3,4,5-Trihydroxyphenyl)ethanol (FIG. 29) could combine via enzymatic synthesis to form the benzotropolone moiety including the $CH_2$—COOH on the aromatic ring, as well as —OH groups which could easily be involved in the addition of multiple side chains including a glucose moiety and a fused-ring butenolide moiety.

Esters can hydrolyze via a variety of mechanisms, particularly in the case of lactones. In the presence of a strong base lactones can hydrolyze to form their parent compound, a bifunctional straight chain compound (Gómez-Bombarelli et al., 2013, J Org Chem 78:6880-9). The color dependence of F12 on pH may be due to the deprotonation of various OH and $CH_2$ groups, and the opening of the butenolide rings at high pH. Ring opening and the deprotonation of OH and $CH_2$ groups could lead to an increase in the number of double bonds in the compound, causing an increase in conjugation which is observed as a red-shift in the color spectrum.

Effect of Semi-Pure CASE on Viability of Human Cancer Cells

Figure 37:
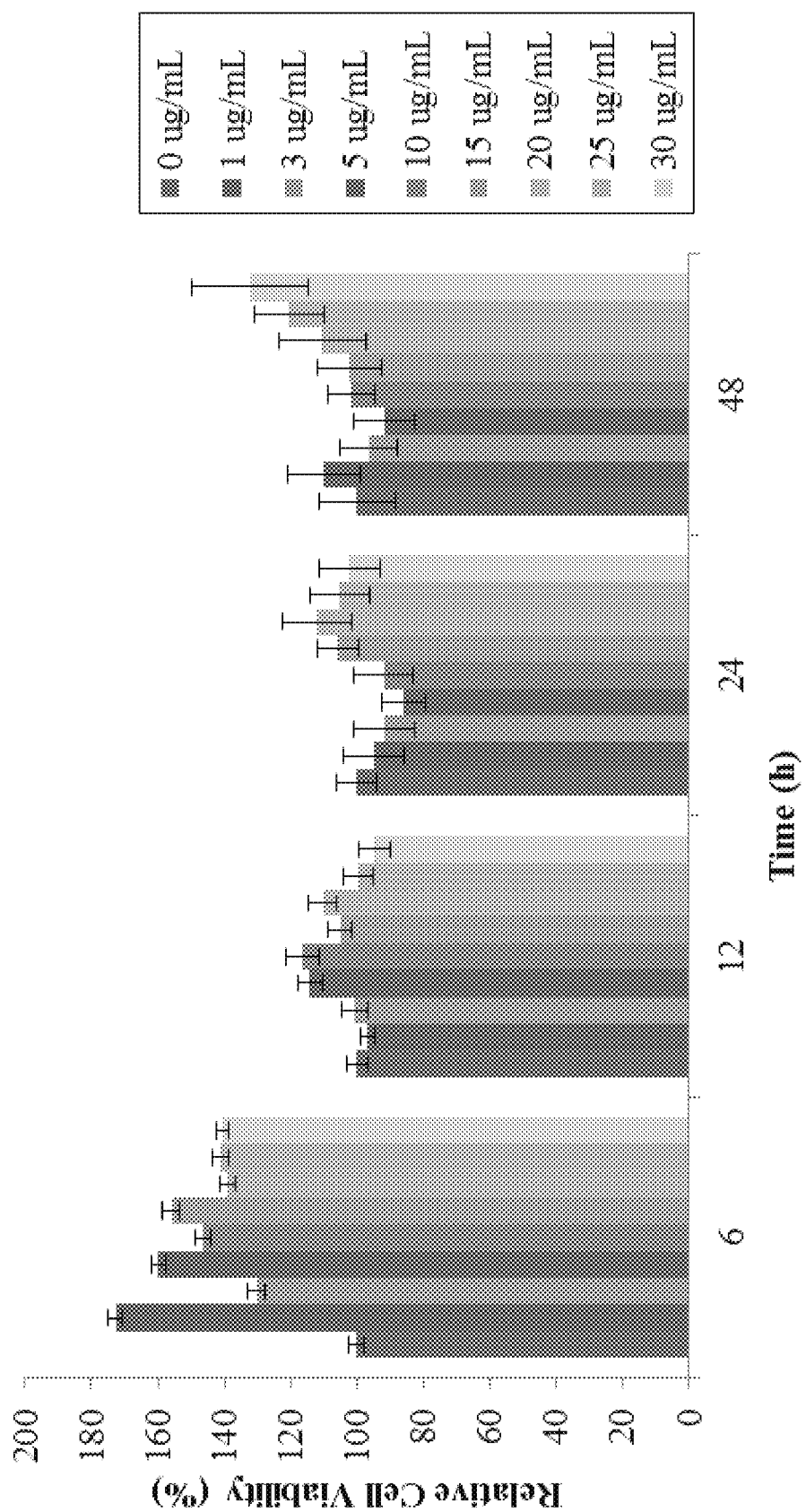
FIG. 37 depicts results of experimental examples demonstrating the effect of semi-pure CASE on viability of LNCaP cells.

Previous studies have shown the anti-cancer effects of some colored avocado seed extracts in LNCaP human prostate cancer cell lines (Dabas et al., 2011. J. Food Sci 76:C1335-41; Dabas, 2012, Ph.D. Thesis, The Pennsylvania State University). Following the same protocol, the effect of semi-pure CASE on cell viability was determined using the MTT assay. The Concentrations of semi-pure CASE used were 0, 1, 3, 5, 10, 15, 20, 25, and 30 µg/mL. In brief, cells were seeded (104 cells/well) in 96 well plates and allowed to attach overnight. The cells were treated with CASE for 6, 12, 24, and 48 h. After CASE treatment, cells were combined with MTT and absorbance read at 540 nm. FIG. 37 shows the results of this experiment. In this study, semi-pure case did not show any decrease in the viability of LN-CaP cells over 48 hours. In some cases, a non-significant trend of increasing cell viability with increasing semi-pure CASE was observed, which could be due to the high polyphenolic content of the extract.

Compounds Isolated from Colored Avocado Seed Extract as Natural Colorant

A colored avocado seed extract is shown herein to be relatively heat, light, and shelf stable and was able to produce a variety of yellow, orange, and red colors. This extract may confer some positive health benefits due to the antioxidant activity associated with its high polyphenol content. While a semi-pure extract may be useful in some applications, the high concentration needed may prove to be a hindrance for its use in foods. In the future, a synthetic route for the production of F12 will make it possible to expand its uses as a natural colorant. Before that time some other studies will need to be conducted as well, in order to determine the safety of consumption of the semi-pure extract and F12, and to help determine an ADI for consumers.

The whole extract presents as a dark or reddish orange color, while F12 is a yellow orange. Further analysis of the whole extract could potentially determine the source of the redder color, which is of particular interest to the natural color market. In previous work, CASE was shown to have some beneficial anti-cancer, anti-inflammatory, and anti-oxidant properties when tested in vitro in human cancer cell lines (Dabas et al., 2011. J. Food Sci 76:C1335-41; Dabas, 2012, Ph.D. Thesis, The Pennsylvania State University). Those effects were not able to be replicated using the semi-pure CASE. This indicates that the colored compounds are likely not solely responsible for the health beneficial effects observed in cell line studies. It is more likely that other polyphenol compounds in the extract are responsible for the effects observed in cell line studies. Further analysis of whole extracts and extracts at various levels of purification, such as the principal component analysis that was conducted on the colored and uncolored extracts in this project, may be useful for aiding in the determination of which compounds are responsible for those effects.

Example 2: Modifications and Derivatives of F12

A polyphenol oxidase (PPO) catalyzed reaction produced the primary pigment in this extract, F12, which is a novel glycosylated benzotropolone compound with carboxylic acid and fused-ring butenolide containing side chains. Though the color is stable at room temperature, liquid chromatography-mass spectrometry (LC-MS) indicates that the individual compounds may not be stable, forming dimers and other compounds in aqueous solution. The most abundant colored fraction showed F12 to have an ion $[M+H]^+$ with m/z 603.1675 in positive mode. Based on the presence of an abundant m/z 441 fragment (Am/z 162), it is hypothesized that this compound is a glycosylated benzotropolone compound. However, the same extract also contained other $[M+H]^+$ ions including a m/z 603.1687 compound, a m/z 917.2639 compound with a m/z 603 moiety, and finally an m/z 1205 dimer produced from the combination of two m/z 603 compounds.

Figure 38:
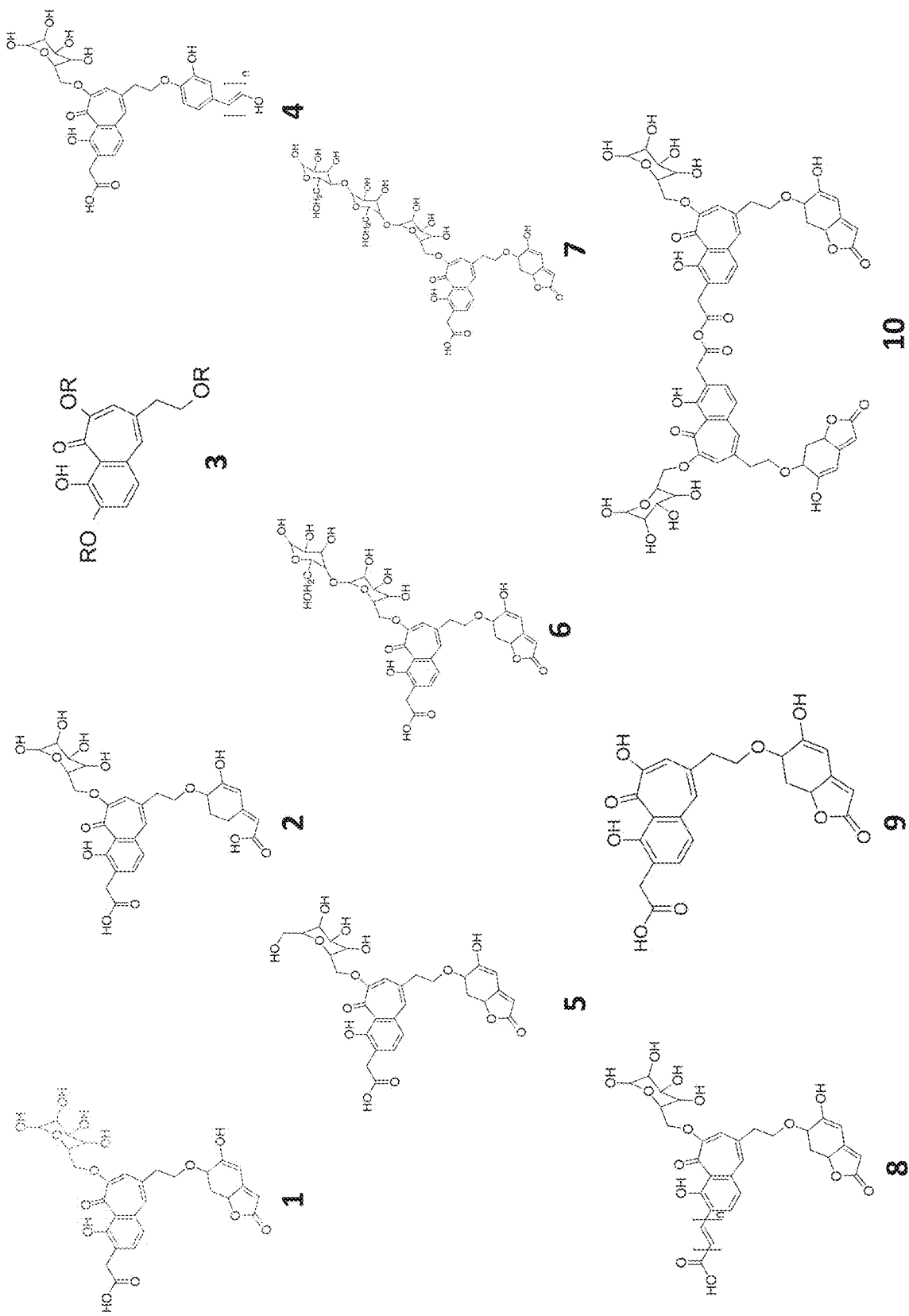
FIG. 38 depicts the chemical structures of F12 derivatives 1-10.

F12 (1), isolated from avocado seeds, is a glycosylated benzotropolone compound with a fused-ring butenolide moiety. When treated with base, the lactone ring of the fused-ring butenolide may open to form 2. Many variations of 1 may be formed in the avocado seed through substitution of the R groups (3) with different compounds present in the seed. Each of which may be useful as a food colorant (FIG. 38).

The fused-ring butenolide may be replaced with some aromatic alcohol with an unsaturated side chain of any length (4). The glucose moiety may be changed to a perseitol/D-mannoheptulose moiety, or other mono, di, or trisaccharide (5-7). Additionally, the carboxylic acid group could be changed even by extending an alkene chain before the carboxylic acid (8). An aglycone compound (9) is possible and may have improved solubility in lipid systems. F12 may also be able to dimerize with itself (10) or other compounds.

Example 3: Perseoranjin and Derivatives of Perseoranjin as a Colorant

The experimental results described herein optimize extraction protocol and structural analyses, and studies the steps of the formation of the color.

The materials and methods employed in these experiments are now described.

Preparation of Extracts

Figure 39:
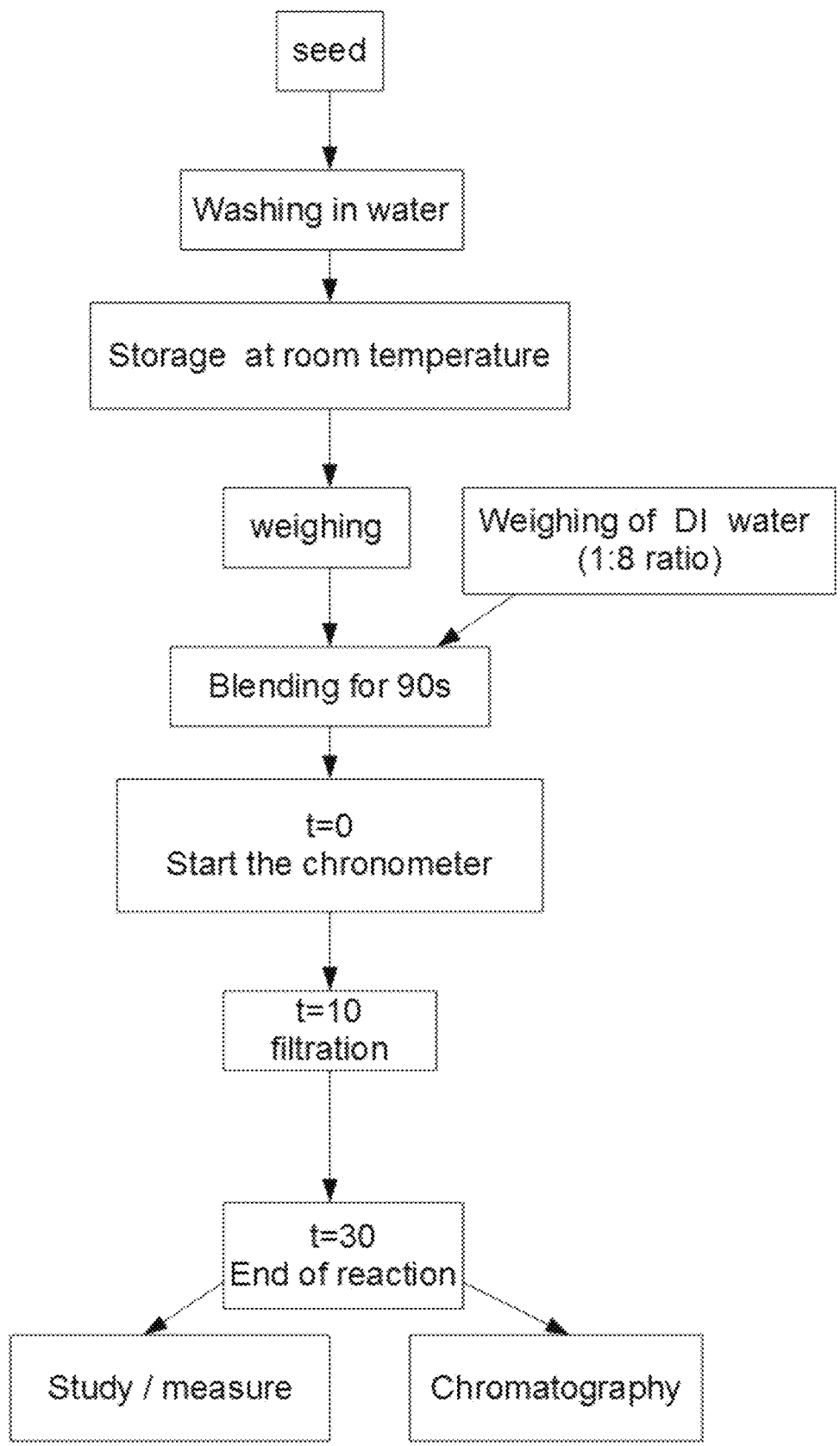
FIG. 39 depicts a diagram of the experimental protocol.

Seeds were weighed and cut with a knife. A weight of deionized water (DI) equivalent to 8 times the weight of seeds was added to the seeds in a Waring blender and crushed for 90 s at high speed. A timer was then started. The resulted paste was kept in the blender until t=10 min. It was then filtrated on Whatman paper filter grade 4 of 110 mm diameter. The solution collected from filtration was left at room temperature until t=−30 min (FIG. 39).

This resulting solution was then placed on a resin into a chromatography column and then eluted with ethanol. Both solutions (after filtration and after chromatography) were used to carry out several measures.

Solid Yield Determination

After filtration, the solution obtained and the solid on paper filter were weighed separately. An extract of each was placed in oven at 50° C. until they were completely dried. Then they were weighed and the solid yield was calculated (per gram of seed). This experiment was performed on 3 different seeds. The solid yield was calculated after chromatography. The filtrated solution was placed in the chromatography column. The solution eluted with ethanol was then dried and weighed.

Measure of Absorbance

Visible absorbance spectra were recorded after 30 min of reactions (2=400 nm to 600 nm) using an Agilent 8453 spectrophotometer (Agilent Technologies, Santa Clara, Calif., U.S.A.) by placing samples in disposable 1.5 mL cuvettes (Plastibrand, Wertheim, Germany).

Enzymatic Activity Assay

This test evaluated the difference of enzymatic activity depending on the temperature of reaction (24° C., 30° C., 40° C.). The enzymatic activity was assessed with the absorbance after 30 min of reaction. Seeds were blended in 0.1M sodium phosphate buffer.

The weight of buffer was 8 times the weight of seed.

The use of a buffer allows for three different steady pH for each temperature of reaction: 5.8, 6.9, 7.9. These pH are chosen because it seems that the optimum pH for PPO is in the interval [5.5-8] depending on the fruit or vegetable (Nagodawithana T, Reed G 1993).

There are thus 9 combinations pH-temperature. Each of them was repeated three times to reduce the variability due to the seed.

Impact of pH on Color Formation

To evaluate the impact of pH modification on color formation different volumes of NaOH 2N and HCl 1N were added to several samples from the same seed. Hydrochloric acid was added by 0.02 mL reach a pH of about 2. Sodium hydroxide was added by 0.01 mL to reach a pH of about 10. The optical density was then measured at t=30 min.

Determination of Acid $pK_a$

Previous research suggests that there is a carboxylic acid group in the structure of the pigment studied. To evaluate the pKa of this acid in solution a purified extract (after chromatography) was used. Ethanol was removed in oven and the recovered solid was diluted in DI water. The resulting solution was titrated with NaOH 0.25N.

Study of the Precipitate

A precipitate formed after incubation overnight at room temperature. As a difference of precipitate color was observed depending on pH, several extracts were prepared by addition of NaOH 2N or HCl 1N to evaluate more precisely the impact of pH on this agglomerate.

In order to avoid the formation of the precipitate, others extracts were realized. After filtration on Whatman paper grade 4 (retention of particles of 20-25 m), the resulting solution was either centrifuged or boiled or filtrated again on Whatman paper grade 2 (retention of particles of 8 μm). The supernatant of centrifugation was stored at room temperature and the formation of a precipitate was watched. The boiled solution was filtrated again on Whatman paper grade 4, because some mass were formed, and stored at room temperature. These different processes were all realized from the same seed.

The results of the experiments are now described.

Solid Yield Determination

The mean solid yield obtained from the liquid part after filtration was 8.1%. The mean solid yield obtained from the solid part was 42.9% indication that the protocol design allows us to recover 51% of the avocado seed solid. The seed moisture content is about 50% (Olaeta J A et al. 2007), and therefore the extraction protocol did not result in loss of solid.

Measure of Absorbance

Figure 40:
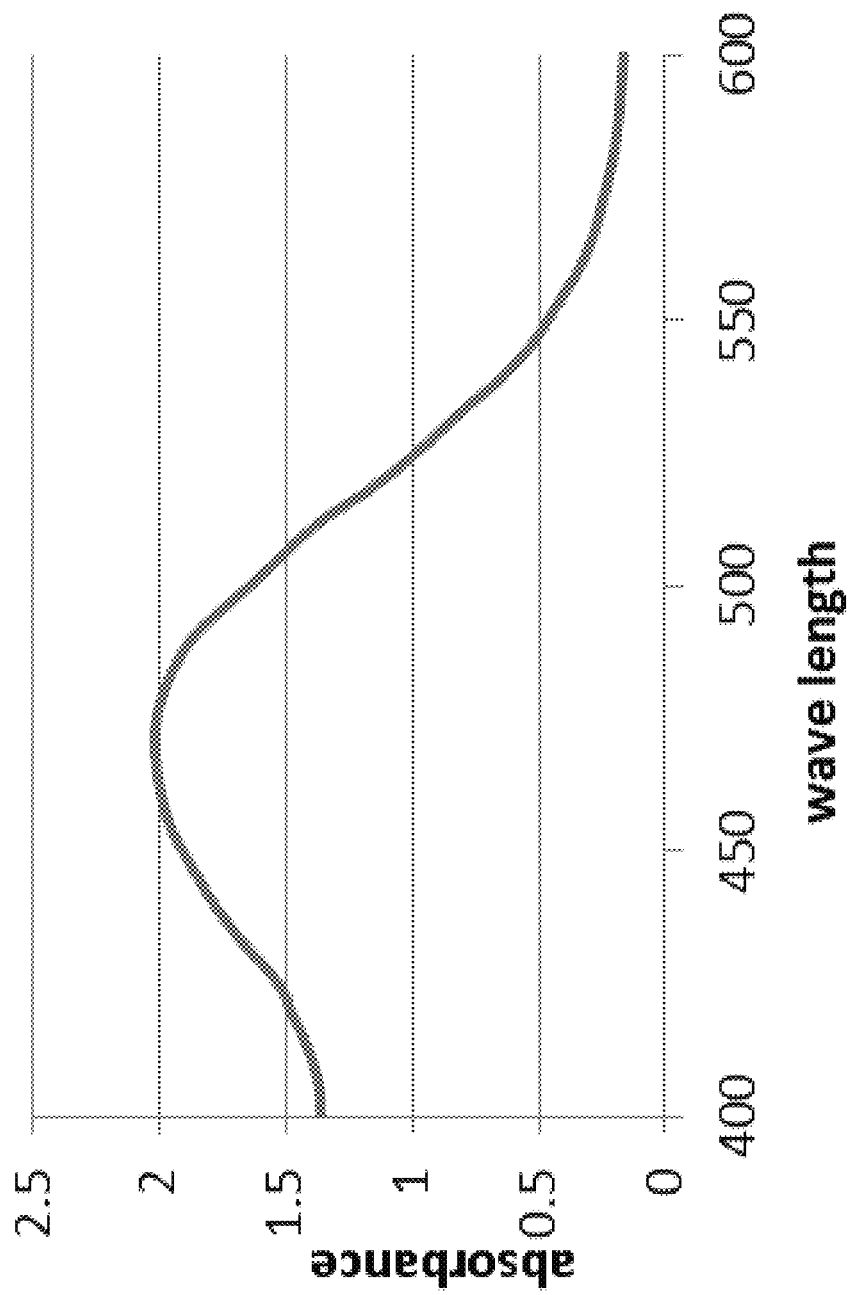
FIG. 40 depicts the absorbance spectrum of a sample.

The absorbance spectrum between 400 nm and 600 nm is generally the same for all seeds. The absorbance peak is about 475 nm (FIG. 40).

Relation Between Seeds Weight and Absorbance

A test was carried out on 30 seeds to assess the presence of a link between seed weight and pigment concentration. The interest of a link between these two parameters is that it might allow to standardize the extraction protocol, and to optimize it according to the weight of the seed.

The test indicates that there is no link between the weight of seeds and the pigment concentration. Statistical analysis was performed to demonstrate this. The amount of pigment may be linked to the degree of maturity of the seed rather than to its size. It would be interesting to determine the evolution of the amount of pigment during development of the seed.

The absence of link between weight of seed and the absorbance may be an advantage because it would allow for the use of a seed regardless of its weight.

Evaluation of the Impact of Temperature on Enzyme Activity

Figure 41:
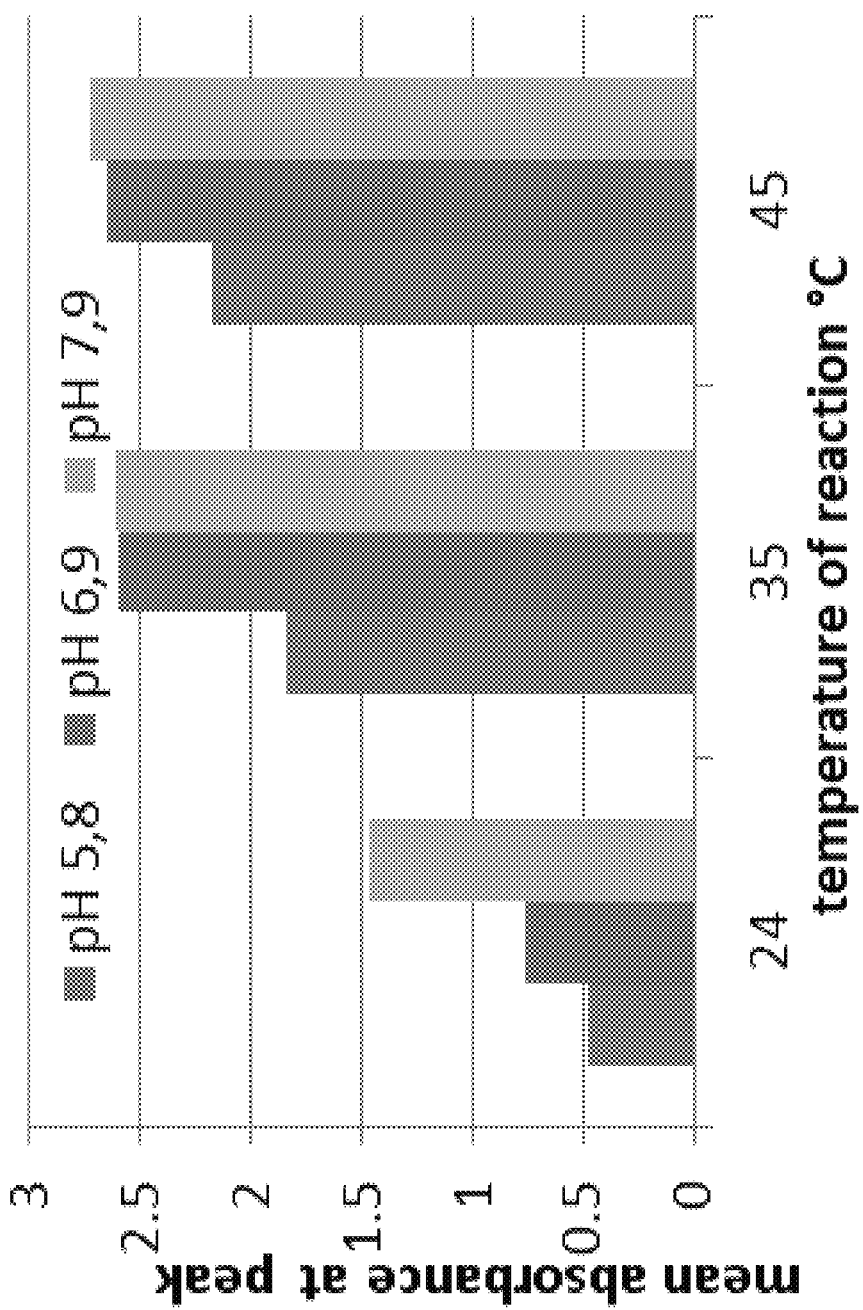
FIG. 41 depicts the evolution of mean absorbance with temperature and pH (3 samples for each measure).

The mean absorbance peak from extract obtained at 35° C. and 45° C. were different from the absorbance peak from extract obtained at 24° C. (room temperature) regardless of the pH of the buffer used (FIG. 41). However, the test was not performed on a sufficient number of seeds to evaluate the significance of the results. If we consider the test as significant, the interest of carrying out the protocol at 45° C. has to be verified. Thus, the stability of absorbance (which reflects color stability) during 3 days will be evaluated either for samples extracted at 24° C. and those extracted at 45° C.

Study of the Absorbance Stability

Figure 42:
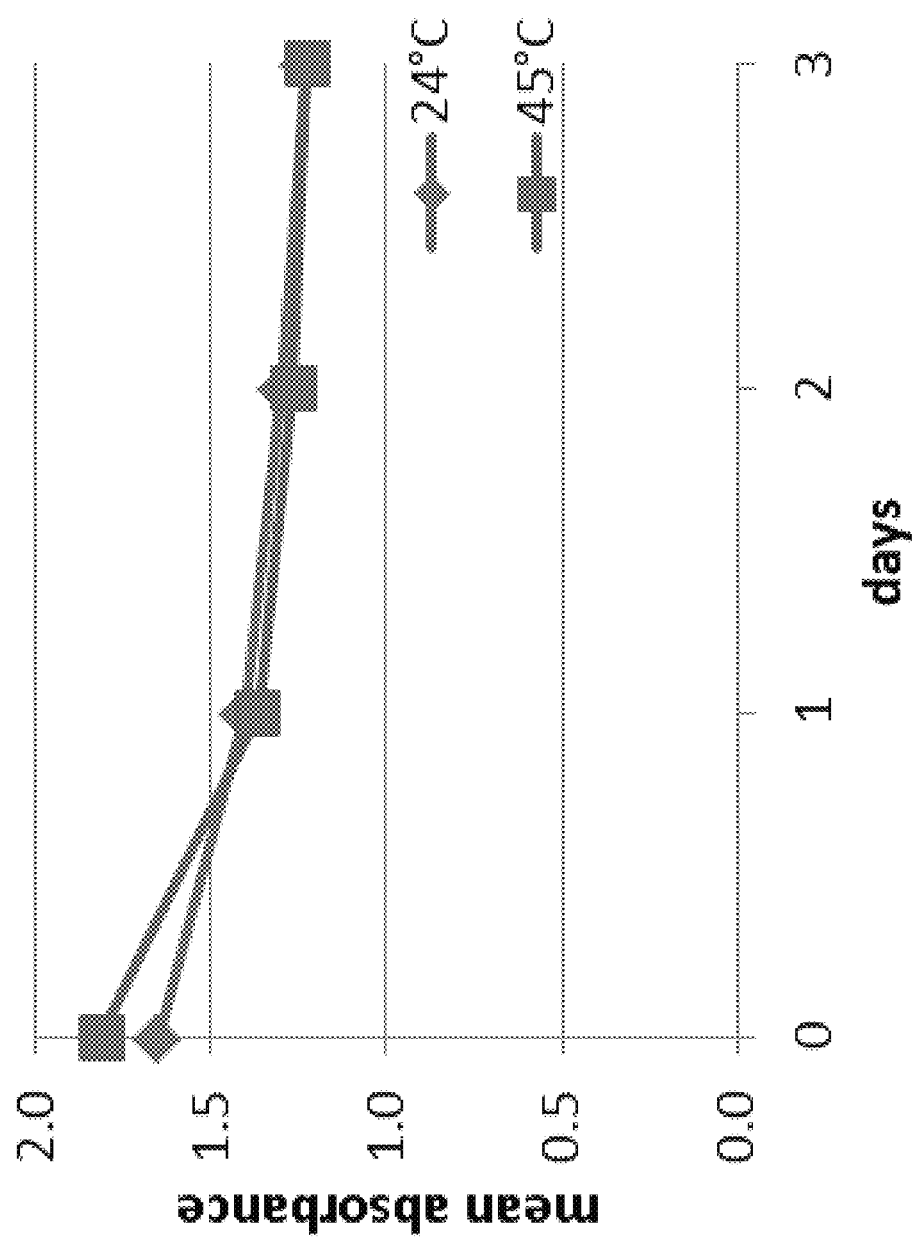
FIG. 42 depicts the stability of the mean absorbance for 3 days depending on the temperature, done on three seeds for each.

The absorbance peak of 13 seeds (a first batch of 7 seeds and a second batch with 3 seeds at 24° C. and 3 at 48° C.) was measured once a day for 3 days, on solutions kept at room temperature. The absorbance peak diminished over the course of a couple of days before stabilizing at the same value regardless of the temperature (FIG. 42). Carrying out the test at 45° C. instead of the room temperature is thus not beneficial. The evolution of color is more interesting to evaluate on the solution obtained after chromatography than as to evaluate most purified extract that we can.

Impact of pH on Color Formation

Figure 43:
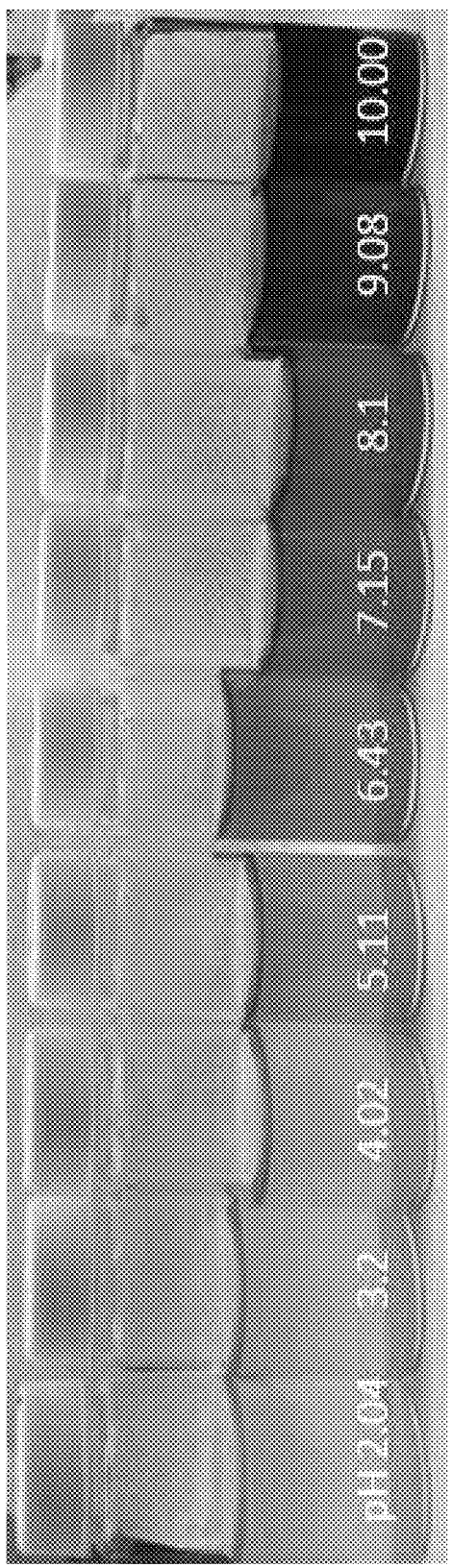
FIG. 43 depicts the difference of color of the same solution depending on the pH.

The color formed during the reaction depends on the pH of the solution. The solution varies from a yellow color at low pH to brown/red color at high pH (FIG. 43).

Figure 44:
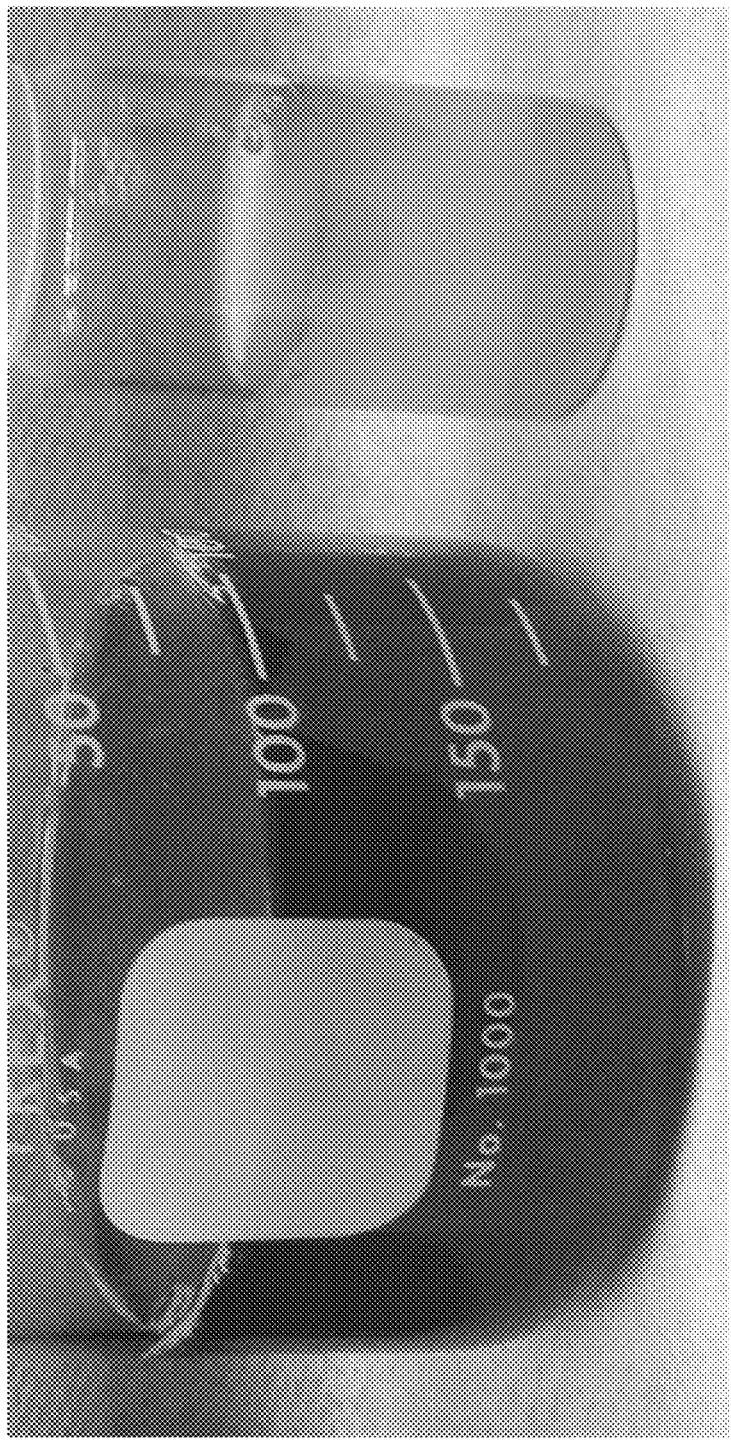
FIG. 44 depicts a solution which was brought from pH2 to pH 11 (left) and a control solution at pH 2 (right).

When the opposite experiment was carried out the color was not recovered. Indeed when a solution at pH 11 was acidified to pH 2, the color was dark orange. (FIG. 44). And when a solution at pH 2 was brought to pH 11, the color was not brown/red. This indicates that the color change with pH was not reversible. This result suggests that the pH of the food is not insignificant and must be taken into consideration if the extract is used as food colors.

Figure 45:
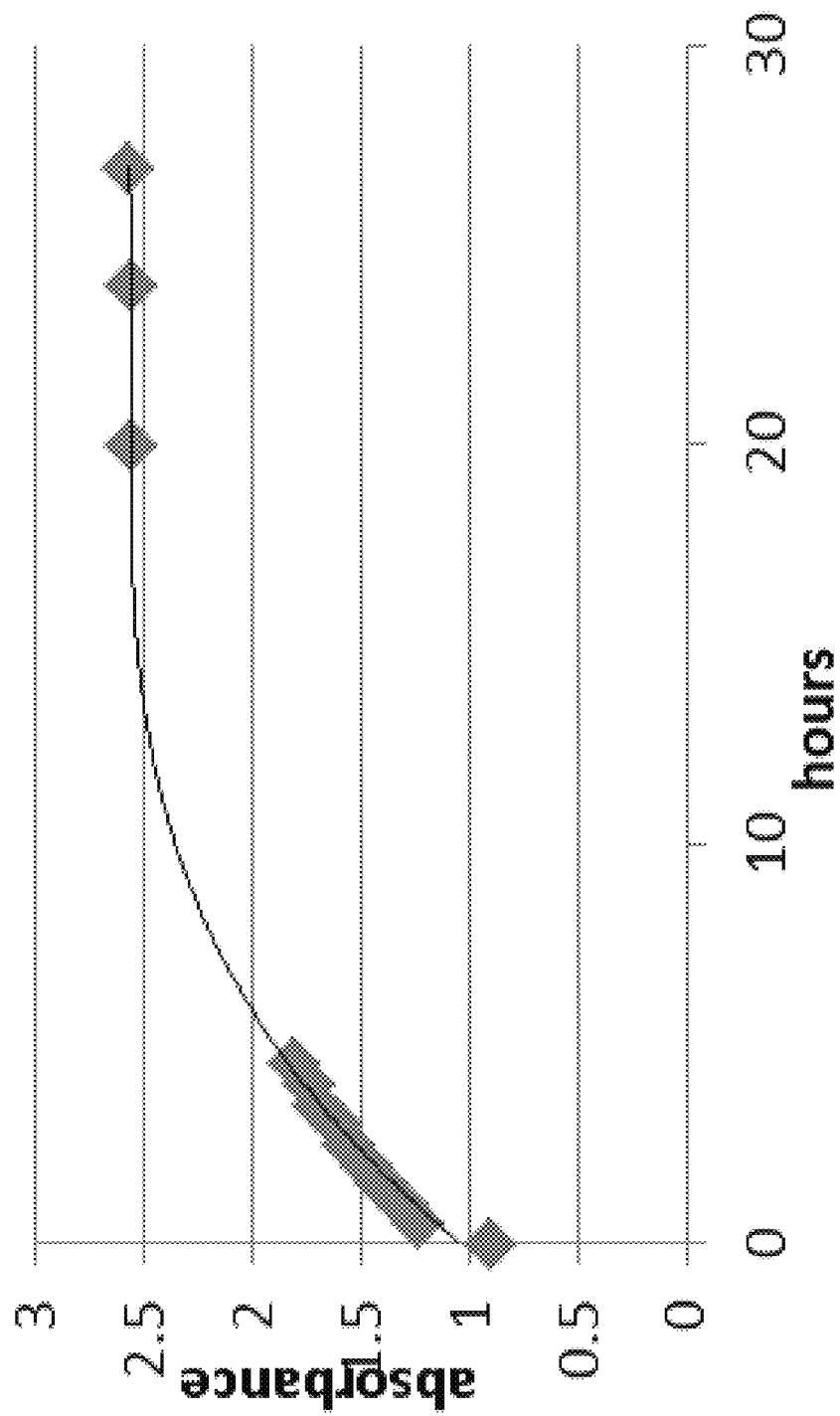
FIG. 45 depicts the evolution of the absorbance at 418 nm for a sample at pH 11.

Another aspect which deserves to be studied was the kinetics of color change at pH 11. When the solution was just prepared, it was still orange but some time later it turned to dark red. A solution was then prepared at pH 11 at its absorbance spectrum was recorded every 30 min. The whole spectrum was interesting but the evolution of the absorbance at the wave length corresponding to a red color of the solution (=418 nm is chosen) was the most important to observe. Indeed, it is worth knowing how much time is needed for the color to stabilize after a change of pH. After about 16 hours, the absorbance at 418 nm remained constant (FIG. 45).

Determination of Acid pKa

Figure 46:
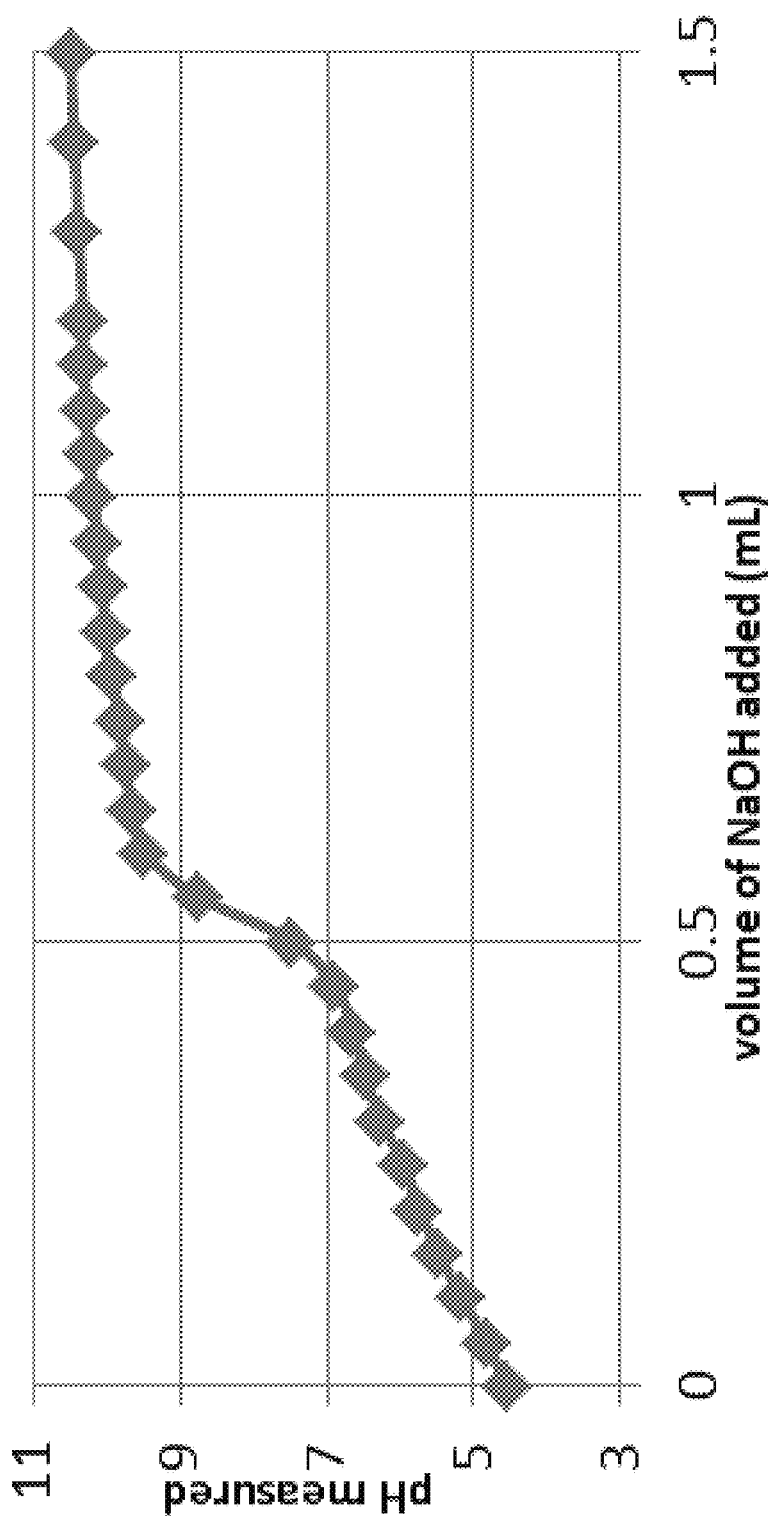
FIG. 46 depicts a titration curve of the solution with sodium hydroxide.

Titration has resulted in an approximation of the pKa of the acid present in the structure of the pigment by the tangent method. The pKa belongs to the interval [5.8-6.2](FIG. 46). Knowing this pKa will help in the determination of the exact structure of the pigment. It will also help to understand the behavior of the pigment according to the environmental conditions.

Study of Storage Condition of Seeds Before Reaction

In a perspective of commercialization, most avocado pits will be sent from California or Mexico. It is difficult to send fresh seeds on which it would remain avocado flesh, which could mold during the journey. This will test if it is possible to mix several non fresh seeds (boiled, frozen . . . in which the enzymes, among them that responsible for the pigment formation, will be denatured) with one fresh seed (the only one to bring enzyme).

Figure 47:
FIG. 47 depicts the difference of color depending on the composition in fresh seeds of the solutions.
Figure 48:
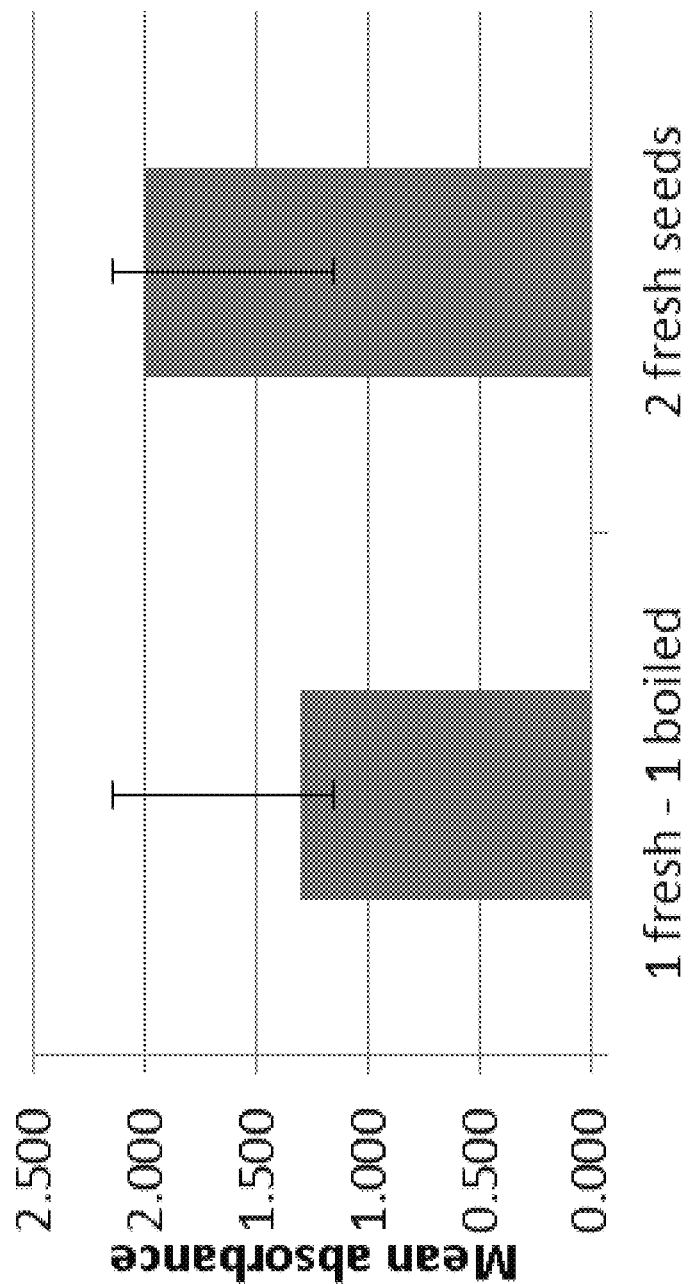
FIG. 48 depicts the difference of mean absorbance at the peak (470 nm) in fresh seeds of the solutions.

The test was carried out by mixing 2 seeds (2 fresh or 2 boiled or 1 boiled with 1 fresh). Then absorbance peaks were compared. Every batch of two seeds was repeated three times. By observing the samples, it appears as if there was a difference in color between the three solutions (FIG. 47). But comparison of the absorbance between two fresh seeds and mixture fresh/boiled showed a non significant difference (FIG. 48).

Although there was no absorbance difference, boiling the seeds appeared to cause gelatinization of starch they contain, which may be problematic. Indeed solutions with two boiled seeds or mixed solutions were very difficult to filter. This step was extremely time-consuming, much more than with only fresh seeds, and it was not very effective. These differences were very significant, which was a real problem in a perspective of industrialization.

Study of the Precipitate

Avocolor™ has also been tested. The main problem they shared is the presence of a precipitate that forms over time when they re-dissolve the powder in an aqueous solution. This precipitate is an agglomerate and is gooey and gelatinous, often light colored which deposits on the sample bottom. The precipitate grows with time. Sometimes after few days, it ascends in the sample to form a mass in the middle of the liquid. When the precipitate was removed from a sample, it was reformed few days after.

Figure 49:
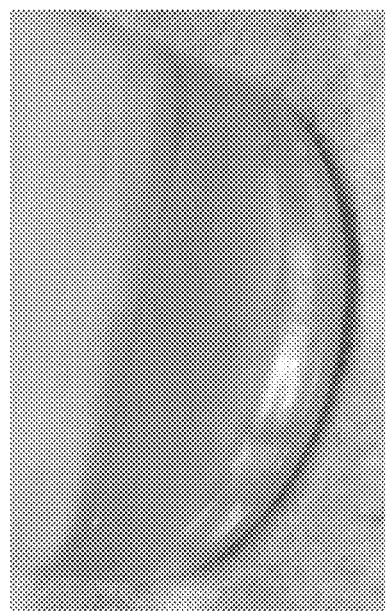
FIG. 49 depicts a cloudy and uncolored precipitate from a solution at pH11 in acidified ethanol.
Figure 50:
FIG. 50 depicts small red balls of precipitate from a solution at pH2 in acidified ethanol.
Figure 51:
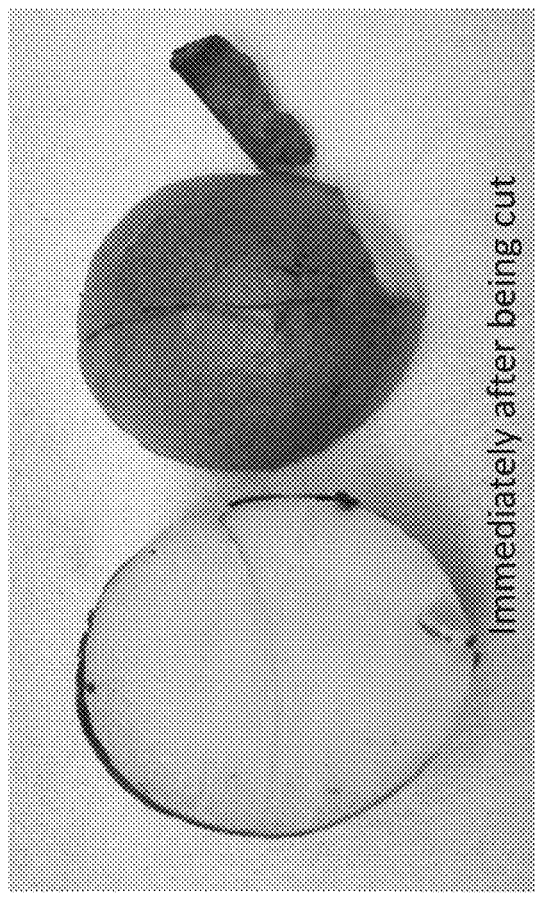
FIG. 51 depicts the raw material, the avocado seed, immediately after being cut and 15 minutes after being cut
Figure 51:
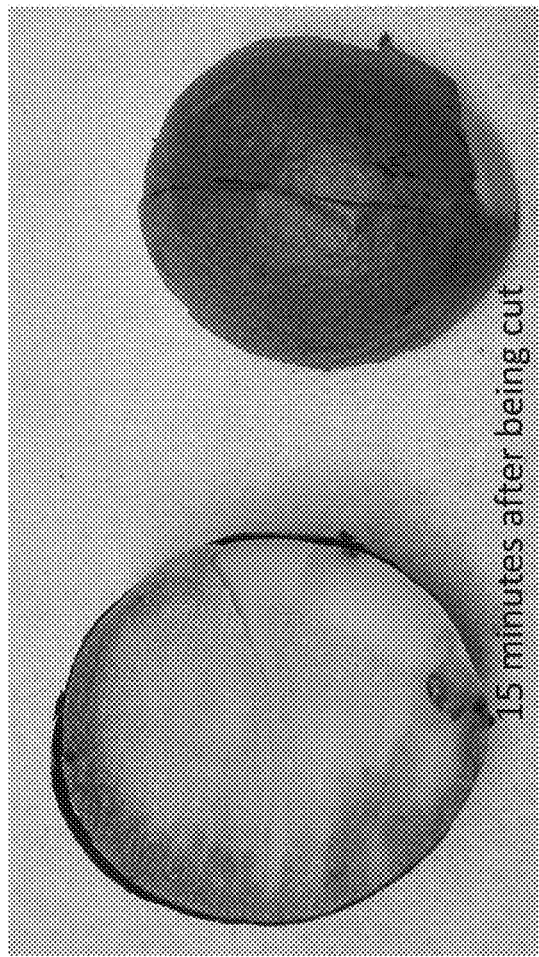
Figure 52:
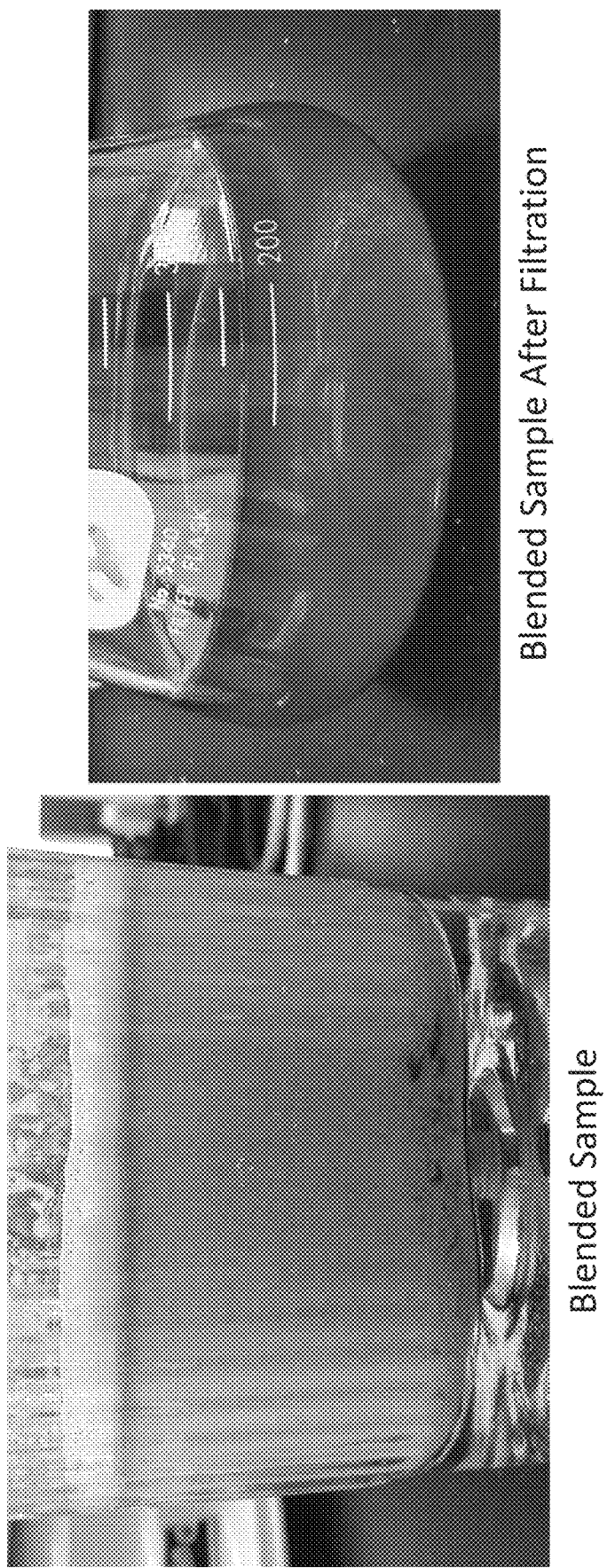
FIG. 52 depicts a blended avocado seed sample before and after filtration.

When the solution obtained after filtration was centrifuged or boiled, a precipitate was formed but after several days (3-4 days vs 1-2 days normally) and it was really small. The second filtration with Whatman paper grade 2 did not seem to impact the precipitate form, color or quantity. Therefore, there may be an effect of pH on the precipitate. The precipitate were recovered from samples and then put in acidified ethanol. At high pH the precipitate was bright orange/red whereas at low pH it was light orange/uncolored (FIGS. 49-50). Moreover, at low pH the precipitate looked like filaments or small balls whereas the precipitate at high pH had a cloudy appearance.

Since the avocado pit contains starch (it is an amylaceous seed), this molecule might be a compound of the precipitate. The avocado seed also contain pectin (Pahua-Ramos et al. 2012). It could explain the different types of precipitate depending on pH. Pectin tends to jellify at low pH (around pH 3) whereas it is unstable at higher pH.

Alternatively, if the solution after filtration contains protein there may be, depending on the conditions, the formation of a complex with the polyphenols. The complex formed with protein and polyphenols is often due to the presence of Van der Waals interaction. This bound is thus reversible. If such a link is formed, it results in a decrease of the electrical charge of the protein and an increase of its molecular mass. Then the complex flocculates. (Moreno, Peinado 2012). This binding is pH-dependent. Indeed pH changes the electrical charge of the protein and of the polyphenols. When the pH increases the electrical charge of polyphenols becomes more negative. Beyond the isoelectric point the protein charge is negative. This could explain that the precipitate does not look like the same depending on pH. At certain pH there is maybe a flocculation of protein-polyphenol complex whereas at other pH the precipitate could be due to another phenomenon. The interest of chromatography would then be to remove the protein and starch, and so to reduce the precipitate formation possibilities.

This work shows many aspects of the avocado seed which have been studied. The solid yield was calculated. The impact of several parameters on the absorbance was evaluated: seed weight, temperature, pH, seed storage conditions. It appears that pH is a key factor to understand the phenomenon that occurs. pH affects both the color intensity, the absorption spectrum of the extracts, but also the precipitate which forms. This precipitate is still the major barrier to the use of the Avocolor™ in food. First safety tests have been performed on mice. There were no signs of diseases. But other studies are needed to know the extent of food applications of this extract.

Figure 53:
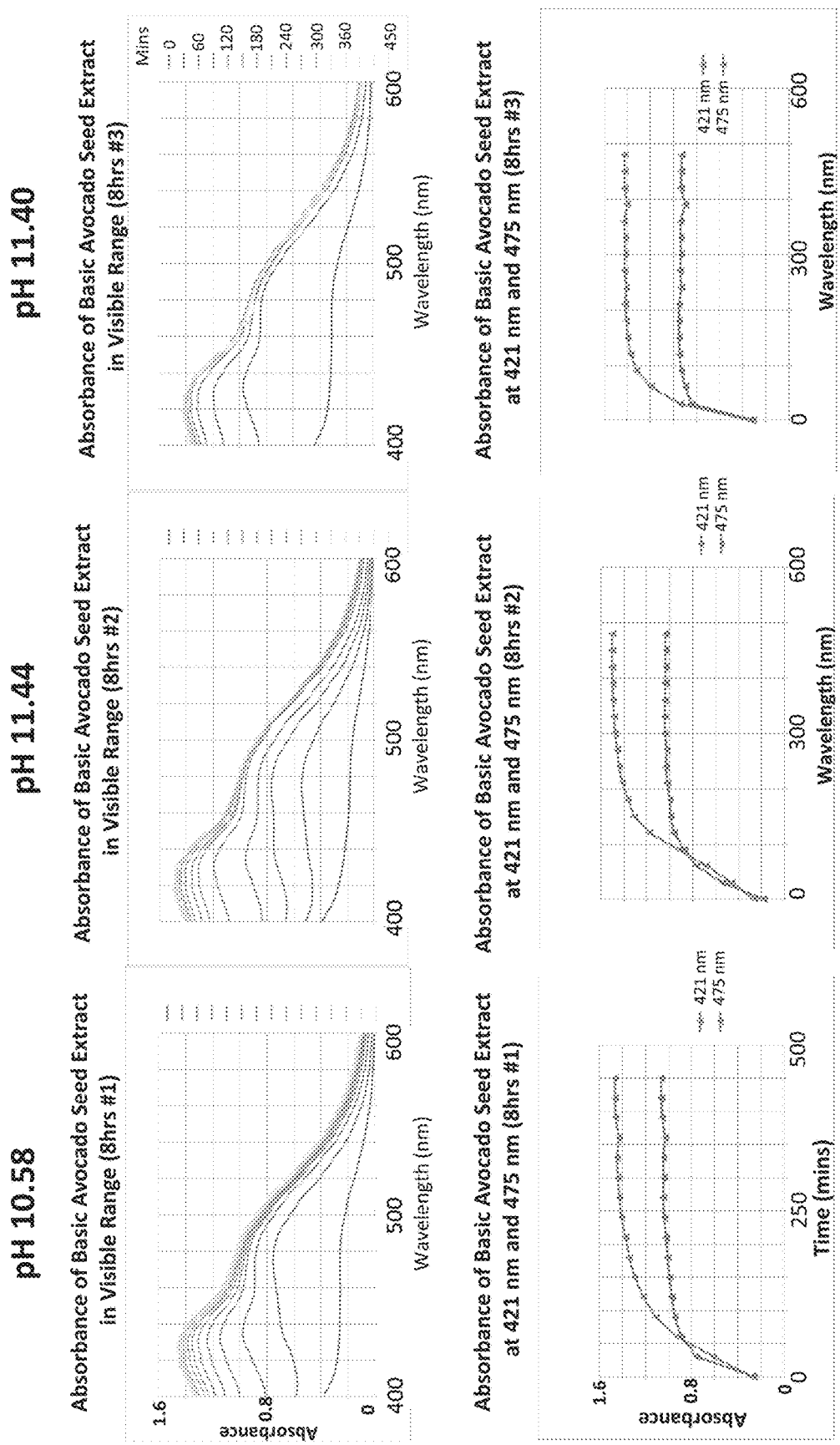
FIG. 53 depicts the absorbance of basic avocado extract (BAE) at, pH 10.58, 11.44 and 11.40.

Example 4: The Effect of Sodium Hydroxide Treatment on the Color of "Perseoranjin" Via Absorbance Measurement A basic solution was prepared for absorbance measurement. A 0.1% avocado extract was generated by diluting 10% avocado extract with deionized water. A 0.05% avocado extract was generated by diluting previous 0.1% avocado extract with 0.01 M NaOH. The 0.05% avocado extract was obtained with outset absorbance below 1 and pH 10-12. The Absorbance measurement of 0.05% basic avocado extract at time zero and followed by every 30 mins for 8 hours at pH 10.58, 11.44, and 11.40 (FIG. 53).

Absorbance of BAEs increases as time exceeds and observed color of the solution shifts from light yellow to orange. BAEs appeared orange due to their very low concentration of avocado extract (0.05%), however they actually are mixture of colors according to the UV spectrums. In the beginning of all BAEs spectrums, wavelengths of blue and green are greatly absorbed resulting in a red and orange mixture color of the basic avocado seed extract.

Figure 54:
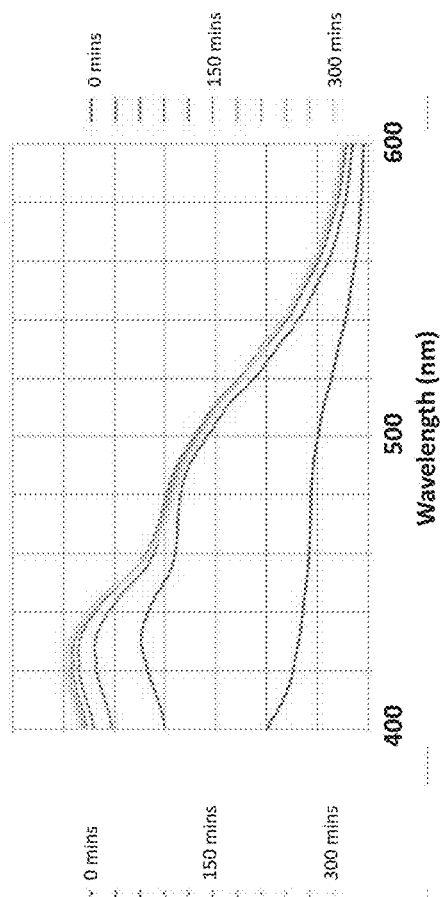
FIG. 54 depicts the absorbance of basic avocado extract at pH 10.12 and 11.24 and the absorbance measurement of 0.05% basic avocado extract at time zero and followed by every 30 mins for 5 hrs.
Figure 54:
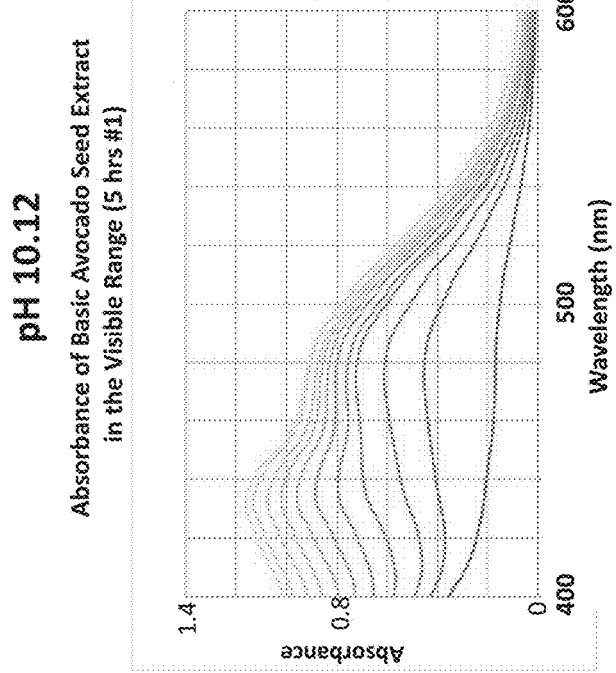
Figure 54:
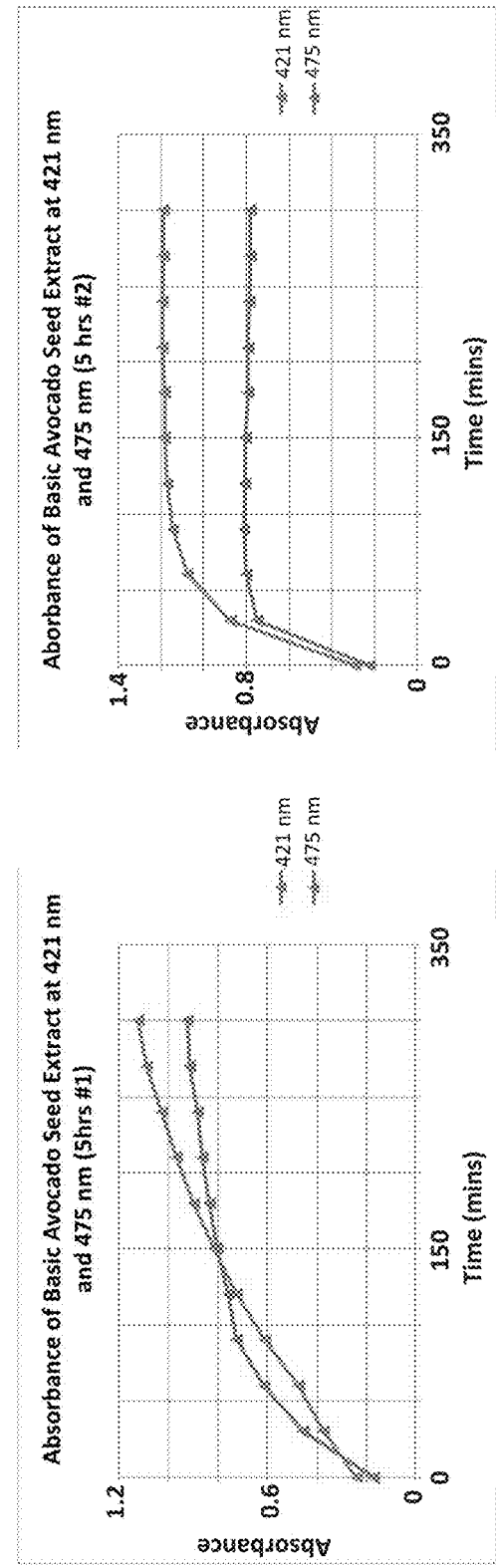

For example once the measurement was done at 90 mins according to FIG. 54, another peak gradually appears absorbing in the violet region. Thus, the extract has a present color mixture of yellow, orange and red after 5 hrs of base addition.

Absorbance measurement at time zero (comparison of absorbance at 400 nm) of experiment #3 was more delayed than experiments #1 and #2 creating a wide gap between graphs 0 mins and 30 mins of FIG. 5. This leads to absence of some important transition peaks. Experiment #5 below also gave similar results due to delay of measurement.

The maximum wavelengths observed were then examined separately. For both wavelengths, absorbance increases as a logarithmic function.

Figure 58:
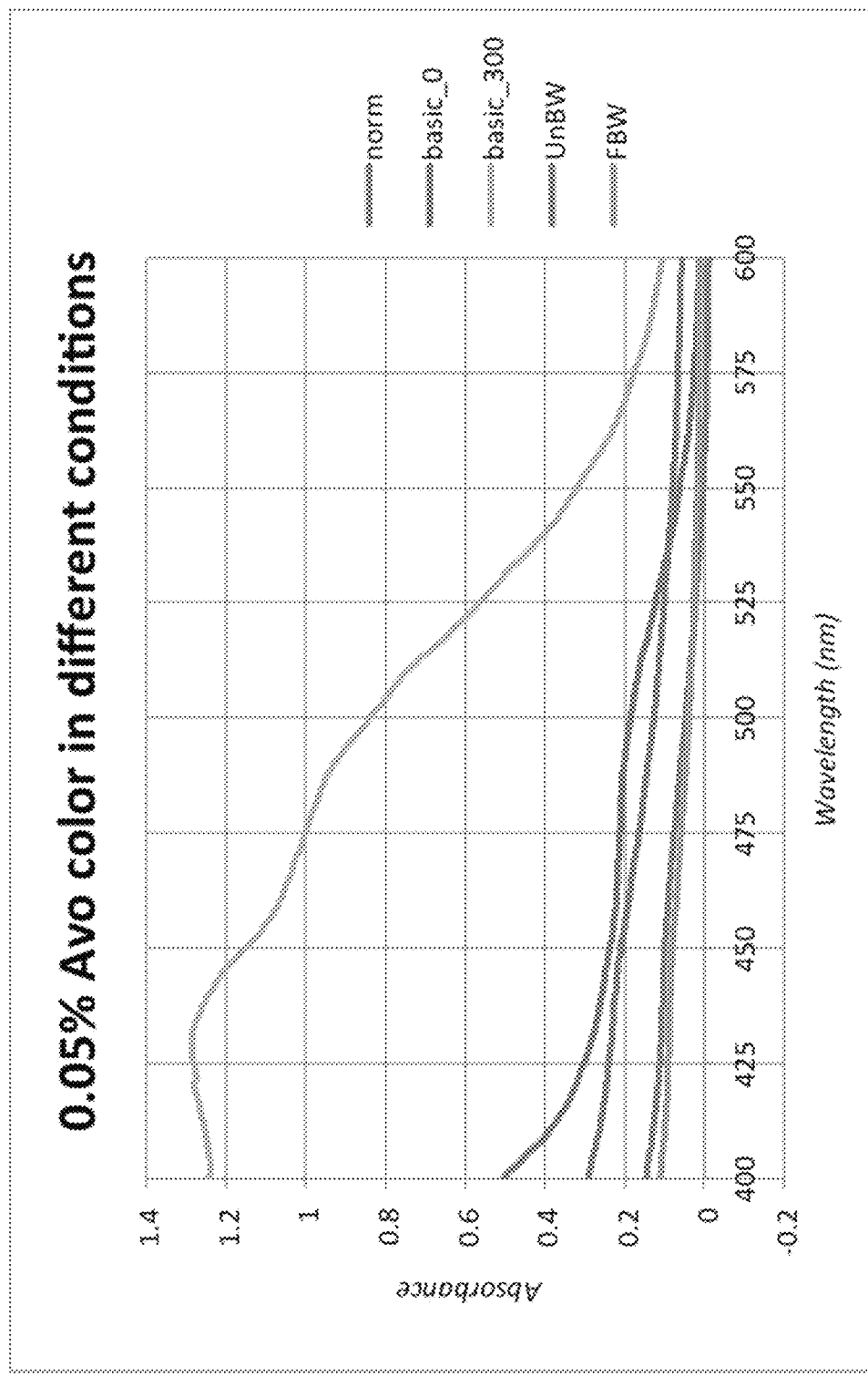
FIG. 58 depicts a comparison between absorbance of normal, basic and base washed avocado extracts.

Addition of NaOH to avocado extract causes an abrupt increase of absorbance in the first 100 mins and slowly decelerates as it reaches minute 200, while becoming fairly constant as it arrives at minute 300 and so on as observed in FIGS. 53, 54, and 58 above. Thus, following repetitive experiments were simply done for 5 hours or 300 mins in total.

A neutral solution was also prepared for absorbance measurement. BAE #5 was further used immediately after 5 hours to alter its pH from 11.35 to approximately pH 6 by addition of 0.1 M HCl. After absorbance measurement (5 hours), BAE #5 was pH 10.41; HCl before addition was pH 0.72. Table 4 shows the pH titration.

TABLE 4

| Condition | pH |
|---|---|
| Drop 1 | 9.85 |
| Drop 2 | 9.23 |
| Drops 3, 4 | 6.90 |
| Drop 5 and stir 2 mins | 6.26 |
| Drop 6 and stir 2 mins | 5.35 |
| 5 mins of stirring | 5.21 |

Figure 55:
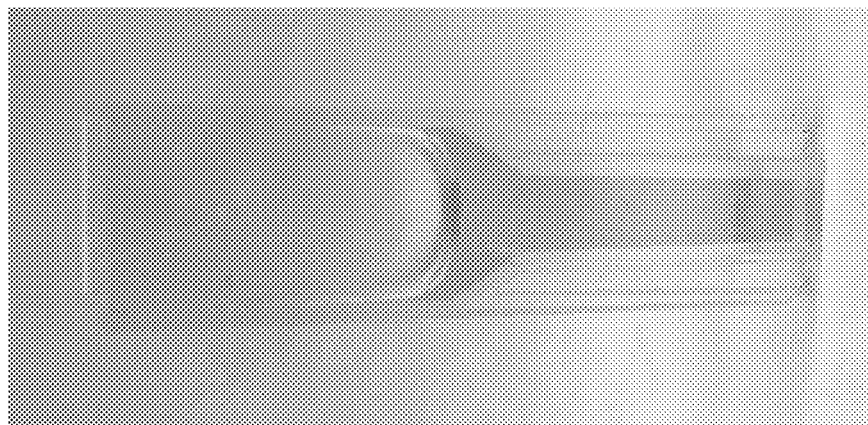
FIG. 55 depicts the precipitation of neutral avocado extract solution before and after pipette mixing.
Figure 55:
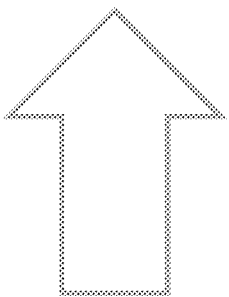
Figure 55:
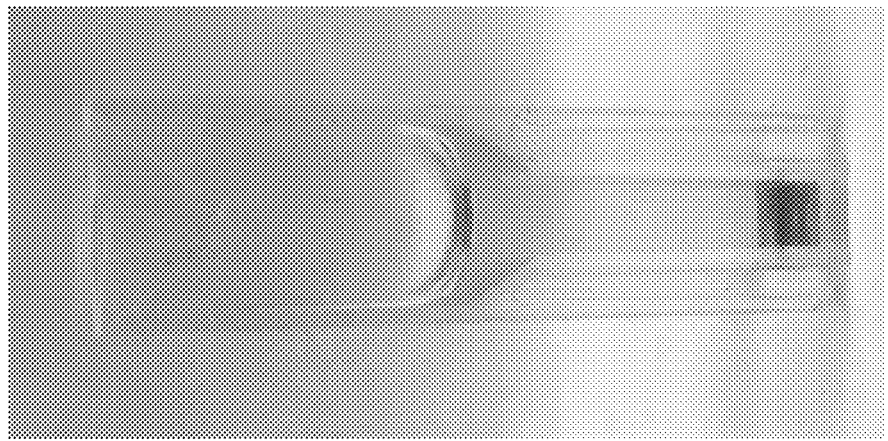
Figure 56:
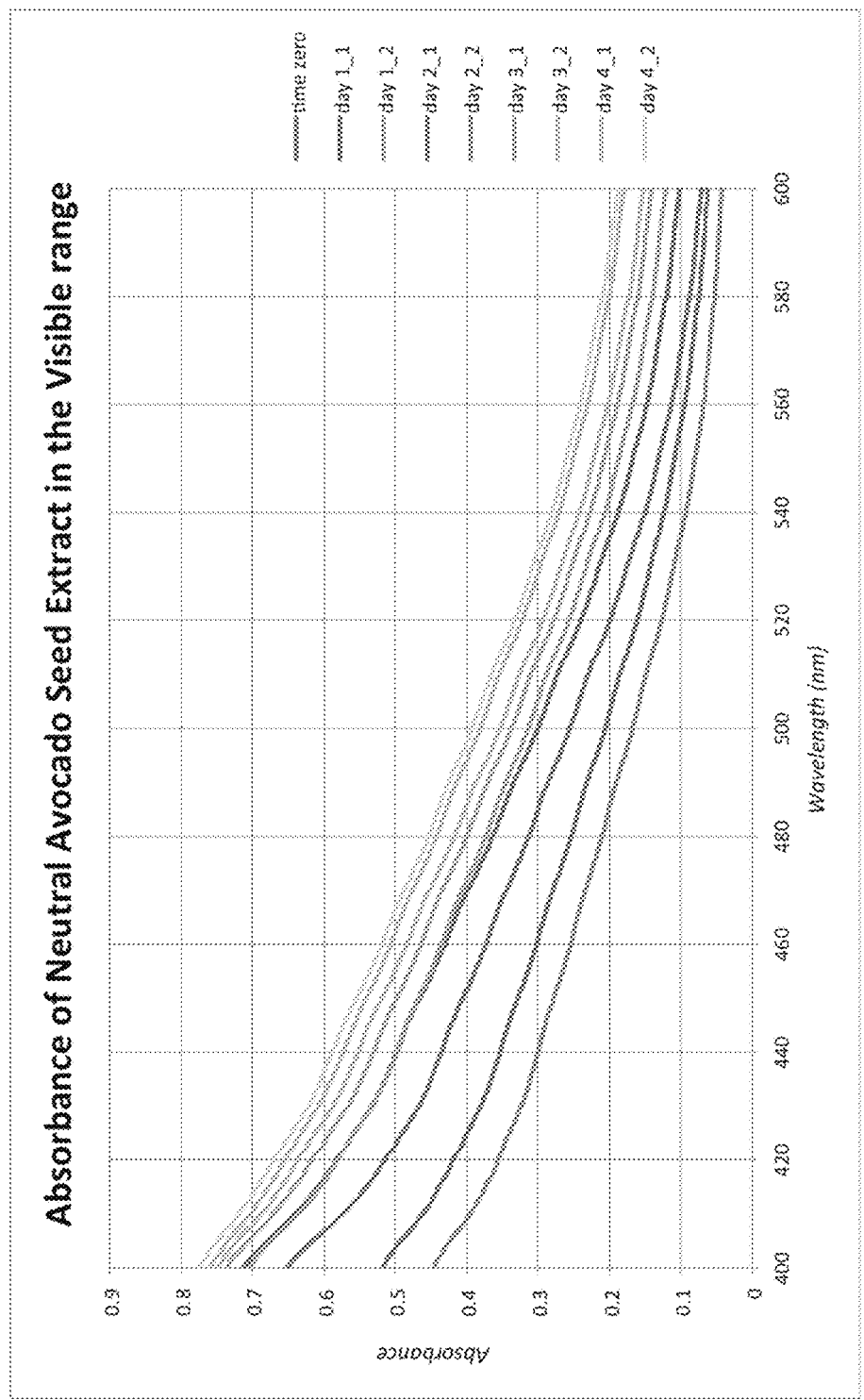
FIG. 56 depicts the absorbance of neutral avocado extract (NAE).

6 drops of HCl effectively neutralized BAE #5 according to pH value, however absorbance of NAE continued to increase as time exceeds, which can conclude that NaOH was not successfully removed. Orange precipitates were observed on day 1 of absorbance measurement pipette was used to disperse them before analysis (FIG. 55). Graphs for day2_1 and day2_2 are inaccurate due to uneven dispersion of colored precipitates (FIG. 56).

The precipitates of neutral avocado extract was tested for solubility. Solubility of the precipitates was tested with ethyl acetate and methanol. Both solvents were not able to remove them from the filter. Thus, precipitates did dissolve in neither ethyl acetate nor methanol.

Figure 57:
FIG. 57 depicts a comparison of base washed avocado extract unfiltered and filtered by the syringe.

Normal, basic and base washed avocado extracts were compared. Normal avocado extracts were prepared by generating a 0.05% avocado extract by diluting 10% avocado extract with deionized water and then its absorbance was measured. Basic avocado extracts were prepared by generating a 0.05% avocado extract by diluting 10% avocado extract with deionized water and then its absorbance was measured then its absorbance was measured at time zero and 300 mins. Base washed avocado extracts were generated by adding basic avocado extract (after 5 hrs) was then added to resin, which adsorbed the color pigments followed by washing them off by acid/EtOH and measuring absorbance of the final obtained solution. However, the solution that was only vacuum filtered contained pulverized resin from stirring. Thus, some of the cloudy yellow solution was filtered once again with a syringe filter and obtained a clear yellow solution. Both solutions were analyzed for their absorbance (FIG. 57).

The absorbance patterns of normal avocado extract (norm) and filtered base washed avocado extract (FBW) are very similar to one another. Thus, it could be concluded that NaOH was successfully removed from the final solution (FIG. 58).

Example 5: The Stability of Perseoranjin in the Presence of Chemicals Commonly Added to Foods Under Common Storage Conditions The results presented herein describe the stability of perseoranjin in chemicals.

The materials and methods employed in the experiments presented in this Example are now described.

Stability of Perseoranjin in Ascorbic Acid (Vitamin C) and Potassium Metabisulfite as Representative of Sulfur Dioxide at 32° C.

0.25% Avocado seed extract solution was added into Ascorbic acid in the range of 0-20 mg/mL and was added into Potassium metabisulfite in the range of 0, 25, 50, 75 and 100 ppm of Sulfur dioxide. The 0, 0.05, 0.1 and 0.2 g of Ascorbic acid in 10 mL of 0.25% Avocado seed extract solution and the 0, 4, 8, 12, 16 mg of Potassium metabisulfite in 10 mL of 0.25% Avocado seed extract solution were measured pH and absorbance in the visible range (400-600 nm) by using pH meter and uv-vis spectrophotometer once a week and were incubated at about 32° C.

Stability of Perseoranjin in the Presence of Proteins by Using Gelatin, Casein, and Cherry Flavoring as Representative of Benzaldehyde at 4° C.

0.25% Avocado seed extract solution was added into 0.1% Gelatin, 2% Casein which was stirred at 55° C. for 10 mins to better Casein dissolvable and 0.2% Cherry flavoring. The 0.01 g of Gelatin in 10 mL of 0.25% Avocado seed extract solution, the 0.2 g of Casein in 10 mL of 0.25% Avocado seed extract solution and the 0.02 mL of Cherry flavoring in the solution of 9.73 mL of deionized water and 0.25 mL of 10% avocado seed extract solution were measured pH and absorbance in the visible range (400-600 nm) by using pH meter and uv-vis spectrophotometer once a week and were kept refrigerated (4° C.).

The results of the experiments presented in this Example are now described.

Thermal Stability Test of Avocolor in Presence of Ascorbic Acid at 32° C.

Amounts of Ascorbic acid or Vitamin C including 0, 0.05, 0.1 and 0.2 g=were in the range of 0-20 mg/mL (0, 5, 10, 20 mg/mL) were added into 10 mL of 1% Avocolor solution (1 ml of 10% Avocolor solution and 9 mL of deionized water) These concentrate ratio solution gave too high color intensity, the absorbance peaks exceeded one. Thus, the high concentration were diluted to/4 or 0.25% Avocolor solution (used 0.25 mL solution and 0.75 mL deionized water) before absorbance measurement.

The wavelengths of indigo and blue were absorbed resulting in orange-yellowish color but all baseline solutions did not diluted to ¼ in absorbance measurement, so reference solution (Ascorbic acid in deionized water) did not diluted as Ascorbic acid in Avocolor solution when the absorbance peaks were measured day 0.

Figure 59:
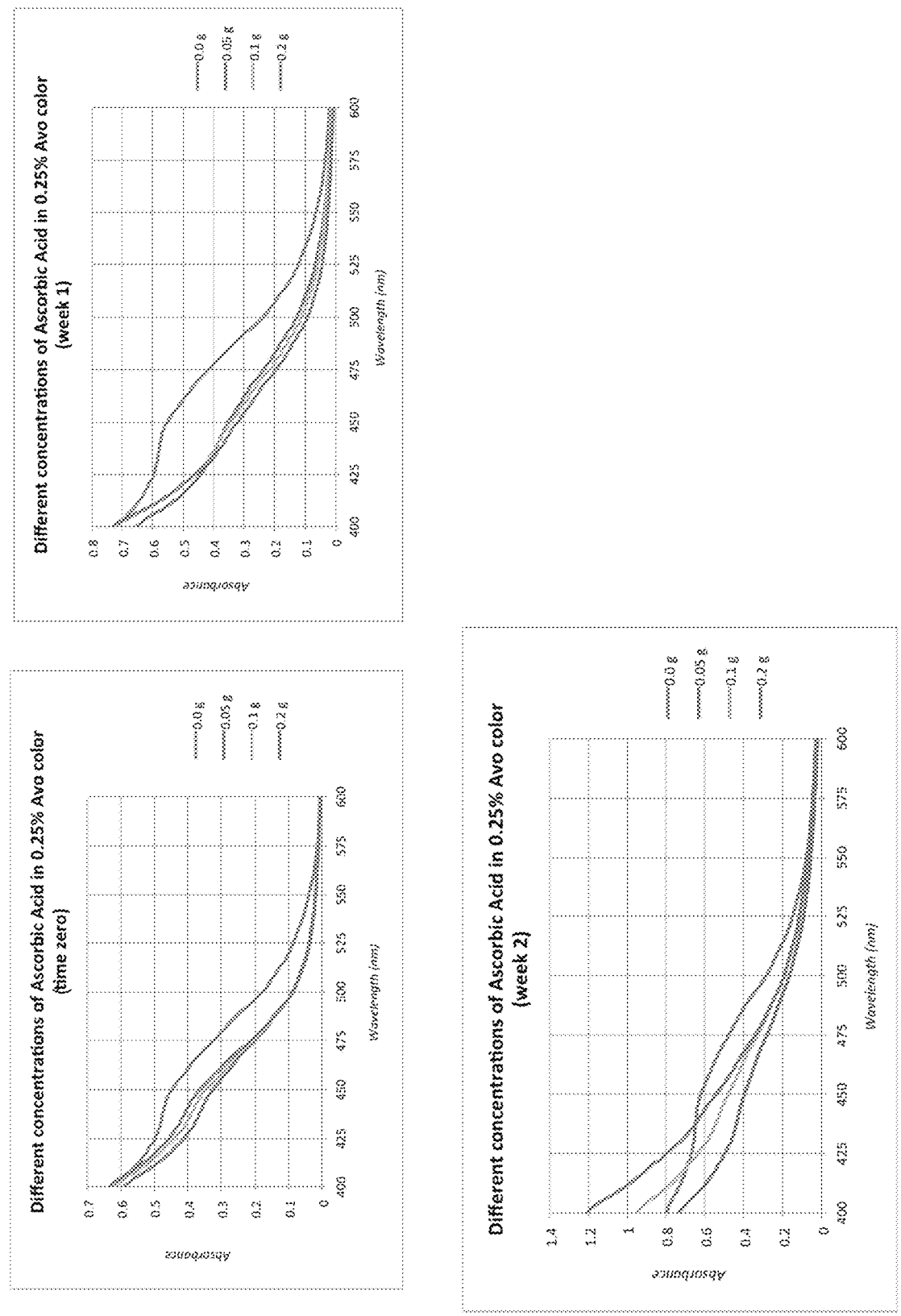
FIG. 59 depicts the absorbance of different concentrations of Ascorbic Acid in 0.25% Avocolor over 2 weeks.
Figure 60:
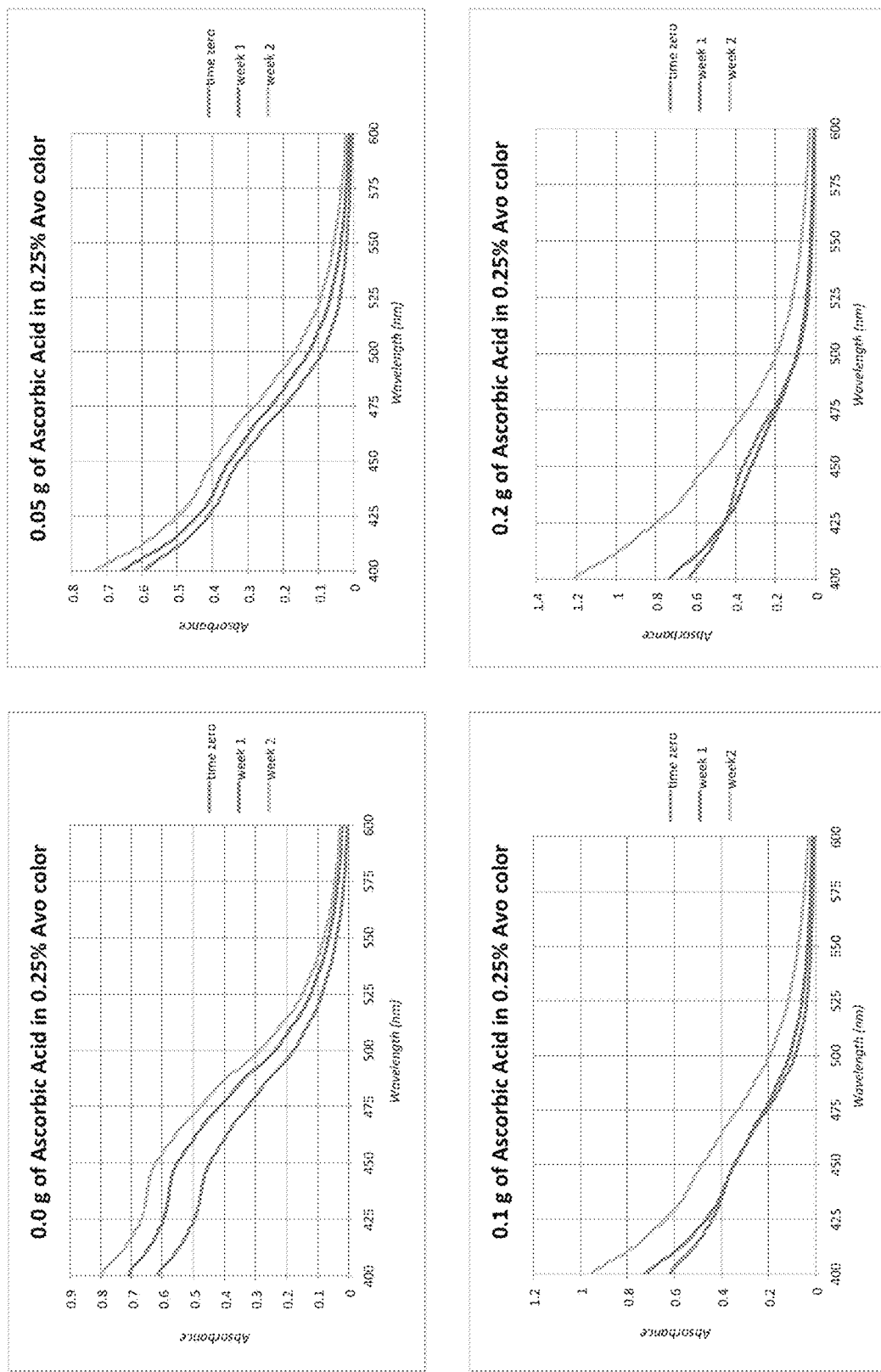
FIG. 60 depicts the absorbance of Ascorbic Acid in 0.25% Avocolor over 2 weeks.

The color of reference solution used in absorbance measurement was translucent colorless, then reference solution turned yellow after one week and got darker yellowish color over time caused by a browning reaction of Ascorbic acid oxidation as its reacted with oxygen which affected from the heat at 32° C. in incubator. The color of Ascorbic acid added Avocolor solution was lighter yellow-orangish than the standard solution (Avocolor solution) at time zero and then got darker orangish over time due to the Ascorbic acid oxidation reaction because the wavelengths of indigo and blue were more absorbed over the time resulting in the absorbance peak of Avocolor solution added Ascorbic acid increased (FIGS. 59-60).

Figure 61:
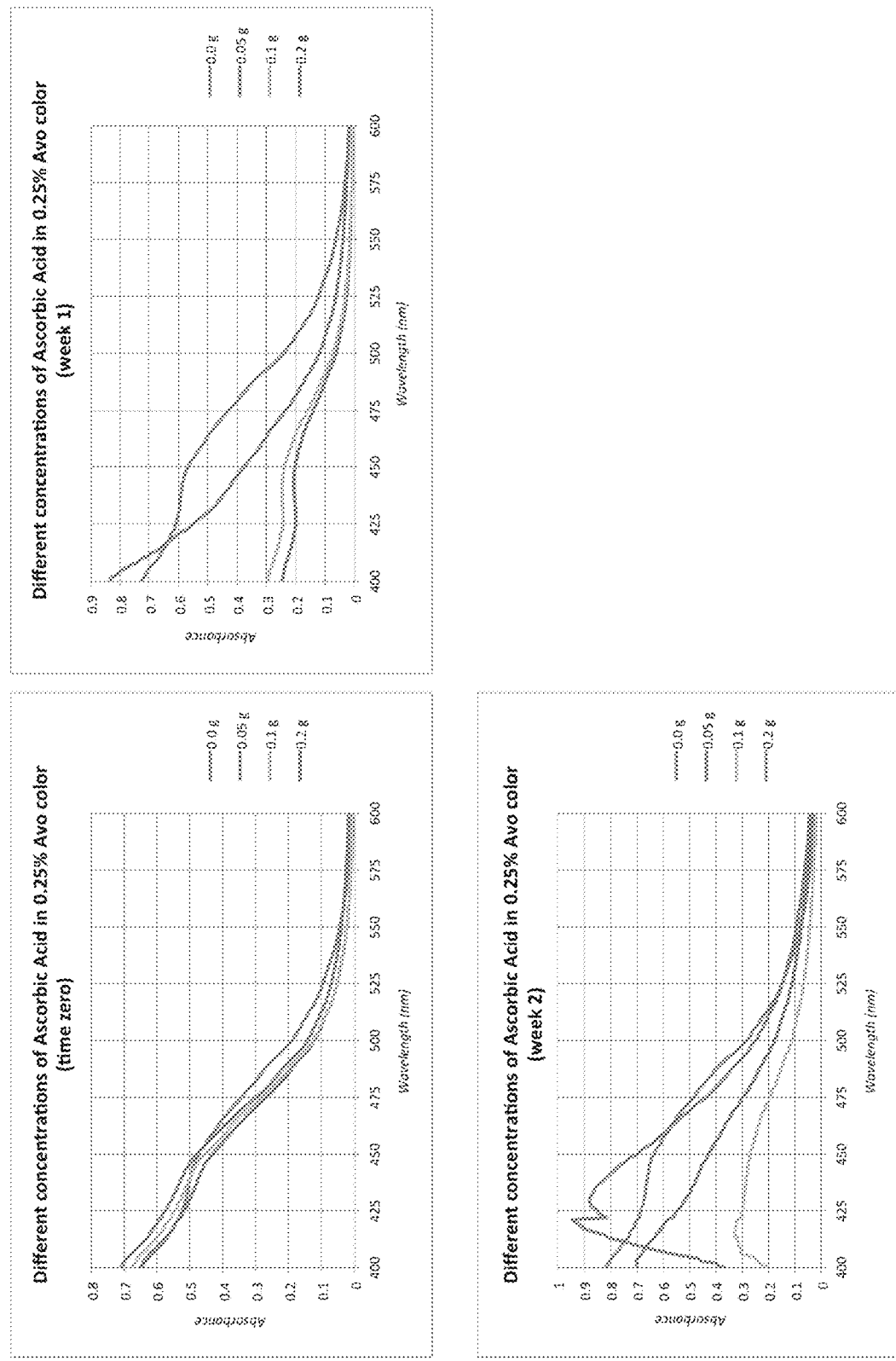
FIG. 61 depicts the absorbance of different concentrations of Ascorbic Acid in 0.25% Avocolor over 2 weeks.
Figure 62:
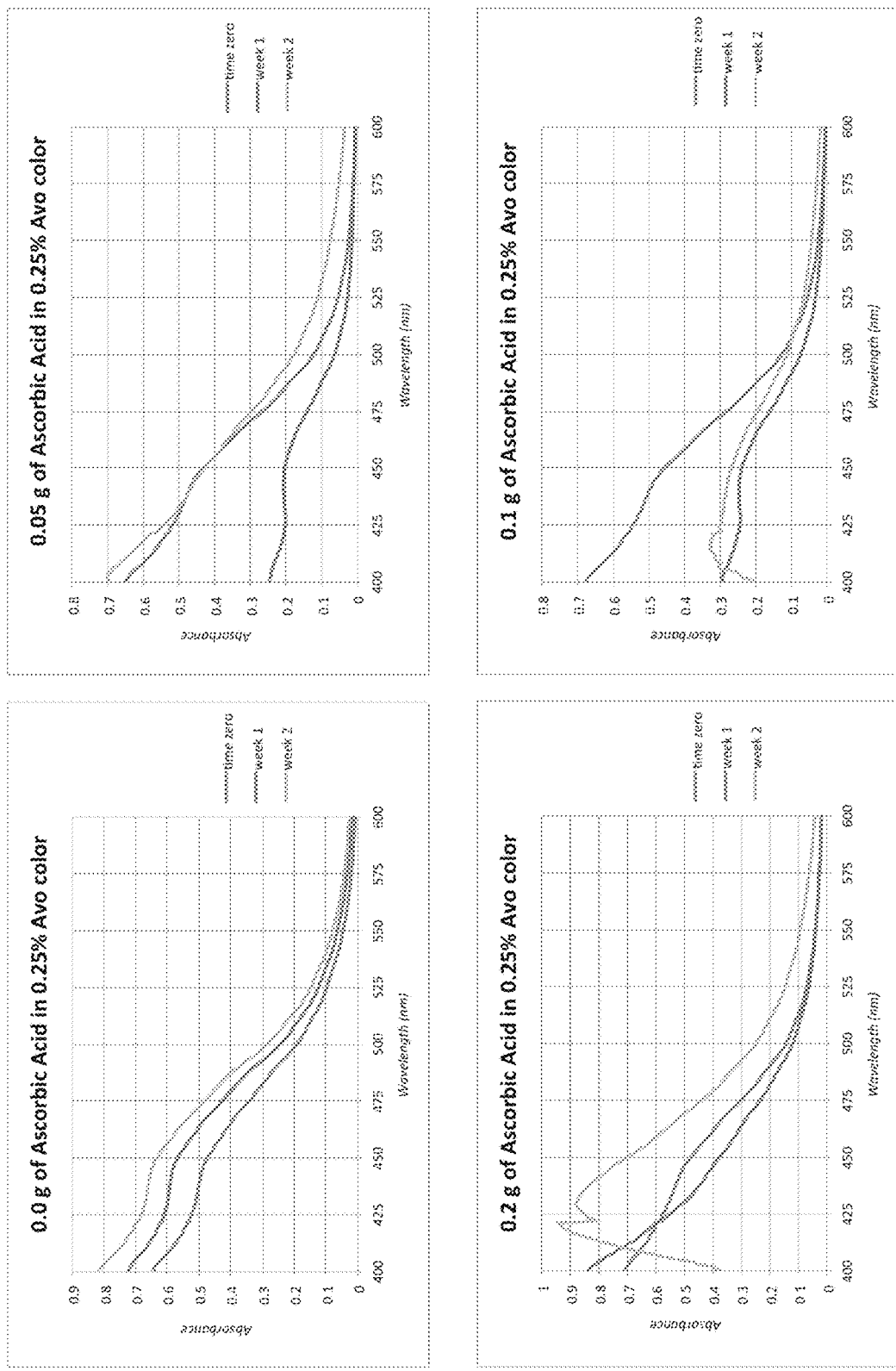
FIG. 62 depicts the absorbance of Ascorbic Acid in 0.25% Avocolor over 2 weeks.
Figure 63:
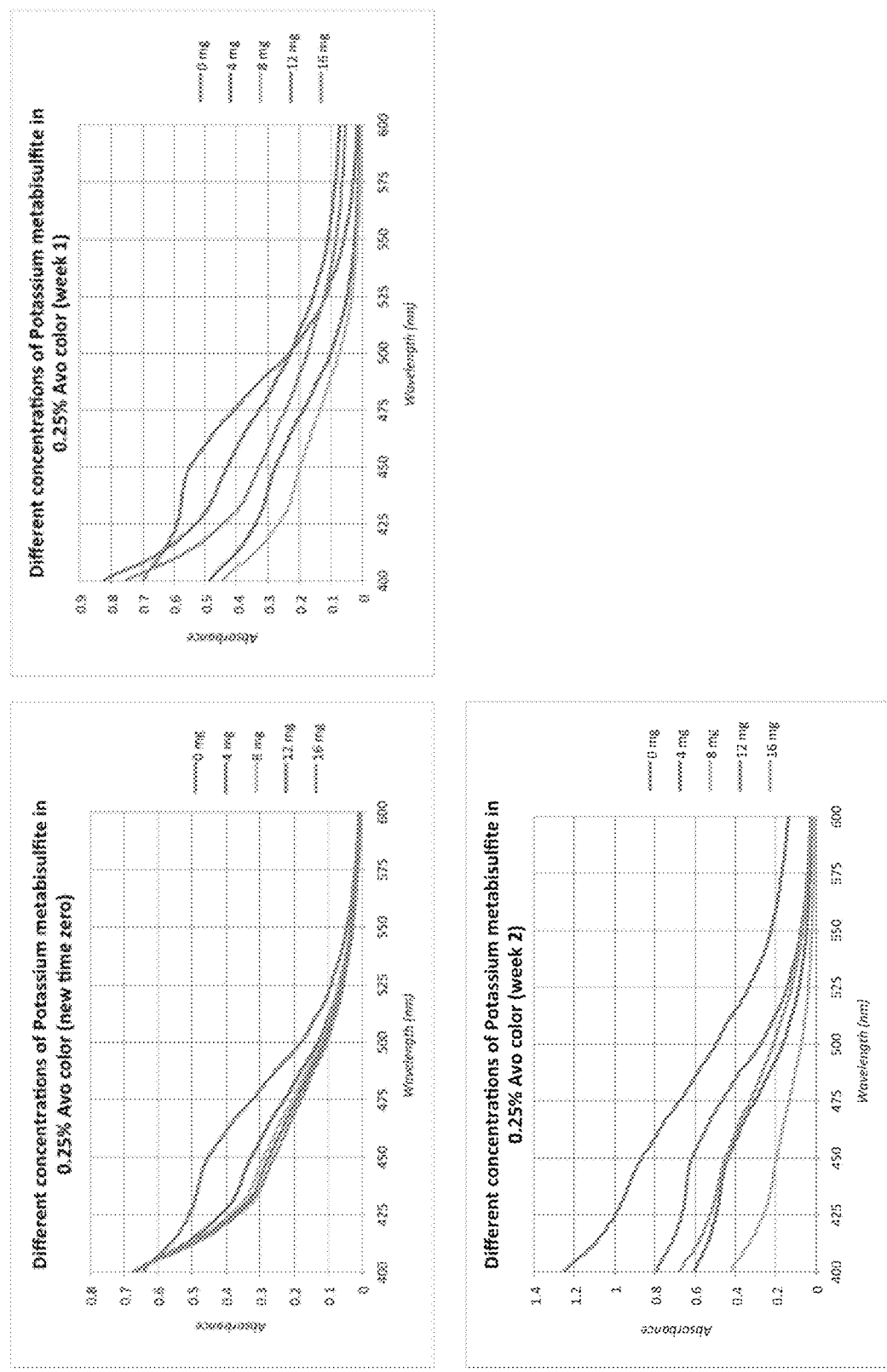
FIG. 63 depicts the absorbance of different concentrations of Potassium metabisulfite in 0.25% Avocolor over 2 weeks.
Figure 64:
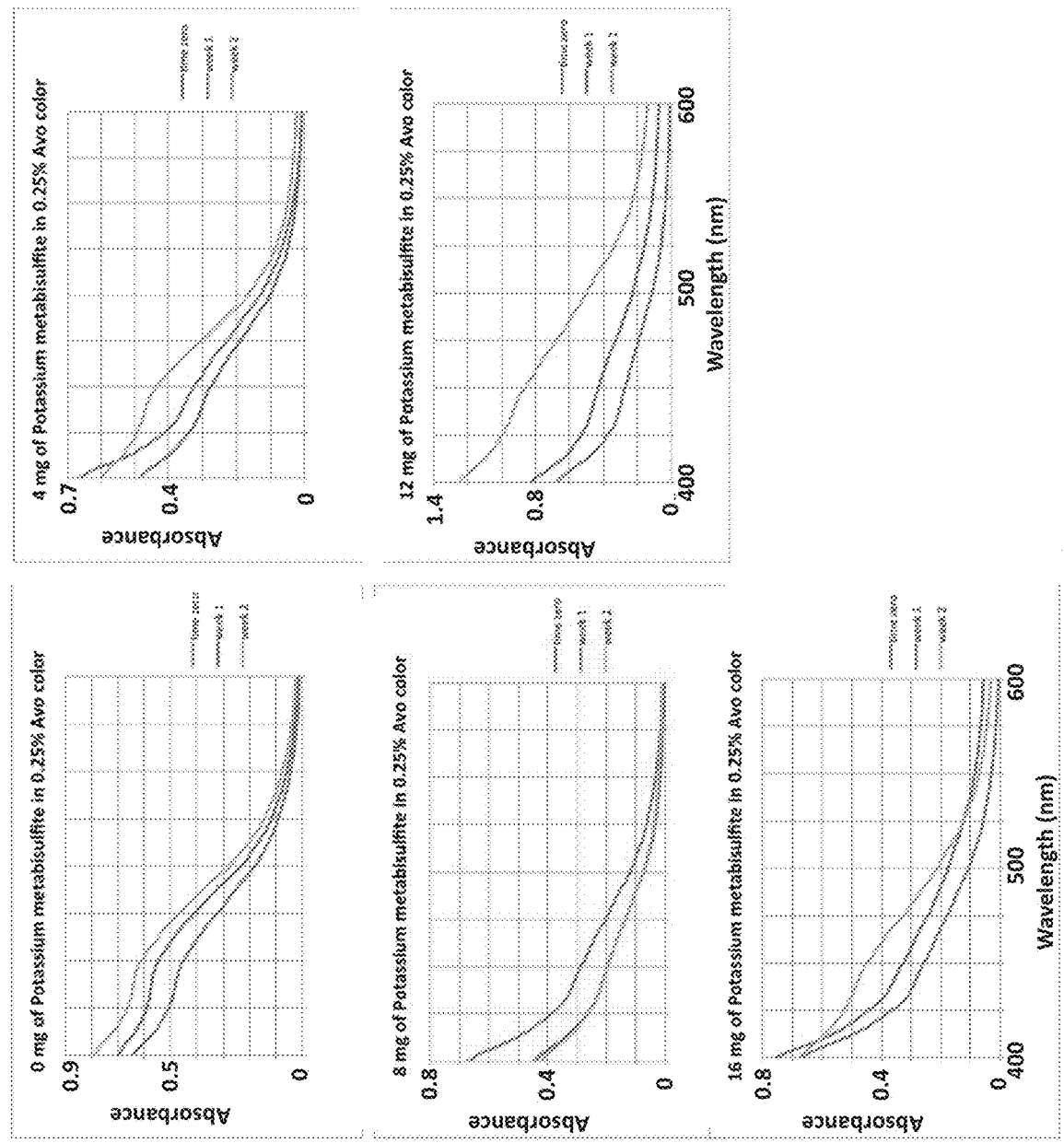
FIG. 64 depicts the absorbance of Potassium metabisulfite in 0.25% Avocolor over 2 weeks.

These experiments were repeated a second time (FIGS. 61-62). Table 5 shows the pH of different concentrations of Ascorbic acid (AA) in 1% Avocado seed extract solution in 2 weeks.

TABLE 5

|  | Day 0 | Week 1 | Week 2 |
|---|---|---|---|
| 0 g AA in 1% Avocolor | 4.39 | 4.11 | 4.35 |
| 0.05 g AA in 1% Avocolor | 3.07 | 2.01 | 2.20 |
| 0.1 g AA in 1% Avocolor | 2.87 | 1.96 | 2.04 |
| 0.2 g AA in 1% Avocolor | 2.72 | 1.82 | 1.93 |

The Avocolor solution that added Ascorbic acid turned dark orange which was similar to the standard solution but the highest concentration got darker orange than the standard solution. The reference solution color which Ascorbic acid added turned darker yellowish from week 1 by a browning reaction of Ascorbic acid oxidation as its reacted with oxygen which affected from incubator's heat at 32° C. Moreover, the reference solution of 0.2 g Ascorbic acid added still was the lightest yellowish reference solution.

The wavelengths of indigo and blue were absorbed more than week 1 resulting in the absorbance peak of the standard solution and 0.5 g Ascorbic acid added solution increased due to the color turned darker orange. The absorbance peak of Avocolor solution that 0.1 and 0.2 g Ascorbic acid added were different from others due to the pH changed and color changed from Ascorbic acid oxidation reaction.

Avocolor solution which Ascorbic acid added turned darker orange yellowish over time due to a browning reaction of Ascorbic acid oxidation as its reacted with oxygen which affected from incubated at around 32° C. but pH of Avocolor solution that Ascorbic acid added decreased over one week and increased in week 2 but did not exceed pH at time zero.

Thermal Stability Test of Avocolor in Presence of Potassium Metabisulfite at 32° C.

Potassium metabisulfite ($K_2S_2O_5$) in the amounts of 0, 4, 8, 12 and 16 g, which were in the range of 0-100 PPM of Sulfur dioxide, $SO_2$ (0, 25, 50, 75 and 100 PPM) were dissolved in 0.25% Avocolor (0.25 ml of 10% solution and 9.75 mL of deionized water).

The Avocolor solution that added Potassium metabisulfite turned gently lighter orangish color from the standard solution (Avocolor solution) at time zero because the wavelengths of indigo and blue of Potassium metabisulfite added were less absorbed than the standard solution. The absorbance peaks were gently decreased due to the higher concentration of Potassium metabisulfite added. The different concentrations of Avocolor solution that added Potassium metabisulfite approximately had pH 3.5-4. Table 6 shows the pH of different concentrations of Potassium metabisulfite in 0.25% Avocolor in 1-2 weeks.

TABLE 6

|  | Experiment 1 | | Experiment 2 | | |
|---|---|---|---|---|---|
|  | Day 0 | Week 1 | Day 0 | Week 1 | Week 2 |
| 0 mg $K_2S_2O_5$ in 0.25% Avocolor | 3.93 | 4.37 | 4.33 | 3.76 | 4.26 |
| 4 mg $K_2S_2O_5$ in 0.25% Avocolor | 3.95 | 3.93 | 4.17 | 2.50 | 2.88 |
| 8 mg $K_2S_2O_5$ in 0.25% Avocolor | 3.93 | 3.91 | 4.30 | 2.96 | 2.76 |
| 12 mg $K_2S_2O_5$ in 0.25% Avocolor | 3.97 | 3.58 | 4.32 | 3.12* | 3.68 |
| 16 mg $K_2S_2O_5$ in 0.25% Avocolor | 3.94 | 4.09* | 4.30 | 3.15* | 3.33 |

The reference solution color did not change from the beginning. The color of Avocolor solution to which 16 mg Potassium metabisulfite added was similar to the standard solution which were darker orangish, 4 mg Potassium metabisulfite added was darker yellowish, 8 mg Potassium metabisulfite added was the most pale yellow, and 12 mg Potassium metabisulfite added was the darkest orangish color and was strong smelly in two weeks.

The pH changed did not depend on the concentration of Potassium metabisulfite added into 0.25% Avocolor solution. In addition, the pH decreased after one week by incubated at 32° C. and increased after two weeks but not exceeded pH at time zero besides 8 mg $K_2S_2O_5$ added which decreased over time.

Thermal Stability Test of Avocolor in Presence of Gelatin at 4° C.

Figure 65:
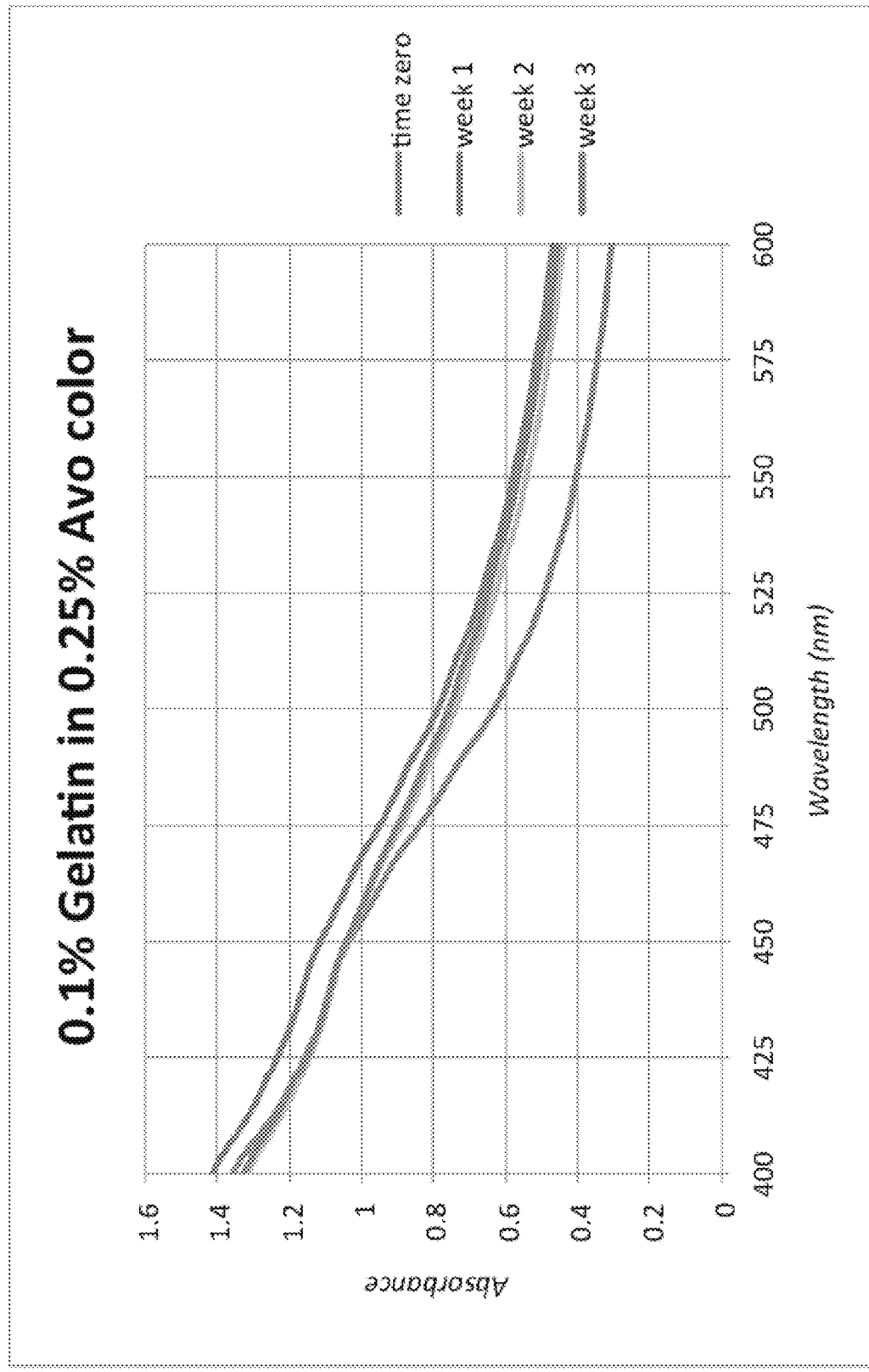
FIG. 65 depicts the absorbance of 0.1% Gelatin in 0.25% Avocado seed extract solution over 3 weeks.

The absorbance of 0.1% Gelatin in 0.2 5% Avocado seed extract solution was measured over 3 weeks (FIG. 65). The pH of 0.1% Gelatin in 0.25% Avocolor was approximately 4.4-4.5. The wavelengths of blue were absorbed resulting in orange mixture of the 0.1% Gelatin in 0.25% Avocolor solution which had three layers; clear orange solution on the top, muddy orange solution in the middle and orange precipitate at the bottom due to 0.1% Gelatin was precipitated by 0.25% Avocolor. The solution of 0.1% Gelatin in 0.25% Avocolor did not changed in 3 weeks. Table 7 shows the change in pH of 1% Gelatin in 0.25% Avocado seed extract solution over 3 weeks.

TABLE 7

|  | Day 0 | Week 1 | Week 2 | Week 3 |
|---|---|---|---|---|
| pH | 4.53 | 4.55 | 4.50 | 4.47 |

The absorbance peak increased in a week because of observing more muddy orange solution and orange precipitate than at time zero but the absorbance peak decreased in week 2 and week 3 because of losing some cloudy solution and orange precipitate from transferring the solution to cuvette by pipette in absorbance measurement.

Thermal Stability Test of Avocolor in Presence of Casein at 4° C.

Figure 66:
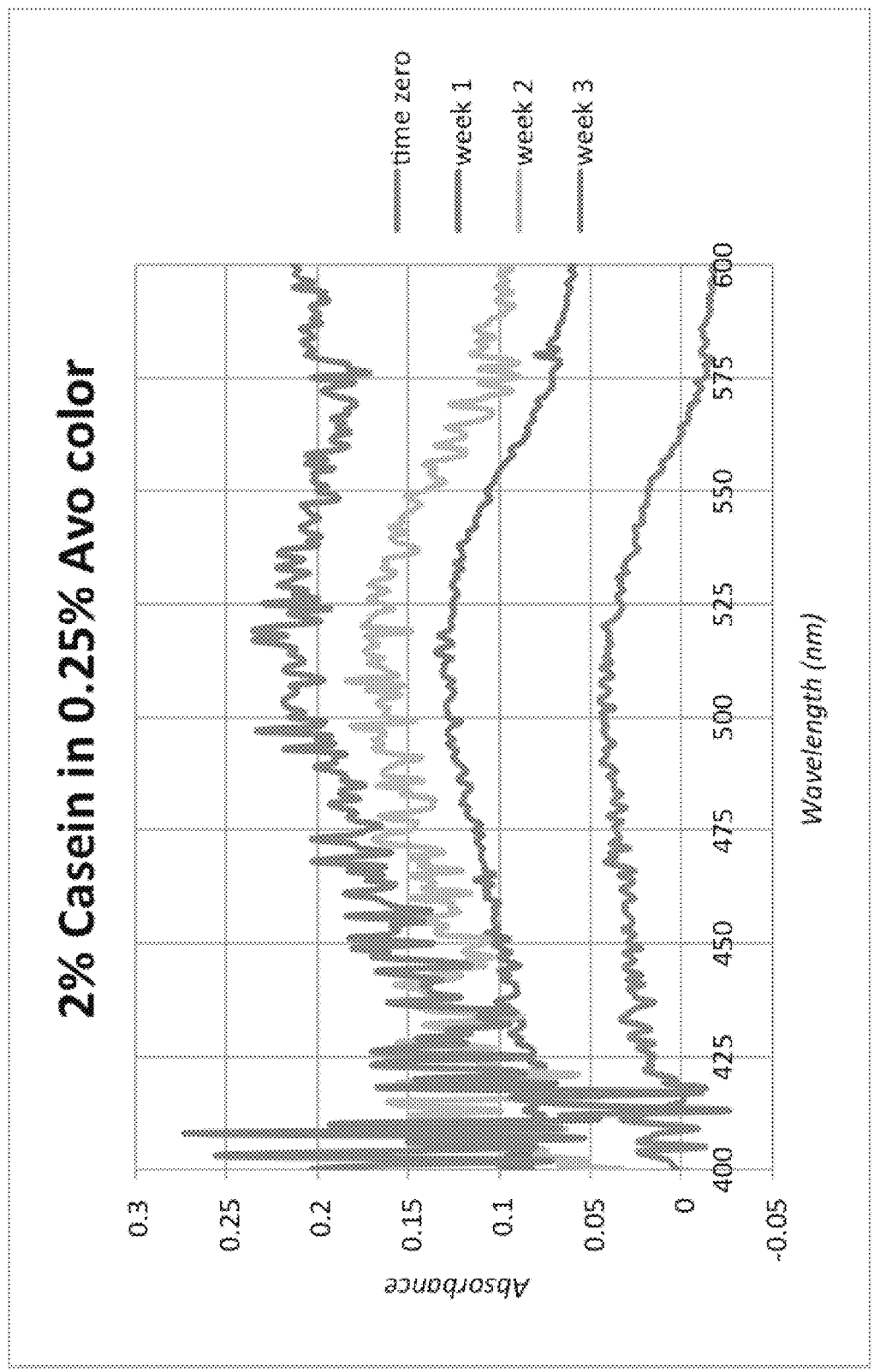
FIG. 66 depicts the absorbance of 2% Casein in 0.25% Avocado seed extract solution over 3 weeks.

The pH of 2% Casein in 0.25% Avocolor was approximately 6-7 in 3 weeks. The wavelengths of green were absorbed resulting in cloudy pink color of 2% Casein in 0.25% Avocolor (FIG. 66). Moreover, the cloudy pink solution did not changed in 3 weeks but the absorbance peaks gently increased over time. Table 8 shows the change in pH of 2% Casein in 0.25% Avocado seed extract solution over 3 weeks.

TABLE 8

|  | Day 0 | Week 1 | Week 2 | Week 3 |
|---|---|---|---|---|
| pH | 6.42 | 6.65 | 6.97 | 6.84 |

Thermal Stability Test of Avocolor in Presence of Cherry Flavoring at 4° C.

0.2% Cherry flavoring in 10 mL of 0.25% Avocolor was made by using 0.02 mL of Cherry flavoring in 10 mL 0.25% Avocolor (0.25 ml of 10% solution and 9.73 mL of deionized water).

Figure 67:
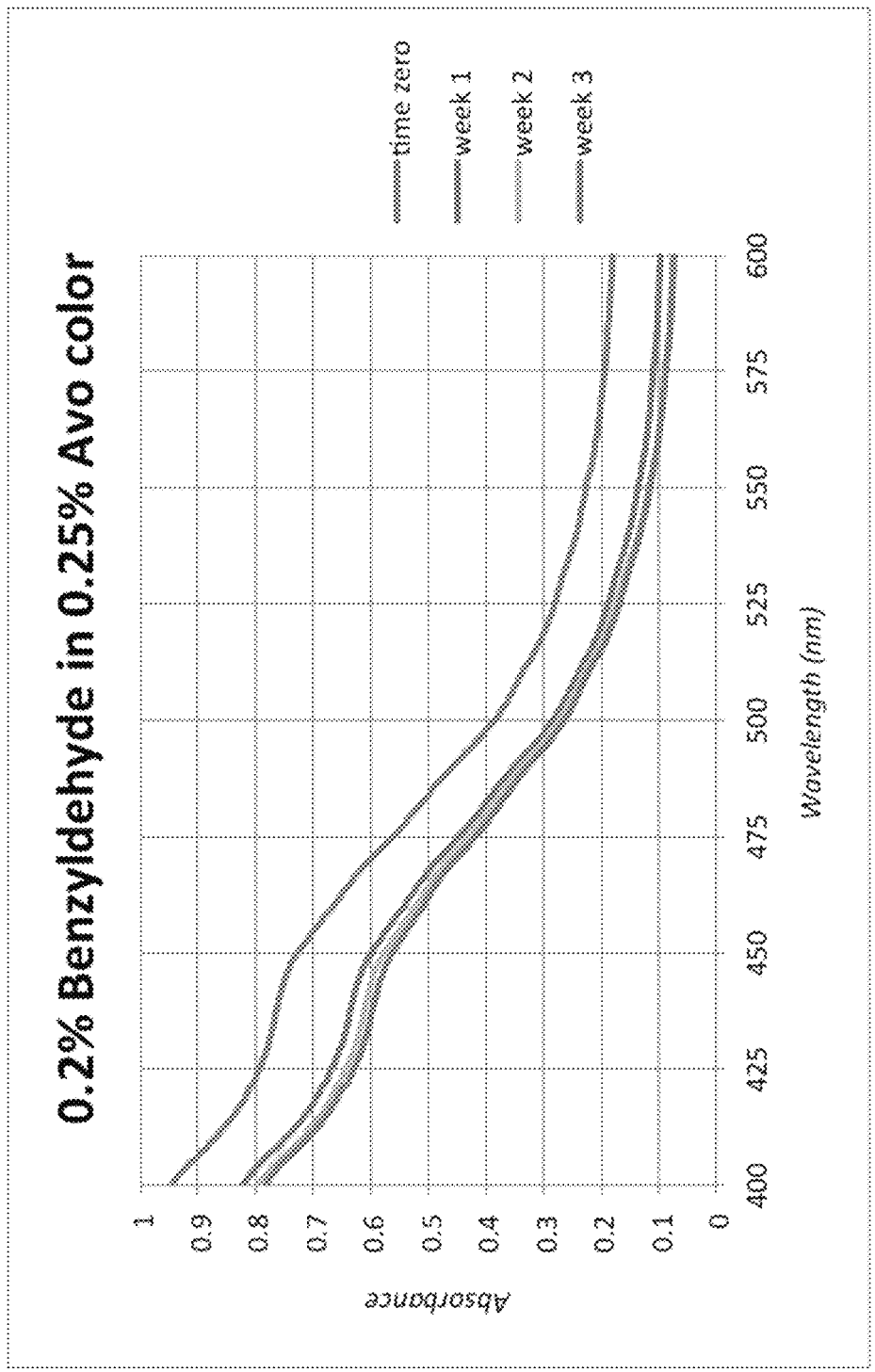
FIG. 67 depicts the absorbance of 0.2% Cherry flavoring in 0.25% Avocado seed extract solution over 3 weeks.

The pH of 0.2% Cherry flavoring in 0.25% Avocolor was approximately 4.3-4.4 in 3 weeks (Table 9). The wavelengths of indigo and blue were absorbed resulting in dark yellowish color of 0.2% Cherry flavoring in 0.25% Avocolor which did not changed the color in 3 weeks but the absorbance peaks decreased from time zero and gently decreased tendency of absorbance over time (FIG. 67).

TABLE 9

|  | Day 0 | Week 1 | Week 2 | Week 3 |
|---|---|---|---|---|
| pH | 4.45 | 4.42 | 4.45 | 4.33 |

Example 6: The Stability and Application of Perseoranjin in Food Matrices

The results presented herein demonstrates the stability of perseoranjin in foods such as yogurt, sprite, corn chips and white chocolate.

The materials and methods employed in the experiments presented in this Example are now described.

Stability of Perseoranjin in Plain Yogurt 2 mL of 1% Avocado seed extract solution was added into 5 g of plain yogurt compared to 0.2 mL of 10% Avocado seed extract solution which was added into 5 g of plain yogurt.

Stability of Perseoranjin in Sprite 1 mL of 1% Avocado seed extract solution was added into 10 mL of Sprite compared to 1 mL of 1% Avocado seed extract solution which was added into 10 mL of deionized water. 1 mL of 0.25%, 0.5% and 1% Avocado seed extract solution were added into 10 mL of Sprite and were then measured the absorbance in the visible range (400-600 nm) by using uv-vis spectrophotometer for 2 days.

Stability of Perseoranjin in Tostitos Corn Chip

One piece of Tostitos was sprinkled by Maltodextrin added Avocado seed extract powder (2.423% Avocado seed extract)

Stability of Perseoranjin in White Chocolate 5 g of white chocolate was melted by incubated at 32° C. for 1 hour and was then swirled and sprinkled by 0.1 g Maltodextrin added Avocado seed extract powder (2.423% Avocado seed extract)

The results of the experiments presented in this Example are now described.

Figure 68:
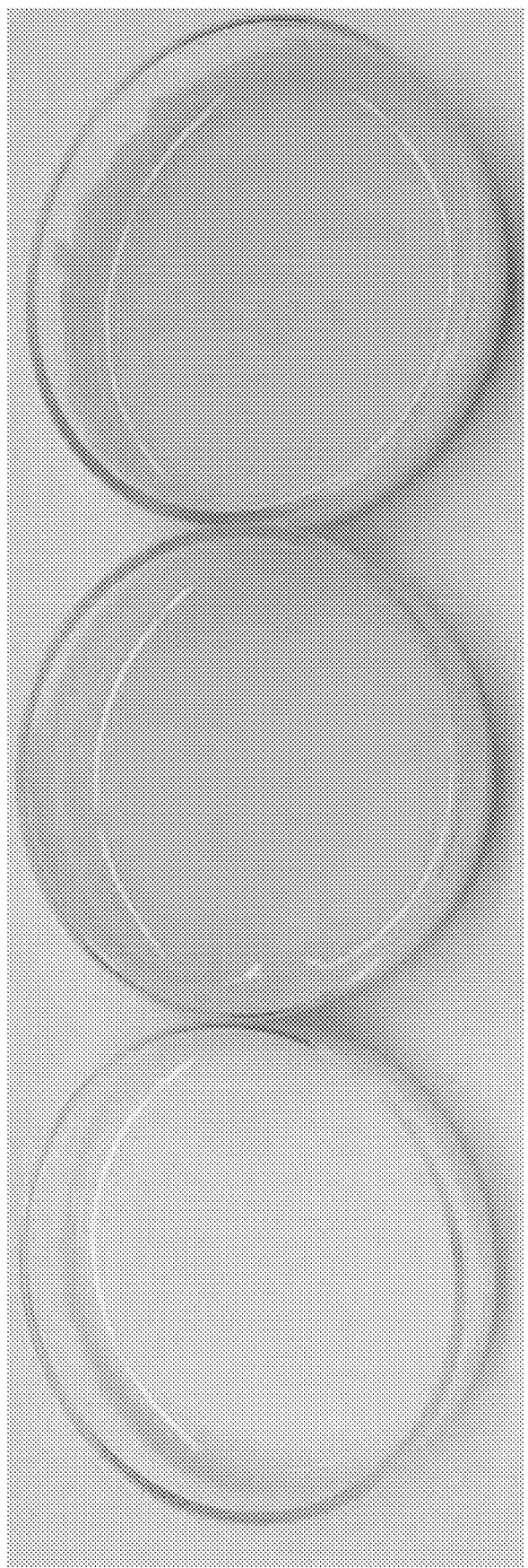
FIG. 68 depicts the color of 2 mL of 1% Avocolor solution compared to 0.2 mL of 1% Avocolor solution.

Perseoranjin in Plain Yogurt 2 mL of 1% Avocado seed extract solution was added into 5 g of plain yogurt compared to 0.2 mL of 10% Avocado seed extract solution which was added into 5 g of plain yogurt resulting in plain yogurt added 2 mL of 1% Avocolor was thinner than plain yogurt and plain yogurt added 0.2 mL of 1% Avocolor and was brighter orangish than plain yogurt added 0.2 mL of 10% Avocolor (FIG. 68).

Figure 69:
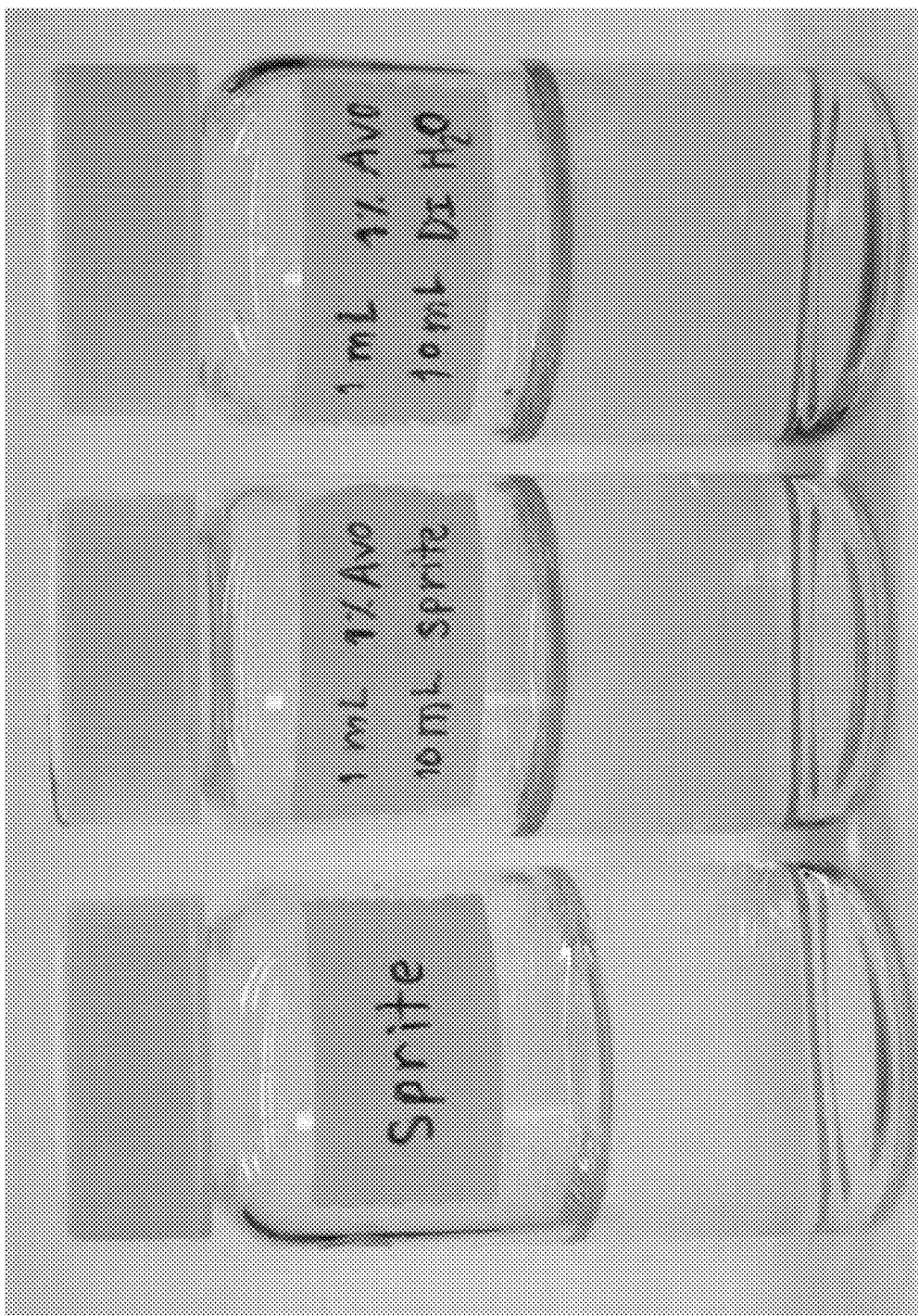
FIG. 69 depicts the color of 1% Avocolor solution in Sprite compared to 1% Avocolor solution in deionized water.

Perseoranjin in Sprite 1 mL of 1% Avocado seed extract solution was added into 10 mL of Sprite compared to 1 mL of 1% Avocado seed extract solution was added into 10 mL of deionized water resulting in Sprite added 1% Avocolor solution was brighter yellowish than 1% Avocolor solution (FIG. 69).

1 mL of 0.25%, 0.5% and 1% Avocado seed extract solution were added into 10 mL of Sprite and were then measured the absorbance in the visible range (400-600 nm) by using uv-vis spectrophotometer for 2 days.

Figure 70:
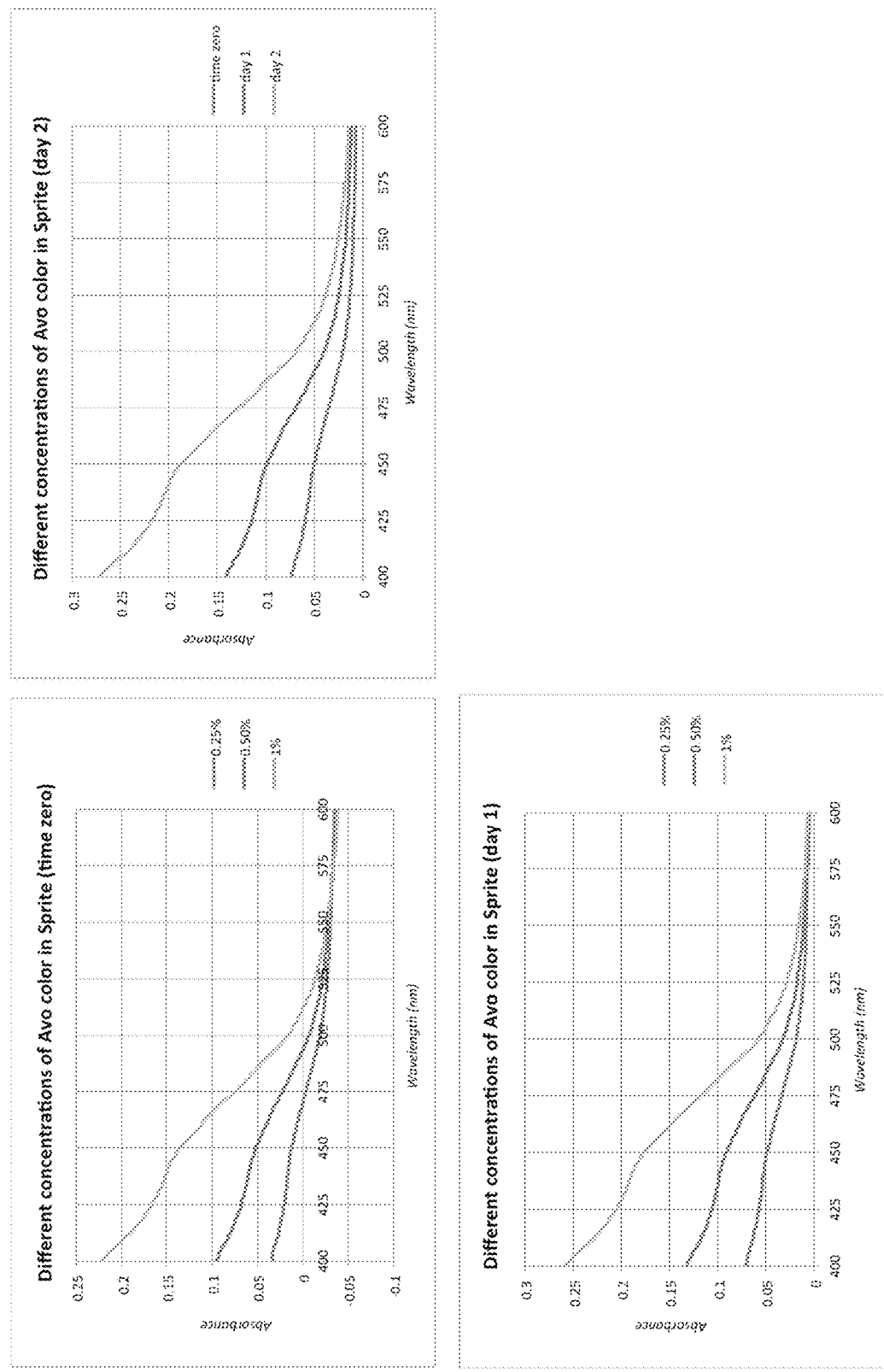
FIG. 70 depicts the absorbance of different concentrations of Avocolor in Sprite over 2 days.
Figure 71:
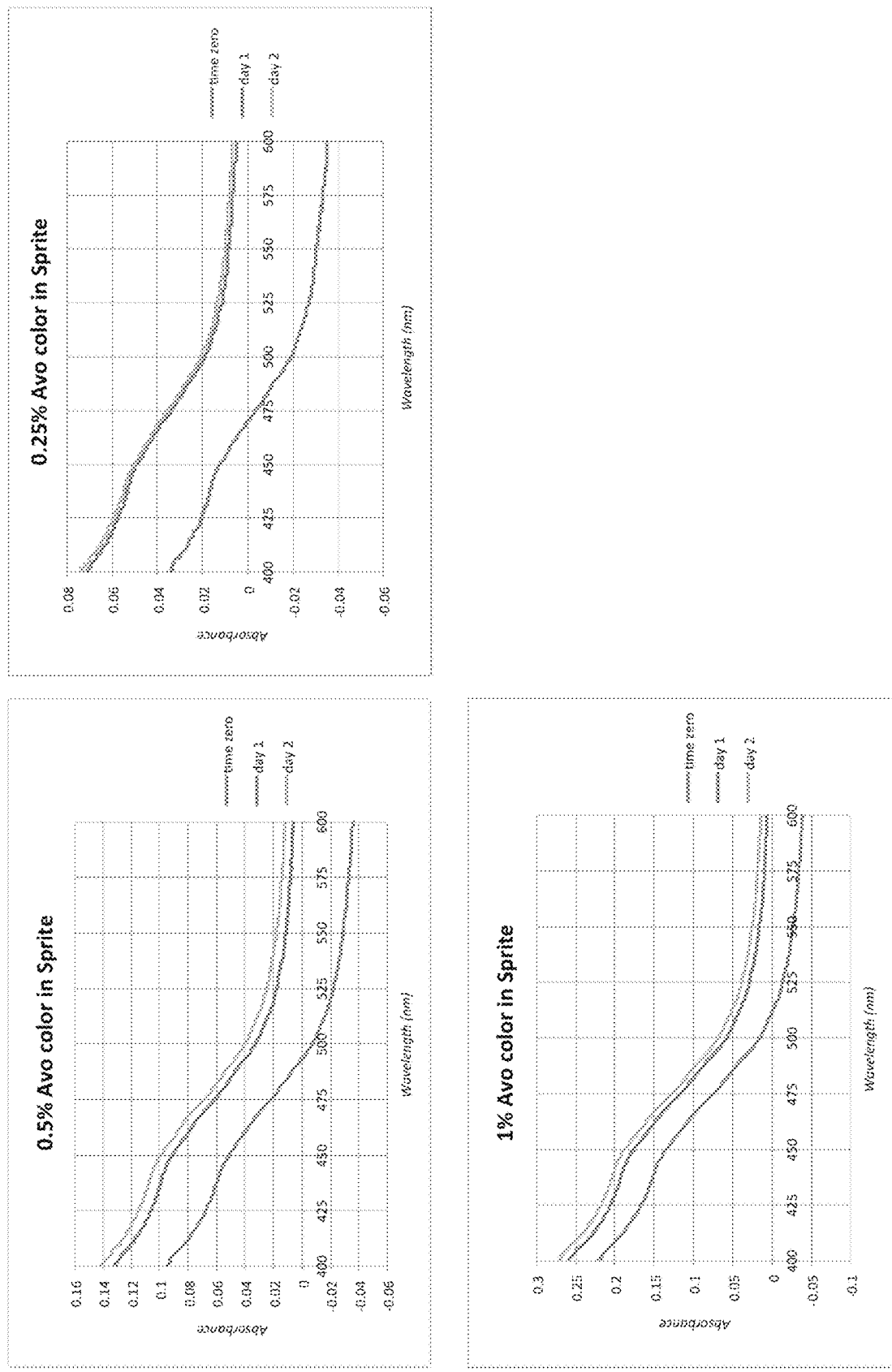
FIG. 71 depicts the absorbance of 1% Avocado seed extract solution in Sprite in 2 days
Figure 72:
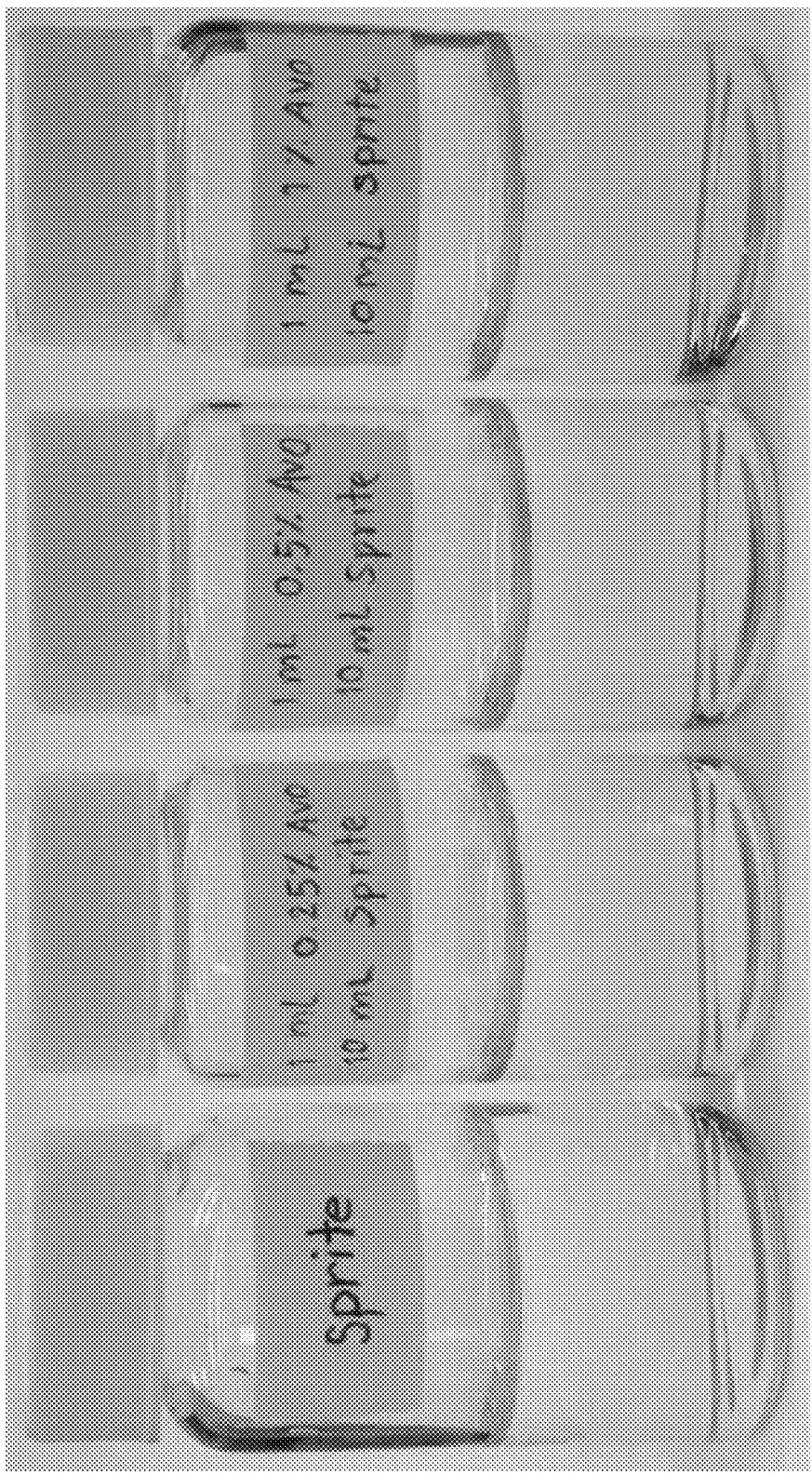
FIG. 72 depicts the colors of different concentration of % Avocolor solution in 10 mL of Sprite.

The wavelengths of indigo and blue were absorbed resulting in the yellowish solution. The higher concentration of % Avocolor solution, the higher yellowish color intensity due to the more absorbance peak. Moreover, the yellowish color of % Avocolor solution in 10 mL Sprite did not changed from the color at time zero (FIGS. 70-71).

The absorbance peaks were below 0 due to small bubbles in Sprite that used as baseline in the absorbance measurement at time zero. The next day, the absorbance peaks increased from the peaks at time zero and gently increased in Day 2.

Perseoranjin in Corn Chips

Figure 73:
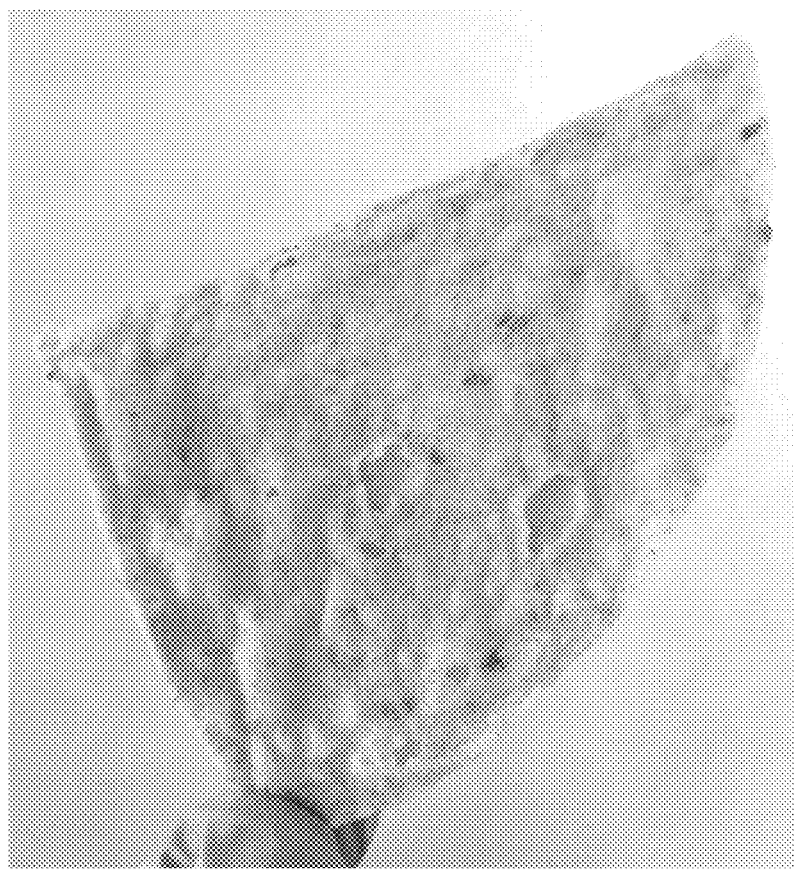
FIG. 73 depicts the colors of Maltodextrin Avocolor extract powder on Corn Chip.
Figure 73:
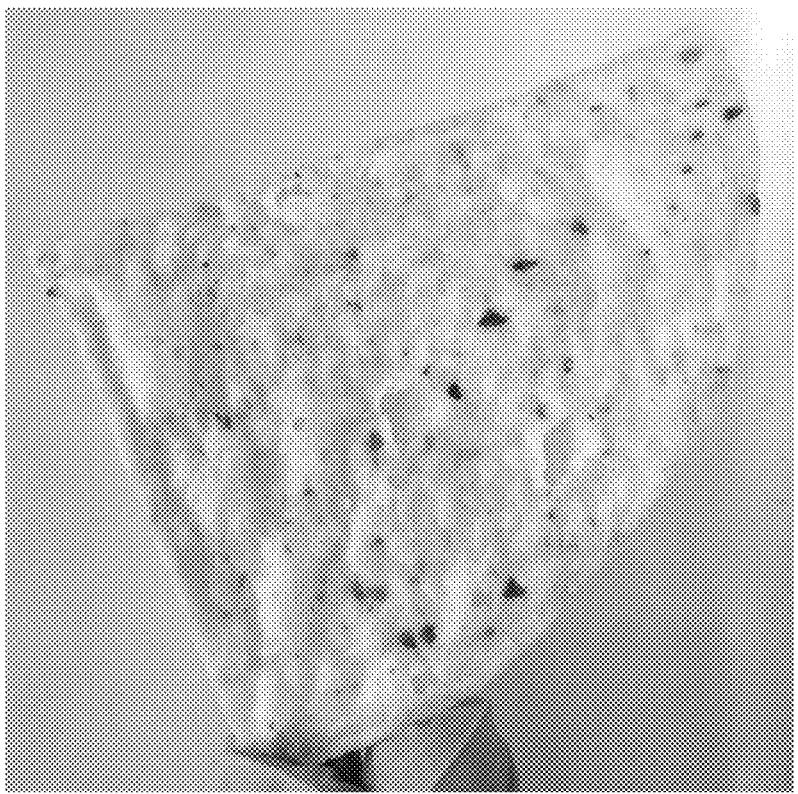

One piece of plain uncolored corn chips (Tostitos) was sprinkled by Maltodextrin added Avocado seed extract powder (2.423% Avocado seed extract) resulting in using only 0.3115 g Maltodextrin added Avocado seed extract powder can be sprinkled on 4.1771 g one piece of Tostitos (FIG. 73).

Figure 74:
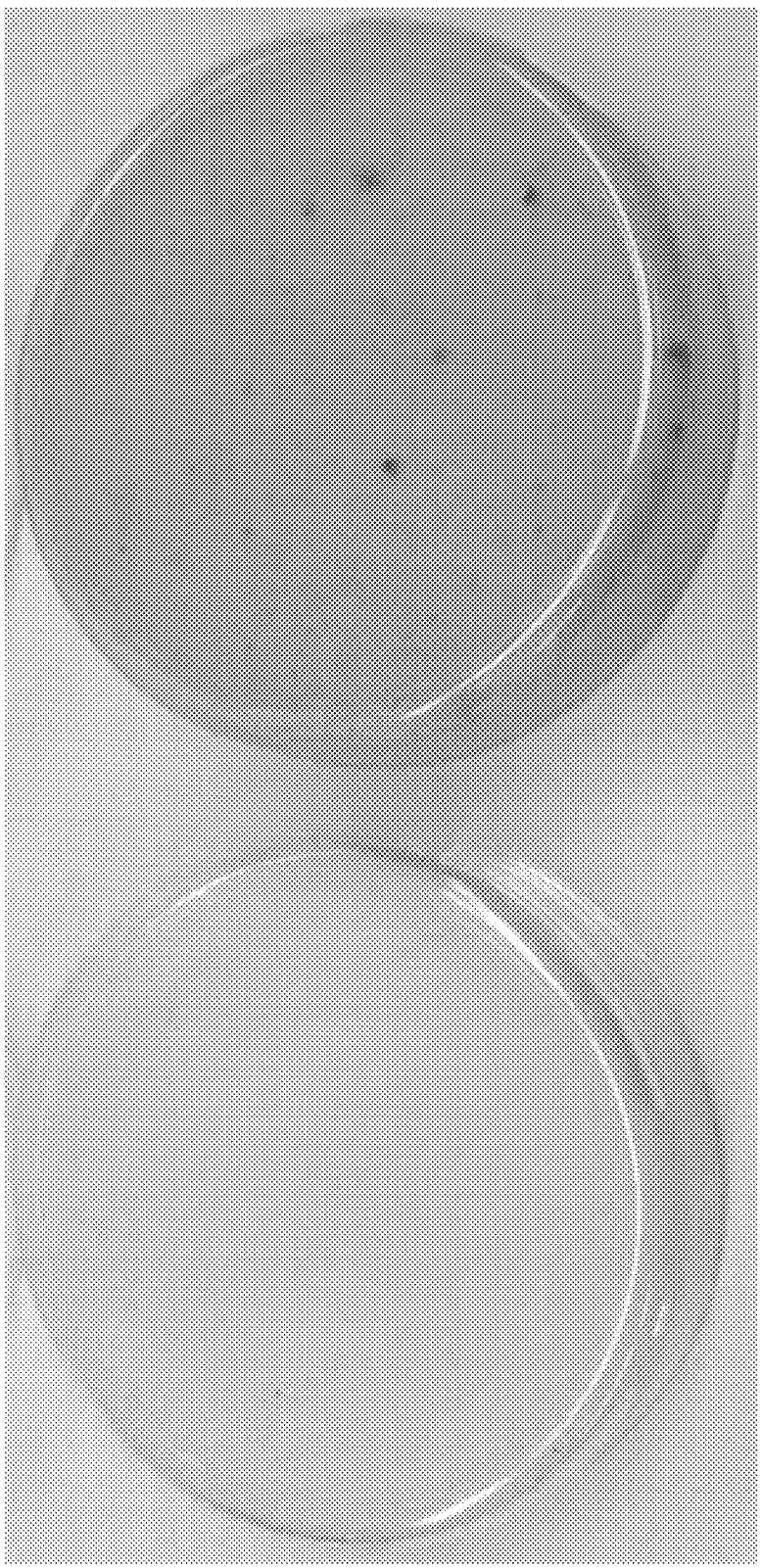
FIG. 74 depicts the colors of of Maltodextrin Avocolor extract powder in white chocolate.

Perseoranjin in White Chocolate 5.1076 g white chocolate was sprinkled by 0.1002 g Maltodextrin added Avocado seed extract powder (2.423% Avocado seed extract) and swirled, the orangish chunk came from the Maltodextrin added Avocado seed extract piece that cannot dissolve in the chocolate at 32° C. (FIG. 74).

Example 7: Structural Determination and Modification of Avocado Seed Extract Perseoranjin To determine the structure of the avocado seed extract perseoranjin, HSCQ (Table 10), HBMC (Table 11, and COSY (Table 12) were obtained

TABLE 10

HSQC Data[a]

| Position | $\delta_C$ | $\delta_H$ |
|---|---|---|
| 1 | 103.31 | 4.02 d (7.7 Hz) |
| 2 | 73.84 | 2.86 brdd. |
| 3 | 76.89 | 3.07 brt. |
| 4 | 70.34 | 3.00 brt. |
| 5 | 77.24 | 3.03 ddd (13, 9, ~1) |
| 6 | 61.45 | 3.63 brd. (11.8), 3.40[b] |
| 1' | 64.12 | 3.78 ddd (15.1, 9.4, ~1), 3.37[b] |
| 2' | 43.86 | 2.10 ddd (14.6, 8.5, 6), 1.93 ddd (14.6, 7.3, ~1) |
| 4' | 50.25 | 3.52 d, (14.6), 3.33[b] |
| 7' | 90.71 | 6.15 s |
| 9' | 28.94 | 2.77 dd (16.3, 4), 2.63 d (16.3) |
| 10' | 64.38 | 4.10 brs. |
| 11' | 80.00 | 5.08 s |
| c | 113.17 | 6.50 s |
| e | 115.16 | 6.95 brs. |
| g | 118.35 | 6.72 d (8.3) |
| h | 115.40 | 6.75 d (8.3) |

[a]In DMSO-d$_6$.
[b]Obscured by the water signal.

TABLE 11

HMBC Data[a]

| Position | $\delta_C$ | $\delta_H$ | Correlations |
|---|---|---|---|
| 1 | 103.33 | 4.02 d | 3.78, 2.86 |
| 2 | 73.84 | 2.86 brdd. | 3.07 |
| 3 | 76.89 | 3.07 brt. | 2.86 |
| 4 | 70.34 | 3.00 brt. | 3.07, 3.03 |
| 5 | 77.24 | 3.03 ddd | 3.00 |
| 6 | 61.45 | 3.63 brd., 3.40[b] | 3.00 |
| 1' | 64.12 | 3.78 ddd, 3.37[b] | 4.02, 2.10, 1.93 |
| 2' | 43.86 | 2.10 ddd, 1.93 ddd | 3.78, 3.52, 3.37, 3.33 |
| 3' | 89.0 | — | 6.50, 3.52, 3.33, 2.10, 1.93 |
| 4' | 50.25 | 3.52 d, 3.33[b] | 1.93 |
| 5' | 166.55 | — | 3.52, 2.10 |
| 6' | 178.38 | — | 3.52 |
| 7' | 90.71 | 6.15 s | (none) |
| 8' | 155.41 | — | 2.63 |
| 9' | 28.94 | 2.77 dd, 2.63 d | (none) |
| 10' | 64.38 | 4.1 brs. | 2.63 |

TABLE 11-continued

HMBC Data[a]

| Position | $\delta_C$ | $\delta_H$ | Correlations |
|---|---|---|---|
| 11' | 80.0 | 5.08 s | 6.95, 6.72, 2.63 |
| 12' | 103.42 | | 6.15 s, 2.77 dd (16.3, 4), 2.63 d (16.3) |
| a | 192.78 | — | 6.50, 3.52, 3.33 |
| b | 102.75 | — | 6.50, 6.15 |
| c | 113.17 | 6.50 s | (none) |
| d | 165.32 | — | 6.15 |
| e | 115.16 | 6.95 brs. | (none) |
| f | 130.12 | — | 6.75, 6.72, 5.08 |
| g | 118.35 | 6.72 d | 6.95, 5.08 |
| h | 115.40 | 6.75 d | 6.72, 5.08 |
| i | 166.60 | — | 3.52 |
| j | 145.40 | — | 6.95, 6.75 |
| k | 145.39 | — | 6.72 |

[a]In DMSO-d$_6$.
[b]Obscured by the water signal.

TABLE 12

COSY Data[a]

| Position | $\delta_H$ | Correlations[b] |
|---|---|---|
| 1 | 4.02 d (7.7) | 2.86 (s) |
| 2 | 2.86 brdd. (9, 7.7) | 4.75 (OH) (m), 4.02 (s), 3.07 (s) |
| 3 | 3.07 brt. (9) | 4.89 (OH) (w), 3.00 (s), 2.86 (s) |
| 4 | 3.00 brt. (9) | 4.89 (OH) (w), 3.07 (s), 3.03 (s) |
| 5 | 3.03 ddd (13, 9, ~1) | 3.63 (w), 3.40 (s), 3.00 (s) |
| 6 | 3.63 brd. (11.8) 3.40[c] | 4.48 (OH) (m), 3.40 (s), 3.03 (w) 4.48 (OH) (m), 3.63 (s), 3.03 (s) |
| 1' | 3.78 ddd (15.1, 9.4, ~1) 3.37[c] | 3.37 (s), 2.10 (m), 1.93 (m) 3.78 (s), 2.10 (m), 1.93 (m) |
| 2' | 2.10 ddd (14.6, 8.5, 6) 1.93 ddd (14.6, 7.3, ~1) | 3.78 (m), 3.37 (m), 1.93 (s) 3.78 (m), 3.37 (m), 2.10 (s) |
| 4' | 3.52 d (14.6) 3.33[c] | 3.33 (s) 3.52 (s) |
| 7' | 6.15 s | (none) |
| 9' | 2.77 dd (16.3, 4) 2.63 d (16.3) | 4.10 (s), 2.63 (s) 5.08 (vw), 4.10 (m), 2.77 (s) |
| 10' | 4.10 brs. | 4.92 (OH) (m), 2.77 (s), 2.63 (m) |
| 11' | 5.08 s | 6.95 (w), 6.72 (m), 2.63 (vw) |
| c | 6.50 s | 6.15 (w) |
| e | 6.95 brs. | 6.72 (m), 6.15 (w), 5.08 (w) |
| g | 6.72 d (8.3) | 6.95 (w), 6.75 (s), 5.08 (m) |
| h | 6.75 d (8.3) | 6.72 (s) |

[a]In DMSO-d$_6$.
[b]Intensities: s = strong, m = medium, w = weak.
[c]Obscured by the water signal.

Derivatization of Perseorajin

Hydrophobic derivatives of perseoranjin were prepared in order to extend the potential color additive activity in foods containing significant amounts of fat. Derivatives were prepared by acylation of perseoranjin by alkali-catalyzed reaction with acyl chlorides. A summary of the expected chemical modification is shown in Scheme 1, where R is an aliphatic or aromatic chain.

Scheme 1.

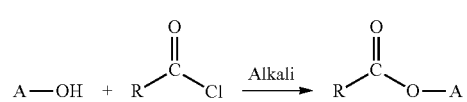

In the reaction of scheme 1, R can be a 1) straight aliphatic chain 1-24 carbons in length with 0-4 degrees of unsaturation; 2) branched aliphatic chain 2-24 carbons in length with 0-4 degrees of unsaturation; 3) phenyl functionality connected to the carbonyl carbon by an aliphatic chain 1-6 carbons in length with 0-3 degrees of unsaturation; 4) naphthyl functionality connected to the carbonyl carbon by an aliphatic chain 1-6 carbons in length with 0-3 degrees of unsaturation; 5) hydroxy phenyl functionality with 1-4 hydroxyl substitutions connected to the carbonyl carbon by an aliphatic chain 1-6 carbons in length with 0-3 degrees of unsaturation; or 6) hydroxy naphthyl functionality with 1-6 hydroxyl substitutions connected to the carbonyl carbon by an aliphatic chain 1-6 carbons in length with 0-3 degrees of unsaturation.

Acetylation of Perseoranjin

AvoColor (1 mass equivalent) was suspended in 10 mass equivalents of ice-cold anhydrous dichloromethane. Triethylamine (43 mass equivalents) were added to the reaction. A catalytic amount of 4-dimethylaminopyridine was added to the reaction. The reaction was stirred on ice and acetyl chloride (16 mass equivalents) dissolved in 10 mass equivalents of dichloromethane was added dropwise over 10 min. The reaction was stirred overnight and allowed to return to room temperature. The reaction was stopped by addition of water. The reaction mixture was extracted with three times with dichloromethane. The dichloromethane fraction was dried under vacuum to yield a red-brown solid. The red-brown solid was readily soluble in acetone and ethyl acetate, but not water. The red-brown product was solubilized in ethyl acetate and extracted 3 times with 1 M HCl. The ethyl acetate fraction turned from red-brown to yellow-orange. The ethyl acetate fraction was dried under vacuum to yield an orange solid. This solid is referred to as acetylated perseoranjin.

Benzoylation of Perseoranjin

AvoColor (1 mass equivalent) was suspended in 10 mass equivalents of ice-cold anhydrous dichloromethane. Triethylamine (48 mass equivalents) were added to the reaction. A catalytic amount of 4-dimethylaminopyridine was added to the reaction. The reaction was stirred on ice and acetyl chloride (40 mass equivalents) dissolved in 10 mass equivalents of dichloromethane was added dropwise over 10 min. The reaction was stirred overnight and allowed to return to room temperature. The reaction was stopped by addition of 1 M HCl. The dichloromethane phase was yellow. The dichloromethane fraction was collected and extracted three times with 1 M HCl. The dichloromethane phase was dried under vacuum yielding a yellow oil that is readily soluble in ethyl acetate and dichloromethane but not water. This oil is referred to as benzoylated perseoranjin.

Figure 75:
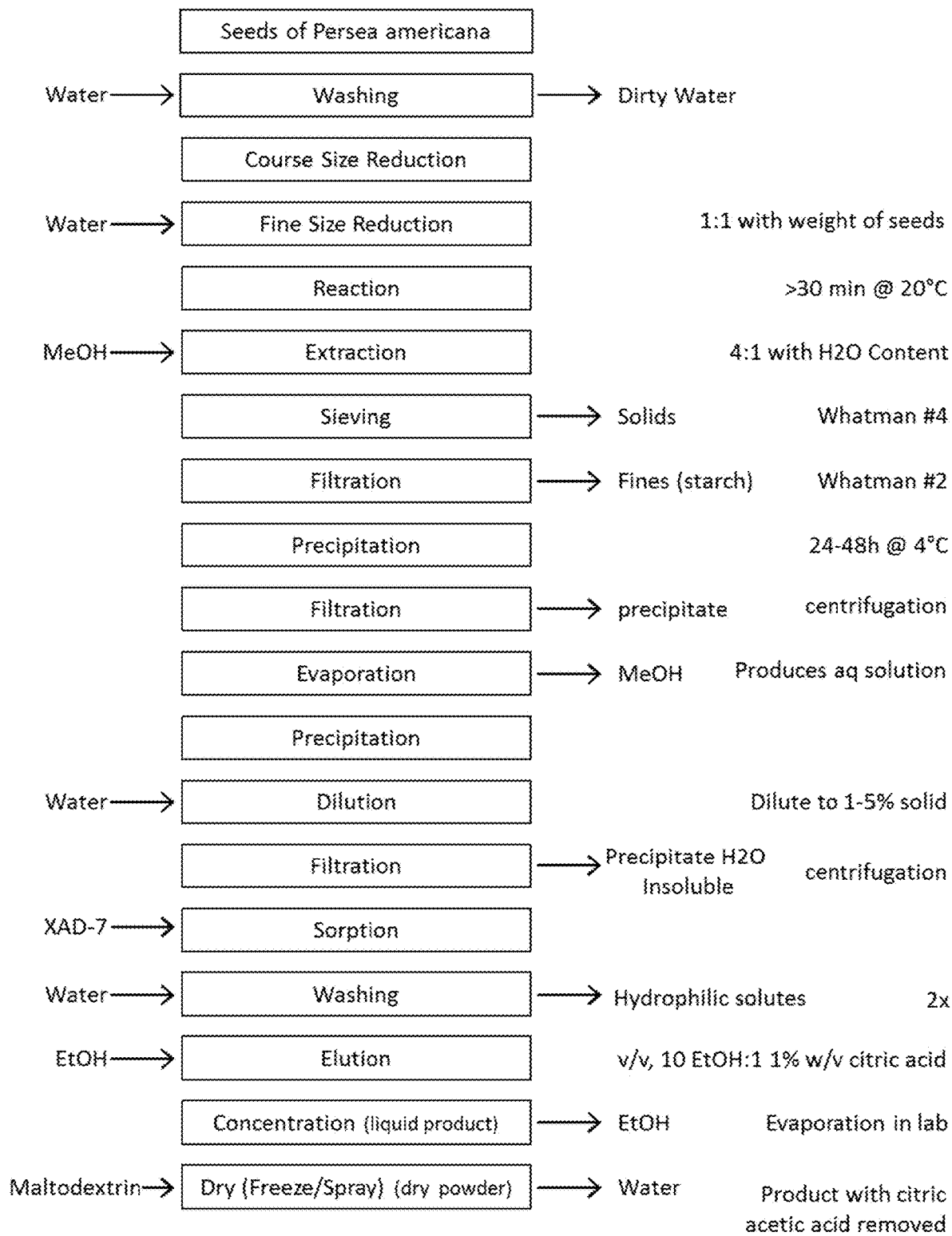
FIG. 75 depicts a flow chart demonstrating the method of isolating perseoranjin.

The Avocolor compound can be isolated using the procedural flow chart depicted in FIG. 75. Seeds of Persea Americana are washed in water and their size is reduced in two steps, first a coarse size reduction and second a fine size reduction. The product is then incubated for at least 1 minute and up to a few days at a temperature of 0-40° C. Extraction of perseoranjin is carried out using MeOH, EtOH or solvents with similar polarities such as acetone or alcohol/water mixture. The liquid is then collected by filtering the extracted product through a Whatman No. 4 sieve to remove solids. A second filtration step, through a Whatman No. 2 sieve, removes the starches. The impurities in the liquid are then precipitated by incubation for at least 24-48 hours at 4° C. The precipitate is removed through filtration or centrifugation and the liquid is collected. The liquid is undergoes sorption through resin, such as XAD-7. The resin is washed twice with water to remove the hydrophilic solutes. The perseoranjin is then eluted from the resin using EtOH, MeOH, acetone, citric acid, acetic acid or any combination thereof. The colorant is then concentrated by evaporation. If desired, the product can be dried through freeze drying or spray drying with an excipient such as maltodextrin or a sugar.

The disclosures of each and every patent, patent application, and publication cited herein are hereby incorporated herein by reference in their entirety.

While the invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of isolating a stable compound selected from the group consisting of

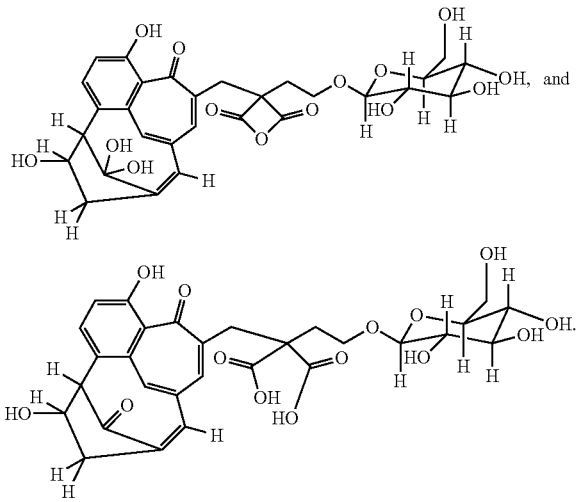

wherein the method comprises the steps of:

obtaining a seed of Persea americana;

grinding the seed to a slurry;

incubating the slurry;

extracting the compound from the incubated slurry by incubating with an alcohol, an organic acid, or a combination thereof, to form a first mixture;

isolating a first liquid from the first mixture;

removing starch from the first liquid;

precipitating an impurity in the liquid to form a second mixture;

isolating a second liquid from the second mixture;

precipitating an insoluble material from the second mixture to form a third mixture;

isolating a third liquid from the third mixture;

adsorbing the third liquid to a resin; and eluting a stable compound from the resin with an alcohol, an organic acid, or a combination thereof, thereby isolating the stable compound selected from the group consisting of

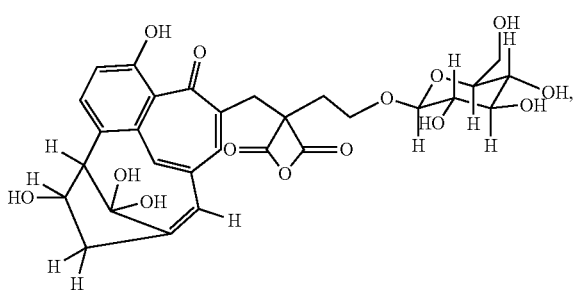

and

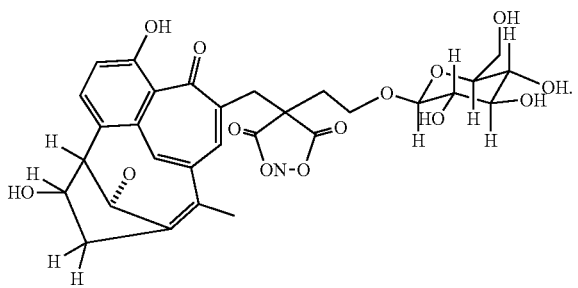

2. The method of claim 1, wherein the alcohol, an organic acid, or a combination thereof, is methanol, ethanol, acetone, citric acid, acetic acid, or any combination thereof.

3. The method of claim 1, wherein the resin is a XAD-7 resin.

4. A method of imparting a color to a substrate, comprising applying the compound isolated by the method of claim 1 to the substrate.

5. The method of claim 4, wherein the color is selected from the group consisting of red, yellow and orange.

6. The method of claim 4, wherein the substrate is an edible material.

7. The method of claim 6, wherein the color is selected from the group consisting of orange, red and yellow.

8. The method of claim 1, wherein the slurry is incubated between about 30 minutes and about 2 hours at a temperature of between about 10° C. and 30° C.

* * * * *